(12) United States Patent
Makino et al.

(10) Patent No.: US 8,846,277 B2
(45) Date of Patent: Sep. 30, 2014

(54) COMPOUND, POLYMERIZABLE COMPOSITION, COLOR FILTER, AND METHOD OF PRODUCING THE SAME, SOLID-STATE IMAGING DEVICE, AND PLANOGRAPHIC PRINTING PLATE PRECURSOR

(75) Inventors: Masaomi Makino, Shizuoka (JP); Tomotaka Tsuchimura, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 245 days.

(21) Appl. No.: 13/144,600

(22) PCT Filed: Jan. 12, 2010

(86) PCT No.: PCT/JP2010/050196
§ 371 (c)(1),
(2), (4) Date: Jul. 14, 2011

(87) PCT Pub. No.: WO2010/082554
PCT Pub. Date: Jul. 22, 2010

(65) Prior Publication Data
US 2011/0267714 A1 Nov. 3, 2011

(30) Foreign Application Priority Data

Jan. 15, 2009 (JP) ................................. 2009-006628
Dec. 25, 2009 (JP) ................................. 2009-296230

(51) Int. Cl.
*G02B 5/20* (2006.01)
*G03F 7/028* (2006.01)

(52) U.S. Cl.
USPC ........................................... 430/7; 430/270.1

(58) Field of Classification Search
None
See application file for complete search history.

(56) References Cited

U.S. PATENT DOCUMENTS

| 4,255,513 A | 3/1981 | Laridon et al. |
| 4,590,145 A | 5/1986 | Itoh et al. |
| 6,485,885 B1 | 11/2002 | Oka et al. |
| 6,596,445 B1 * | 7/2003 | Matsumoto et al. ............. 430/7 |

FOREIGN PATENT DOCUMENTS

| EP | 2 105 443 A1 | 9/2009 |
| EP | 2 116 527 A1 | 11/2009 |
| EP | 2141206 A1 | 1/2010 |
| JP | 2000-080068 A | 3/2000 |
| JP | 2001-233842 A | 8/2001 |
| JP | 2005-202252 A | 7/2005 |
| JP | 2006-162784 A | 6/2006 |
| JP | 2006-342166 A | 12/2006 |
| JP | 2007-231000 A | 9/2007 |
| JP | 2009-227624 A | 10/2009 |
| JP | 2010-032985 A | 2/2010 |
| WO | 00/00869 A1 | 1/2000 |
| WO | 00/52530 A1 | 9/2000 |

OTHER PUBLICATIONS

Communication, dated Sep. 19, 2012, issued in corresponding EP Application No. 10731223.3, 9 pages.
Communication pursuant to Article 94(3) EPC, dated Oct. 11, 2013, issued in corresponding EP Application No. 10 731 223.3, 6 pages in English.
Office Action, dated Mar. 26, 2014, issued in corresponding TW Application No. 099100865, 7 pages in English and Chinese.

\* cited by examiner

*Primary Examiner* — John A. McPherson
(74) *Attorney, Agent, or Firm* — Sughrue Mion, PLLC

(57) ABSTRACT

Provided is a photopolymerizable composition that is highly sensitive to light having wavelengths of 365 nm and 405 nm, and is capable of forming a curable film that can suppress deterioration in physical properties of the film due to heat-aging. The photopolymerizable composition include: (A) an oxime polymerization initiator which includes a condensed ring formed by containing two or more rings selected from an aromatic ring and a heterocyclic ring, and a cyclic structure which is connected to the condensed ring, the cyclic structure containing a carbonyl group and having an oxime group directly connected to the carbonyl group; and (B) a polymerizable compound.

17 Claims, No Drawings

COMPOUND, POLYMERIZABLE COMPOSITION, COLOR FILTER, AND METHOD OF PRODUCING THE SAME, SOLID-STATE IMAGING DEVICE, AND PLANOGRAPHIC PRINTING PLATE PRECURSOR

CROSS REFERENCE TO RELATED APPLICATIONS

This application is a National Stage of International Application No. PCT/JP2010/050196 filed on Jan. 12, 2010, which claims priority from Japanese Patent Application Nos. 2009-006628, filed on Jan. 15, 2009 and 2009-296230, filed on Dec. 25, 2009, the contents of all of which are incorporated herein by reference in their entirety.

TECHNICAL FIELD

The present invention relates to a polymerizable composition, a novel compound contained in the polymerizable composition, a color filter formed by using the polymerizable composition and a method of producing the same, a solid-state imaging device having the color filter, and a planographic printing plate precursor.

BACKGROUND ART

As a photopolymerizable composition, for example, there is a photopolymerizable composition, in which a photopolymerization initiator is added to a polymerizable compound having an ethylenic unsaturated bond. Such a photopolymerizable composition is polymerized and cured by being irradiated with light, and is used for a photocurable ink, a photosensitive printing plate, a color filter, various photoresists, and the like.

Further, there is another embodiment, in which, for example, a photopolymerizable composition generates an acid by being irradiated with light, and the generated acid is used as a catalyst. Specifically, the photopolymerizable composition is used for a material for image formation, forgery prevention, and energy radiation-dose detection, by utilizing the color reaction of a dye precursor catalyzed by the generated acid, or the photopolymerizable composition is used for a positive-working photoresist, and the like for manufacturing a semiconductor, a TFT, a color filter, a component for a micromachine, and the like, by utilizing a decomposition reaction by the generated acid.

In recent years, in particular, photopolymerizable compounds that are sensitive to a light source having a short wavelength (for example, 365 nm and 405 nm) have been demanded for various uses, and demand for compounds having excellent sensitivity to such a short wavelength light source, for example, for photopolymerization initiators, has been increasing. However, photopolymerization initiators having excellent sensitivity are generally unstable, and accordingly, photopolymerization initiators simultaneously achieving increased sensitivity and storage stability simultaneously, are desired.

For this reason, as photopolymerization initiators used for the photopolymerizable composition, oxime ester derivatives are proposed (for example, refer to U.S. Pat. No. 4,255,513, U.S. Pat. No. 4,590,145, Japanese Patent Application Laid-Open (JP-A) No. 2000-80068, JP-A No. 2001-233842, JP-A No. 2006-342166, and JP-A No. 2007-231000). However, since these known oxime ester compounds have low light absorptivity in the wavelength of 365 nm and/or the wavelength of 405 nm, they are still unsatisfactory in view of sensitivity.

Further, currently, photopolymerizable compositions which have excellent storage storability and excellent sensitivity to light in short wavelengths such as 356 nm and/or 405 nm or the like are also desired.

Furthermore, a colored radiation-sensitive composition for color filters, which contains an oxime compound, is disclosed (for example, JP-A No. 2005-202252); however, the storage stability and the sensitivity to lights of short wavelengths were still insufficient.

Moreover, in colored radiation-sensitive compositions for color filters, the reproducibility of color hue after pattern formation is a new issue, and a solution to the problem of change in colorability with the passage of time has been strongly desired.

Meanwhile, for the purpose of improving image quality owing to the light collectivity and the high color separation property of a solid-state imaging device such as a CCD in the color filter for image sensors, there is a strong demand for high color density and thinning of color filters. When a colorant is used in a large amount in order to obtain a high color density, the sensitivity for reproducing a minute pixel pattern shape of 2.5 μm or less with high fidelity becomes insufficient, and defects in the overall pattern tend to occur frequently. In addition, in order to eliminate these defects, light irradiation with high energy is required so that light exposure time is prolonged, thereby reducing the production yield remarkably.

As described above, from the viewpoint of the necessity of obtaining good pattern formability while the colored radiation-sensitive composition contains a colorant (coloring agent) in the filter at high concentration, currently, it is required that the sensitivity of the colored radiation-sensitive composition for color filter be high.

SUMMARY OF THE INVENTION

Technical Problem

According to a first aspect of the present invention, there is provided a polymerizable composition that has a high sensitivity to light of wavelengths of 365 nm and 405 nm, and is capable of forming a cured film whose coloration caused by heat-aging is suppressed.

According to a second aspect of the present invention, there is provided a polymerizable composition that is curable with high sensitivity, has excellent pattern formability, forms a colored pattern with excellent adhesion to a support, has an excellent pattern shape even at heat-aging after development, and is used for forming colored areas of a color filter.

According to a third aspect of the present invention, there is provided a color filter that is formed by the polymerizable compound used for forming the colored areas of the color filter, and has a colored pattern having a good pattern profile and excellent adhesion to a support; a manufacturing method for the color filter with high productivity; and further, a solid-state imaging device.

According to a fourth aspect of the present invention, there is provided a planographic printing plate precursor capable of forming an image by using the polymerizable composition.

According to a fifth aspect of the present invention, there is provided a novel oxime compound that is suitably used for the polymerizable compound.

Solution to Problem

As the result of intensive studies by the inventors, it was found that a photopolymerizable composition, which has good light absorptivity to lights having wavelengths of 365 nm and 405 nm, and an excellent storage stability, can be obtained by using a novel oxime compound.

Concrete means of the invention are shown below.

<1> A polymerizable composition including:

(A) an oxime polymerization initiator including: a condensed ring formed by including two or more rings selected from an aromatic ring and a heterocyclic ring; and a cyclic structure which is connected to the condensed ring, the cyclic structure including a carbonyl group and having an oxime group directly connected to the carbonyl group; and (B) a polymerizable compound.

<2> The polymerizable composition according to <1>, wherein (A) the oxime polymerization initiator is a compound represented by the following Formula (1):

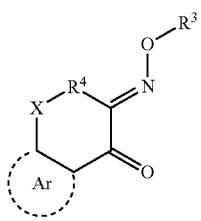

wherein, in Formula (1), Ar represents a condensed ring formed by containing two or more rings selected from an aromatic ring and a heterocyclic ring; X represents a carbon atom, an oxygen atom, a sulfur atom or a nitrogen atom; $R^3$ represents an acyl group or a sulfonyl group; and $R^4$ represents —(CHR)$_n$—, wherein R represents a hydrogen atom, an alkyl group, or an aromatic ring group, and n represents an integer of from 0 to 2.

<3> The polymerizable composition according to the above <1> or <2>, wherein (A) the oxime polymerization initiator is a compound represented by the following Formula (1A) or the following Formula (1B):

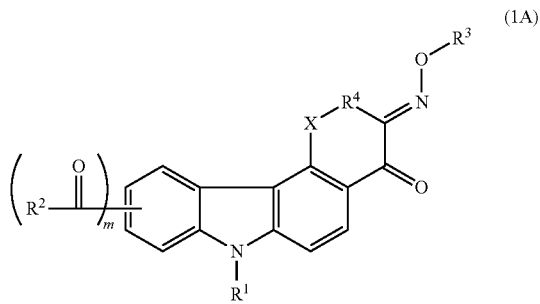

wherein, in Formula (1A) and Formula (1B), $R^1$ and $R^2$ each independently represent an alkyl group, an aryl group or a heterocyclic group; $R^3$ represents an acyl group or a sulfonyl group; $R^4$ represents —(CHR)n-, wherein R represents a hydrogen atom, an alkyl group or an aromatic ring group, and n represents an integer of from 0 to 2; m represents 0 or 1; and X represents a carbon atom, an oxygen atom, a sulfur atom, or a nitrogen atom.

<4> The polymerizable composition according to <3>, wherein $R^2$ in Formula (1A) and Formula (1B) is a substituent represented by the following Formula (2):

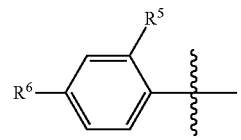

wherein, in Formula (2), $R^5$ and $R^6$ each independently represent a hydrogen atom, a halogen atom, an alkyl group, an aryl group, a hydroxyl group, a thiol group, an amino group, a morpholino group, an alkyloxycarbonyl group, an acyloxy group, an alkoxy group, an alkylthio group, or an alkylseleno group.

<5> The polymerizable composition according to any one of <1> to <4>, further including (C) a colorant.

<6> The polymerizable composition according to <5>, further comprising (D) a pigment dispersant, wherein (C) the colorant is a pigment.

<7> The polymerizable composition according to <5> or <6>, wherein (C) the colorant is a black colorant.

<8> The polymerizable composition according to any one of <5> to <7>, wherein the polymerizable composition is used for forming a colored area in a color filter.

<9> A color filter including: a support; and a colored area formed by using the polymerizable composition according to <8>, on the support.

<10> A method of producing a color filter, including:

applying the polymerizable composition according to <8> to a support to form a polymerizable composition;

subjecting the polymerizable composition layer to pattern exposure; and developing the polymerizable composition layer after the exposure to form a colored pattern.

<11> A solid-state imaging device, including the color filter according to <9>.

<12> A planographic printing plate precursor, including:

a support; and a photosensitive layer including the polymerizable composition according to any one of <1> to <5>, on the support.

<13> A compound represented by the following Formula (1A) or the following Formula (1B):

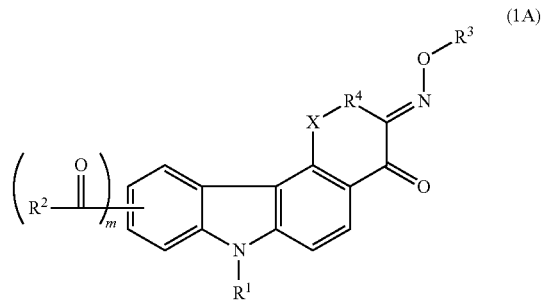

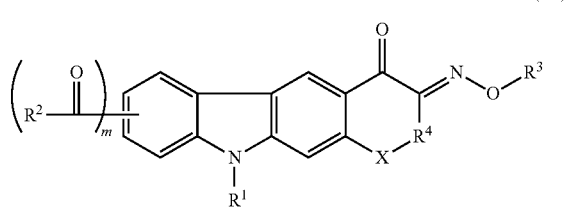

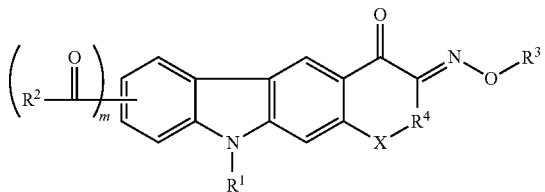

(1B)

wherein, in formula (1A) and Formula (1B), $R^1$ and $R^2$ each independently represent an alkyl group, an aryl group or a heterocyclic group; $R^3$ represents an acyl group or a sulfonyl group; $R^4$ represents —(CHR)n-, wherein R represents a hydrogen atom, an alkyl group or an aromatic ring group, and n represents an integer of from 0 to 2; m represents 0 or 1; and X represents a carbon atom, an oxygen atom, a sulfur atom or a nitrogen atom.

Effect of the Invention

According to an aspect of the invention, there are provided a polymerizable composition, which is highly sensitive to the light of the wavelengths of 365 nm and 405 nm, is excellent in storage storability, and further is capable of forming a cured film whose coloration caused by heat-aging is suppressed, and an oxime compound which can be suitably used for the polymerizable composition.

According to another aspect of the invention, there is provided a polymerizable composition, which is excellent in storage storability, is curable with high sensitivity, has excellent pattern formability, forms a colored pattern with excellent adhesion to a support, has excellent pattern profile even at heat-aging after development, and is used for forming colored areas of a color filter.

According to a still another aspect of the invention, there is provided a color filter, which has a colored pattern having a good pattern profile and excellent adhesion to a support, formed by the polymerizable compound that is used for forming the colored areas of the color filter; a manufacturing method of the color filter with high productivity; and a solid-state imaging device.

According to a still another aspect of the invention, there is provided a planographic printing plate precursor capable of forming an image by using the polymerizable composition.

DESCRIPTION OF EMBODIMENTS

The polymerizable composition according to an exemplary embodiment of the invention, includes: (A) an oxime polymerization initiator that includes a condensed ring formed by containing two or more rings selected from an aromatic ring and a heterocyclic ring, and a cyclic structure that is connected to the condensed ring, the cyclic structure having a carbonyl group and having an oxime group directly connected to the carbonyl group (hereinafter may be referred to as a specific oxime compound, as needed), and (B) a polymerizable compound.

The specific oxime compound of the invention functions as a photopolymerization initiator which decomposes when irradiated with light, and initiates or promotes the polymerization of the polymerizable compound. In particular, since the specific oxime compound has excellent sensitivity to the light source of 365 nm and 405 nm, the specific oxime compound exerts excellent effect when used as a photopolymerization initiator in the photopolymerizable composition.

Hereinafter, each component contained in the polymerizable compound of the invention is explained.

The specific oxime compound of the invention is a compound having a condensed ring formed by containing two or more rings selected from an aromatic ring and a heterocyclic ring. The condensed ring is preferably a condensed ring obtained by condensing 2 to 10 rings, more preferably a condensed ring obtained by condensing 2 to 7 rings, and still more preferably a condensed ring obtained by condensing 3 to 5 rings, selected from an aromatic ring and a heterocyclic ring.

Examples of the aromatic ring that constitutes the condensed ring include a benzene ring, a 5-membered heteroaromatic ring and 6-membered heteroaromatic ring, the aromatic ring having preferably 6 to 30 carbon atoms, more preferably 10 to 25 carbon atoms, and still more preferably 12 to 20 carbon atoms.

Specific examples of the aromatic ring include a benzene ring, a biphenylene ring, a naphthalene ring, an anthracene ring, a phenanthrene ring, a pyrrole ring, naphthacenylene ring, an indene ring, an azulene ring, a cumene ring, a fluorene ring, a mesitylene ring and a furan ring, and a benzene ring, a biphenylene ring, a naphthalene ring and an anthracene ring are more preferable.

The heterocyclic ring that forms the condensed ring means a ring containing at least one hetero atom such as a nitrogen, oxygen, sulfur or phosphorus atom, as an atom which constitutes the cyclic structure.

The heterocyclic ring is preferably an aromatic or aliphatic heterocyclic ring containing a nitrogen atom, an oxygen atom or a sulfur atom, more preferably an aromatic or aliphatic heterocyclic ring containing a nitrogen atom or an oxygen atom, and still preferably more preferably an aromatic or aliphatic heterocyclic ring containing a nitrogen atom.

Specific examples of the heterocyclic ring include a pyrrole ring, a furan ring, a thiophene ring, a pyridine ring, a pyrazine ring, a pyrimidine ring, a pyridazine ring, a piperazine ring, a pyran ring, a chroman ring, an imidazole ring, a thiazole ring, a pyrazole ring, a morpholine ring, a carbazole ring, a thianthrene ring, a dihydrophenazine ring and a dibenzothiophene ring; and a pyrrole ring, a furan ring, a thiophene ring, a carbazole ring, a thianthrene ring, a dihydrophenazine ring and a dibenzothiophene ring are preferable; and a thiophene ring, a carbazole ring, a thianthrene ring, a dihydrophenazine ring, and a dibenzothiophene ring are more preferable; and a thiophene ring, a carbazole ring, and dibenzothiophene ring are still more preferable.

Although the specific oxime compound in the invention has a condensed ring formed by containing two or more rings selected from an aromatic ring and a heterocyclic ring, an aliphatic hydrocarbon ring may be used as a ring capable of forming the condensed ring, in addition to the aromatic ring and the heterocyclic ring. That is, the condensed ring contained in the specific oxime ring may be formed by further containing an aliphatic hydrocarbon ring in addition to the two or more rings selected from the aromatic ring and the heterocyclic ring.

Examples of the hydrocarbon ring that can be contained in the condensed ring include a hydrocarbon ring having 3 to 20 carbon atoms, and preferably a hydrocarbon ring having 4 to 15 carbon atoms, more preferably a hydrocarbon ring having 5 to 12 carbon atoms, and still more preferably a hydrocarbon ring having 5 to 7 carbon atoms.

The hydrocarbon ring is from 3-membered to 12-membered, preferably from 4-membered to 10-membered, and more preferably from 5-membered to 8-membered, and still more preferably from 5-membered to 7-membered.

As described above, the specific oxime compound is preferably a condensed ring formed by containing 2 to 10 rings selected from an aromatic ring and a heterocyclic ring, and particularly preferably a condensed ring formed by containing 3 to 5 rings selected from an aromatic ring and a heterocyclic ring. When the condensed ring further contains an aliphatic hydrocarbon ring, it is preferable that a cyclic structure be formed by condensing 2 to 5 cyclic structures, in total, selected from an aromatic ring and the heterocyclic ring, and the aliphatic hydrocarbon ring.

In addition to the condensed ring, the specific oxime compound of the present invention has a cyclic structure, which contains an oxime group and is bonded to the condensed ring. The cyclic structure, which is bonded to the condensed ring, contains an oxime group adjacent to a carbonyl group, and has the carbon atom that forms the carbonyl group directly bonded to the oxime group as a carbon atom that forms the cyclic structure.

It is preferable that the cyclic structure having an oxime group be an aliphatic hydrocarbon ring formed by being bonded by condensation with the condensed ring. The substitution position of the oxime group is the α-position, the β-position or the γ-position of the adjacent aromatic ring, and preferably the β-position on the condensed ring.

That is, in the cyclic structure containing an oxime group, the cyclic structure that forms the nucleus of the cyclic structure is a cyclic structure containing the terminal carbon that forms a carbonyl group, and a carbon that forms the oxime group; and the carbon that forms the carbonyl group and the carbon that forms the oxime group are adjacent to each other on the cyclic structure.

The specific oxime compound is not specifically restricted to, as long as the compound is a compound having a condensed ring and a cyclic structure containing an oxime group and a carbonyl group, but the compounds represented by the following Formula (1) are preferred.

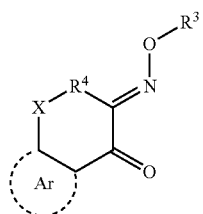

(1)

In Formula (1), Ar represents a condensed ring formed by two or more rings selected from an aromatic ring and a heterocyclic ring; X represents a carbon atom, an oxygen atom, a sulfur atom or a nitrogen atom; $R^3$ represents an acyl group or a sulfonyl group; and $R^4$ represents —(CHR)n-, R represents a hydrogen atom, an alkyl group or an aromatic ring group, and n represents an integer of from 0 to 2.

In Formula (1), the condensed ring formed by two or more rings selected from an aromatic ring and a heterocyclic ring has the same meanings as the condensed ring aforementioned, and the desirable ranges thereof are also the same as those.

In addition, in this description, the aromatic ring, the heterocyclic ring, the acyl group, the sulfonyl group, and an alkyl group, which will be described hereinafter, may further have a substituent, unless otherwise specified.

Hereinafter, examples of the compounds represented by Formula (1) are described. As shown herein, Ar is preferably a condensed ring formed by condensing two or three of a 5-membered ring and a 6-membered ring, which may optionally contain a hetero atom, and may have a substituent such as an alkyl group, an alkoxy group or a halogen atom.

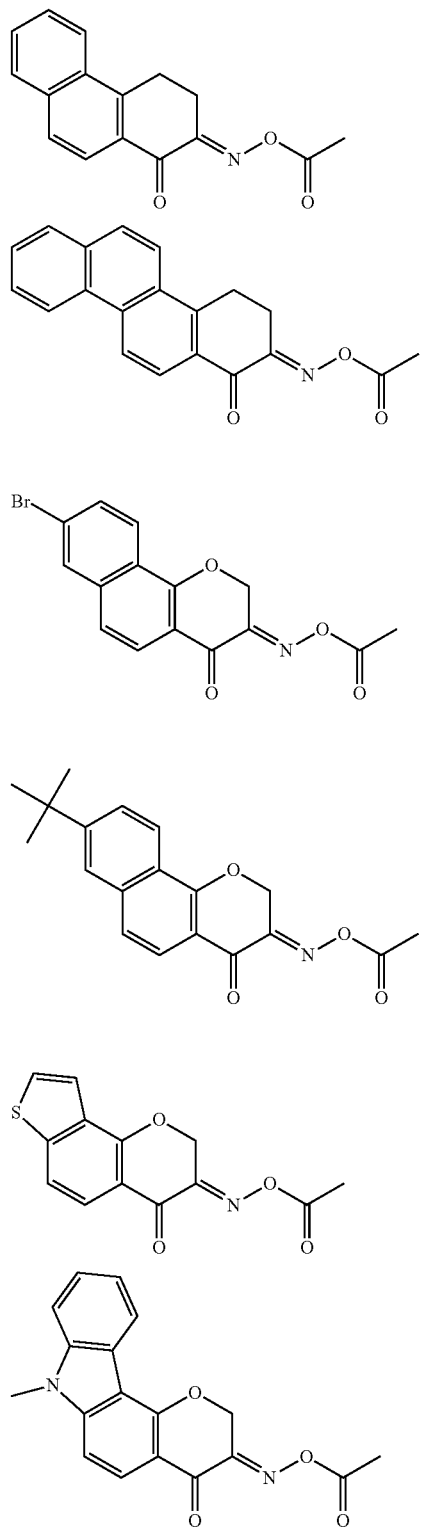

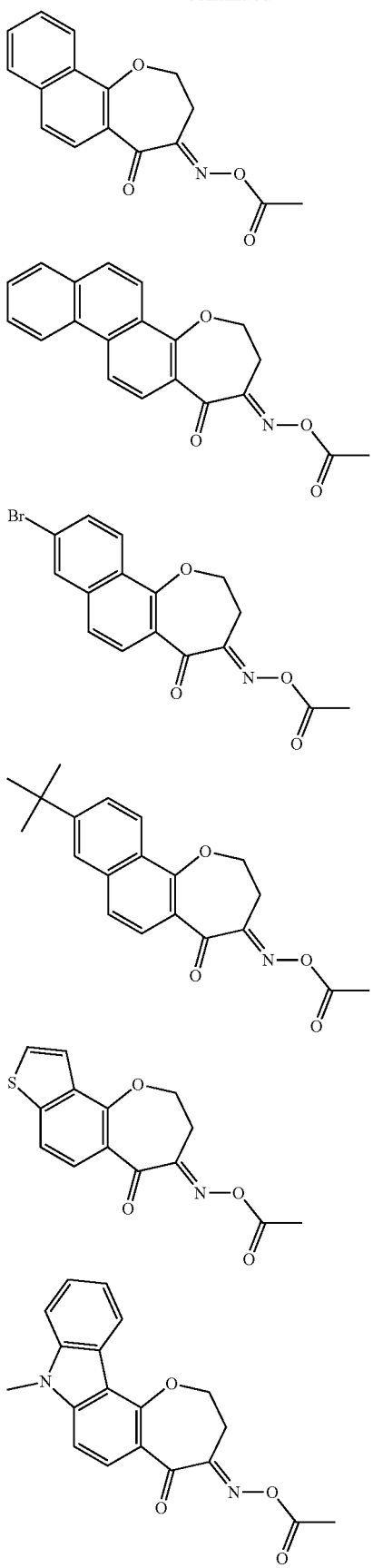
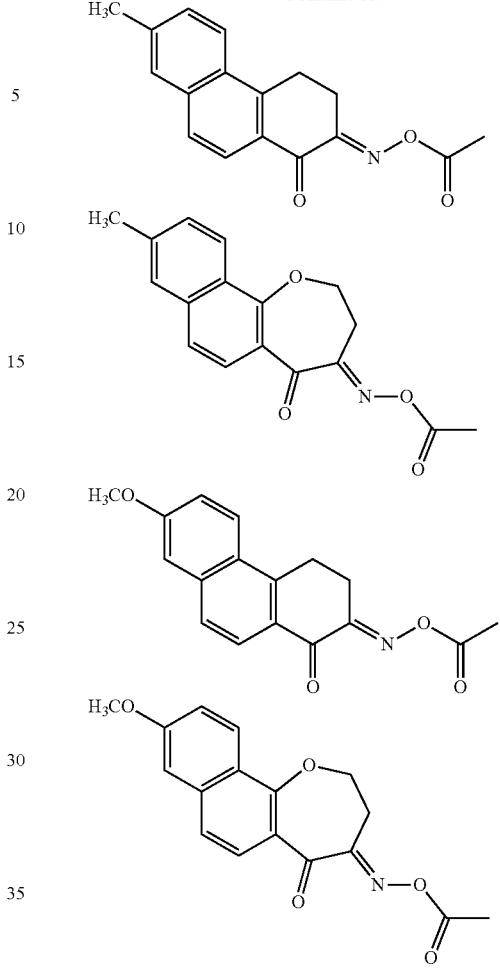

In Formula (1), when R³ represents an acyl group, the acyl group, which may have a substituent, are preferably an acyl group having 2 to 20 carbon atoms, more preferably an acyl group having 2 to 12 carbon atoms, and more preferably an acyl group having 2 to 7 carbon atoms.

Specific examples of the acyl group include an acetyl group, a propanoyl group, a butanoyl group, a trifluoromethylcarbonyl group, a pentanoyl group, a benzoyl group, a toluoyl group, a 1-naphthoyl group, a 2-naphthoyl group, a 4-methylsulfanylbenzoyl group, a 4-phenylsulfanylbenzoyl group, a 4-dimethylaminobenzoyl group, a 4-diethylaminobenzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethylbenzoyl group, a 3-cyanobenzoyl group, a 3-nitrobenzoyl group, a 4-fluorobenzoyl group, a 4-cyanobenzoyl group and a 4-methoxybenzoyl group.

Of the specific examples, the acyl group is preferably an acetyl group, a propanoyl group, a benzoyl group or a toluoyl group; and more preferably an acetyl group or a benzoyl group.

When R³ represents a sulfonyl group, examples of the sulfonyl group include an alkyl sulfonyl group which may have a substituent, and an arylsulfonyl group which may have a substituent. In particular, an alkylsulfonyl group and an alkylsulfonyl halide group, in which part of hydrogen atoms in the alkyl group of the alkylsulfonyl group is substituted with halogen atoms, are preferable, and a fluoroalkylsulfonyl group, in which part of hydrogen atoms in the alkyl group is substituted with fluorine atoms, is more preferable.

Specific examples thereof include a nonafluorobutanesulfonyl group and a perfluorooctane sulfonyl group.

Among them, from the viewpoint of achievement of higher-sensitivity, $R^3$ in Formula (1) is more desirably an acyl group, and, specifically, an acetyl group, a propanoyl group, a benzoyl group and a toluoyl group are desirable.

In Formula (1), n represents an integer of 0 to 2, and 0 or 1 is desirable, and 0 is more desirable. That is, the cyclic structure formed by including a carbonyl group directly bonded to an oxime group is from a 5-membered cyclic ring to a 7-membered cyclic ring, preferably a 5-membered cyclic ring or a 6-membered cyclic ring, and more preferably 5-membered cyclic ring.

In Formula (1), X represents a carbon atom, an oxygen atom, a sulfur atom, or a nitrogen atom, but from the viewpoint of achievement of higher-sensitivity, an oxygen atom, a nitrogen atom or sulfur atom is more preferable, and an oxygen atom is still more preferable.

Further, the aromatic ring which may have a substituent, the heterocyclic ring which may have a substituent, and the acyl group which may have a substituent, as mentioned above, may further be substituted with other substituents.

Examples of the substituent, which can further be introduced into each substituent in Formula (1), include a halogen atom such as a fluorine atom, a chlorine atom, a bromine atom or an iodine atom; an alkoxy group such as a methoxy group, an ethoxy group or a tert-butoxy group; an aryloxy group such as a phenoxy group or a p-tolyloxy group; an alkoxycarbonyl group such as a methoxycarbonyl group, a butoxycarbonyl group or a phenoxy carbonyl group; an acyloxy group such as an acetoxy group, a propionyloxy group or a benzoyloxy group; an acyl group such as acetyl group, a benzoyl group, an isobutylyl group, an acryloyl group, a methacryloyl group or a methoxaryl group; an alkylsulfanyl group such as a methylsulfanyl group or tert-butylsulfanyl groups; an arylsulfanyl group such as a phenylsulfanyl group or p-tolylsulfanyl group; an alkylamino group such as a methylamino group or a cyclohexylamino group; a dialkylamino group such as a dimethylamino group, a diethylamino group, a morpholino group or a piperidino group; an arylamino group such as a phenylamino group or a p-tolylamino group; an alkyl group such as a methyl group, an ethyl group, a tert-butyl group or a dodecyl group; an aryl group such as a phenyl group, a p-tolyl group, a xylyl group, a cumenyl group, a naphthyl group, an anthryl group or a phenanthryl group; and a hydroxyl group, a carboxyl group, a formyl group, a mercapto group, a sulfo group, a mesyl group, p-toluene sulfonyl group, an amino group, a nitro group, a cyano group, a trifluoromethyl group, a trichloromethyl group, a trimethylsylyl group, a phosphinico group, a phosphono group, a trimethylammoniumyl group, a dimethylsulfoniumyl group, and a triphenylphenacylphosphoniumyl group.

As the specific oxime compound represented by Formula (1), the compounds represented by the following Formula (1A) or (1B) are more preferable.

In addition, as a result of studies, it turned out that the compounds represented by the following Formula (1A) or (1B) were new compounds. The new oxime compounds having the structure represented by Formula (1A) or (1B) are very useful as photopolymerization initiators as will described in detail hereinbelow.

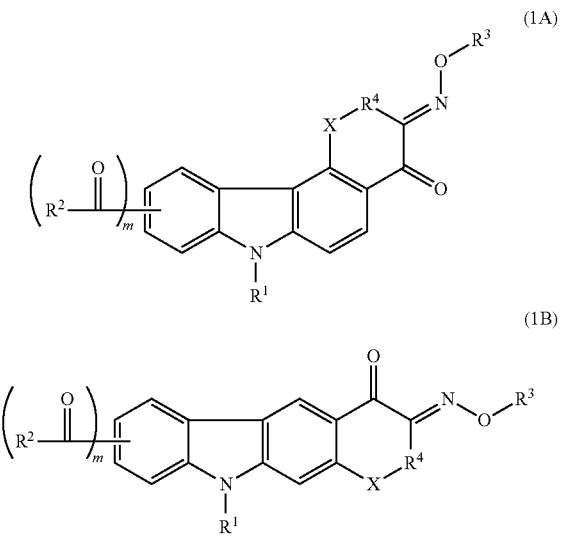

In Formula (1A) and Formula (1B), $R^1$ and $R^2$ each independently represent an alkyl group, an aryl group or a heterocyclic group; $R^3$ represents an acyl group or a sulfonyl group; $R^4$ represents —(CHR)n-, R represents a hydrogen atom, an alkyl group or an aromatic ring group, n represents an integer of from 0 to 2; m represents 0 or 1; and X represents a carbon atom, an oxygen atom, a sulfur atom or a nitrogen atom.

$R^3$, X and n in Formula (1A) and Formula (1B) have the same meanings as $R^3$, X and n in Formula (1), respectively, and the desirable ranges are also the same as those of $R^3$, X and n in Formula (1), respectively.

The alkyl group, the aryl group and the heterocyclic group represented by $R^1$ and $R^2$ in Formulae (1A) and (1B) may further have a substituent.

When $R^1$ and $R^2$ each represent an alkyl group, the alkyl group, which may have a substituent, is preferably an alkyl group having 1 to 30 carbon atoms, more preferably an alkyl group having 1 to 20 carbon atoms, and still more preferably an alkyl group having 1 to 10 carbon atoms.

Specific examples of alkyl group include a methyl group, an ethyl group, a propyl group, a butyl group, a hexyl group, an octyl group, a decyl group, a dodecyl group, an octadecyl group, an isopropyl group, an isobutyl group, a sec-butyl group, t-butyl group, 1-ethylpentyl group, a cyclopentyl group, a cyclohexyl group, a trifluoromethyl group, a 2-ethylhexyl group, a phenacyl group, a 1-naphthoylmethyl group, a 2-naphthoylmethyl group, a 4-methylsulfanylphenacyl group, a 4-phenylsulfanylphenacyl group, a 4-dimethylaminophenacyl group, a 4-cyanophenacyl group, a 4-methylphenacyl group, a 2-methylphenacyl group, a 3-fluorophenacyl group, a 3-trifluoromethylphenacyl group and a 3-nitrophenacyl group.

Of these specific examples, an ethyl group, a 2-ethylhexyl group, an isopentyl group, an ethoxyethyl group, a methoxyethoxyethyl group, a phenoxyethyl group, a methoxyethyl group, a cyclohexylmethyl group and t-butylmethyl group are preferable, and an ethyl group, a 2-ethylhexyl group, an isopentyl group, an ethoxyethyl group, and a cyclohexylmethyl group are more preferable.

When $R^1$ and $R^2$ each represent an aryl group, the aryl group, which may have a substituent, is preferably an aromatic ring group having 6 to 30 carbon atoms, more preferably an aromatic ring group having 6 to 20 carbon atoms, and still more preferably an aromatic ring group having 6 to 10 carbon atoms.

As the specific examples of the aryl group, a phenyl group, an o-tolyl group, an m-tolyl group, and a p-tolyl group are more preferable, and an o-tolyl group is still more preferable.

When $R^1$ and $R^2$ each represent a heterocyclic group, examples of the heterocyclic group includes aromatic or aliphatic heterocyclic groups having a nitrogen atom, an oxygen atom, a sulfur atom or a phosphorus atom.

Specific examples of the heterocyclic group include a thienyl group, a pyridyl group, a furyl group, a pyranyl group, an imidazolyl group, a piperidyl group, a morpholinyl group and a thioxantholyl group, and a thienyl group, a pyridyl group, a furyl group, a pyranyl group and an imidazolyl group are preferable, and a thienyl group, a pyridyl group and a furyl group are more preferable.

Further, $R^2$ in Formula (1A) and Formula (1B) is preferably represented by the following Formula (2).

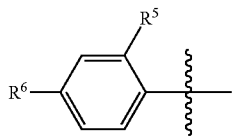

(2)

In Formula (2), $R^5$ and $R^6$ each independently represent a hydrogen atom, a halogen atom, an alkyl group, an aryl group, a hydroxyl group, a thiol group, an amino group, a morpholino group, an alkoxycarbonyl group, an aryloxycarbonyl group, an acyloxy group, an alkoxy group, an alkylthio group or an alkylseleno group. Each substituent may further have a substituent, when the substituent can be introduced into each substituent.

Examples of the halogen atom include fluorine, chlorine, bromine, and iodine, but fluorine and bromine are more preferable, and bromine is still more preferable.

The alkyl group that may have a substituent, and the aryl group that may have a substituent represented by $R^5$ and $R^6$, have the same meanings as the alkyl group and the aryl group represented by $R^1$ and $R^2$ in Formulae (1A) and (1B), and the desirable ranges are also the same as those of $R^1$ and $R^2$.

When $R^5$ and $R^6$ each represent an alkoxycarbonyl group, the alkoxycarbonyl group, which may have a substituent, is preferably a methoxycarbonyl group, an ethoxycarbonyl group or a propoxycarbonyl group, and more preferably a methoxycarbonyl group or an ethoxycarbonyl group.

When $R^5$ and $R^6$ each represent an aryloxycarbonyl group, the aryloxycarbonyl group, which may have a substituent, is preferably a phenoxycarbonyl group, a 1-naphthyloxycarbonyl group, or a 2-naphthyloxycarbonyl group, and a phenoxycarbonyl group is still more desirable.

When $R^5$ and $R^6$ each represent an acyloxy group, as an acyloxy group which may have a substituent, a methylcarbonyloxy group or an ethylcarbonyloxy group is desirable.

when $R^5$ and $R^6$ each represent an alkoxy group, as the alkoxy group that may have a substituent, a methoxy group, an ethoxy group, or a propyloxy group are desirable.

In addition, as an alkoxy group, an alkylthio group, and an alkylseleno group, the compounds represented by the following formulae are more desirable:

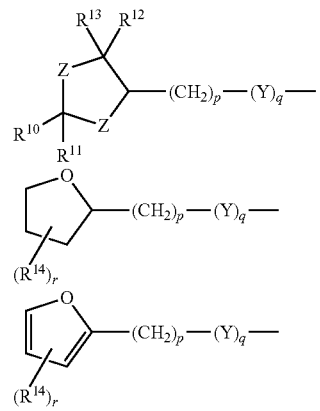

In the above formulae, Y represents an oxygen atom, a sulfur atom or a selenium atom; p represents an integer of 0 to 5; q represents 0 or 1; $R^{10}$, $R^{11}$, $R^{12}$ and $R^{13}$ each independently represent a hydrogen atom, a halogen atom or an alkyl group; Z represents an oxygen atom, a sulfur atom or a selenium atom; $R^{14}$ represents an alkyl group or a halogen atom; and r represents an integer of 0 to 4.

In each Formula above, $R^4$ represents —(CHR)n-, R represents a hydrogen atom, an alkyl group or an aromatic ring group, and n represents an integer of 0 to 2. When n is 2, plural n's may be the same as or different from each other.

When R represents an alkyl group, the alkyl group is preferably an alkyl group having 1 to 5 carbon atoms, and a methyl group or an ethyl group is more desirable, and a methyl group is most desirable.

When R represents an aromatic ring group, examples of the aromatic ring group include an aryl group and a heteroaromatic ring group; a phenyl group, a naphthyl group, a pyridyl group and the like are desirable, a phenyl group and a naphthyl group are more desirable, and a phenyl group is most desirable.

Desirable combinations of the specific oxime compounds represented by Formulae (1A) and (1B), include: $R^1$ is a methyl group, an ethyl group, a propyl group, 2-ethylhexyl group, a phenyl group, an isopentyl group, an ethoxyethyl group, a methoxyethoxyethyl group or a phenoxyethyl group; $R^2$ is a phenyl group, an o-tolyl group, an m-tolyl group, a p-tolyl group, a thienyl group, a pyridyl group or a furyl group; $R^3$ is an acetyl group or a benzoyl group; $R^4$ is a single bond (namely, n=0), —CH$_2$— or —(CH$_2$)$_2$—, —CH(CH$_3$)—, or —CH(Ph)-; X is an oxygen atom or a sulfur atom; and m is 1.

More desirable combinations include: $R^1$ is an ethyl group, an isopentyl group, an ethoxyethyl group, a methoxyethoxyethyl group or a phenoxyethyl group; $R^2$ is a phenyl group, an o-tolyl group, a thienyl group, a pyridyl group or a furyl group; $R^3$ is an acetyl group or a benzoyl group; $R^4$ is —CH$_2$—, —(CH$_2$)$_2$—, —CH(CH$_3$)—, or —CH(Ph)-; X is an oxygen atom or a sulfur atom; and m is 1.

Still more desirable combinations include: $R^1$ is an ethyl group, an isopentyl group or an ethoxyethyl group; $R^2$ is an o-tolyl group; $R^3$ is an acetyl group; $R^4$ is —CH$_2$—, —(CH$_2$)$_2$—, —CH(CH$_3$)— or —CH(Ph)-; X is an oxygen atom or a sulfur atom; and m is 1.

General synthetic scheme of the novel compounds represented by Formulae (1A) and (1B) are represented as follows:

That is, a cyclic ketone having a methylene moiety at the α-position is allowed to react with a nitrite in the presence of a base, so that an oxime can be obtained. Further, the oxime is allowed to react with a carboxylic acid chloride or sulfonic acid chloride in the presence of a base, so that the oxime ester represented by Formulae (1A) and (1B) can be obtained.

In the following formulae, R represents an acyl group or a sulfonyl group.

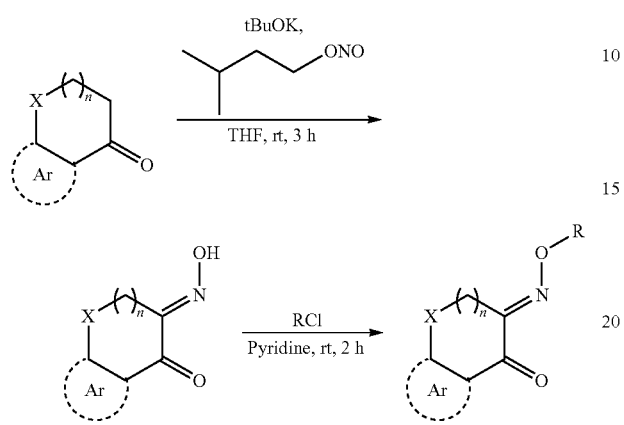

Specific examples of the specific oxime compounds [Exemplary Compounds (A-1) to (A-105)] of the invention are shown below, but the invention is not limited to them.

(A-1)

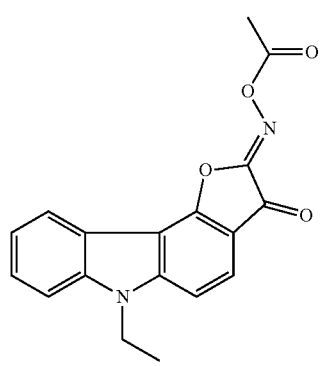

(A-2)

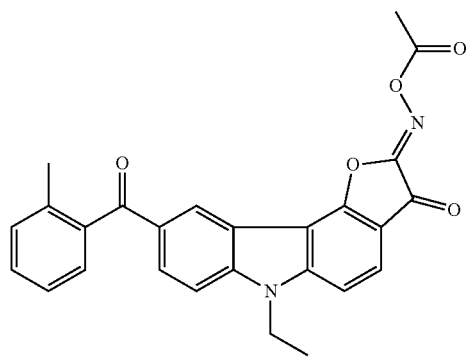

(A-3)

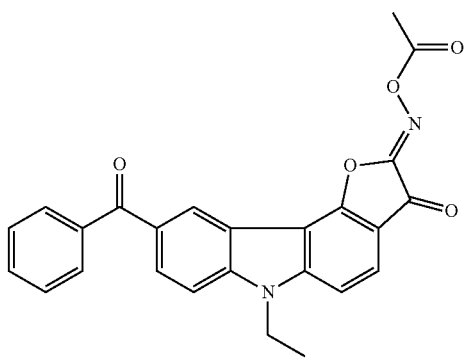

(A-4)

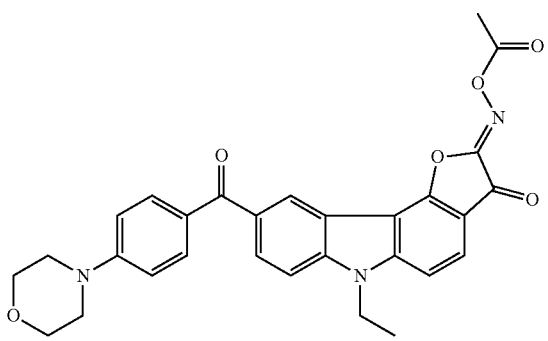

(A-5)

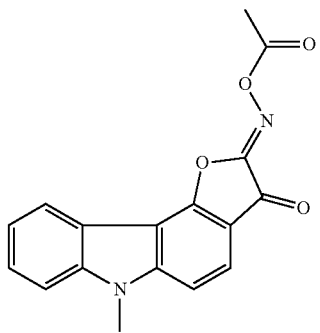

(A-6)

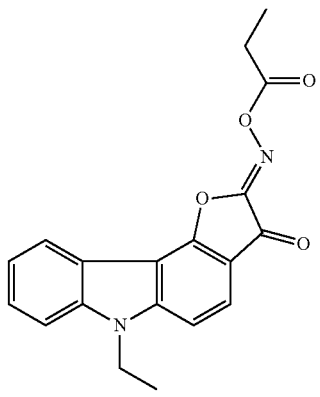

(A-7)
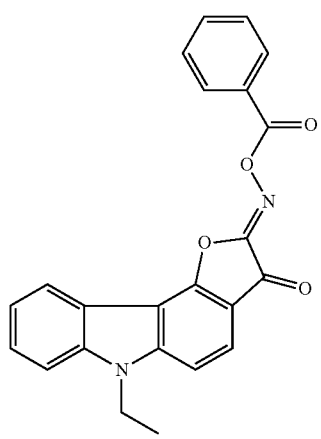
(A-8)
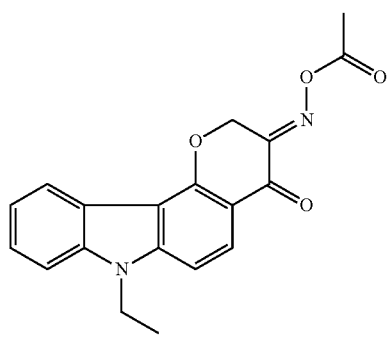
(A-9)
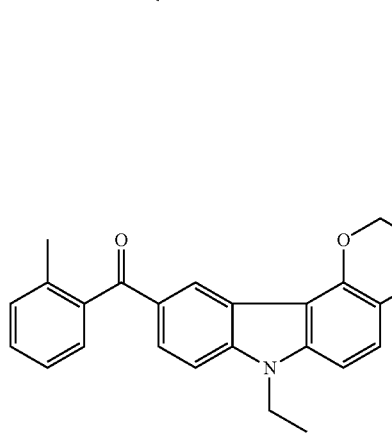
(A-10)
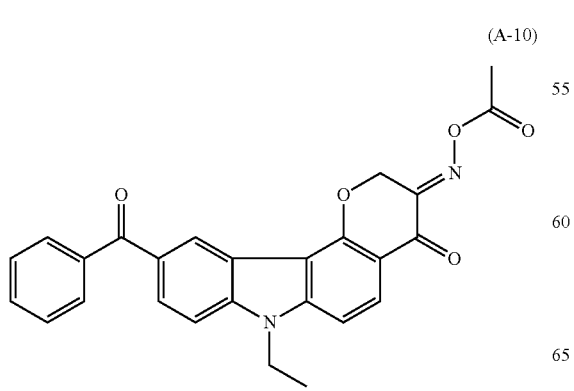
(A-11)
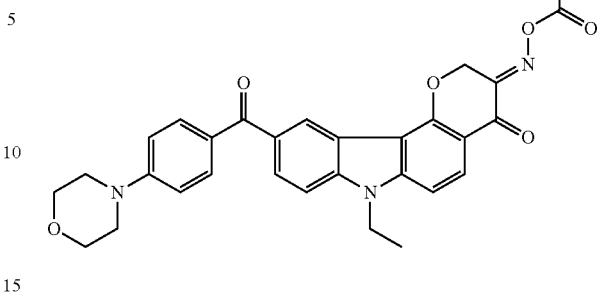
(A-12)
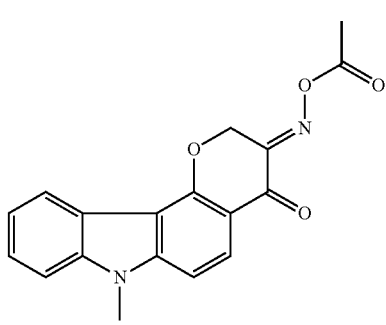
(A-13)
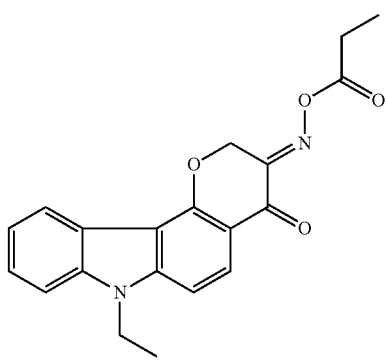
(A-14)
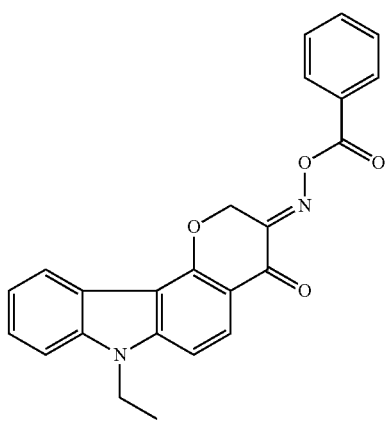

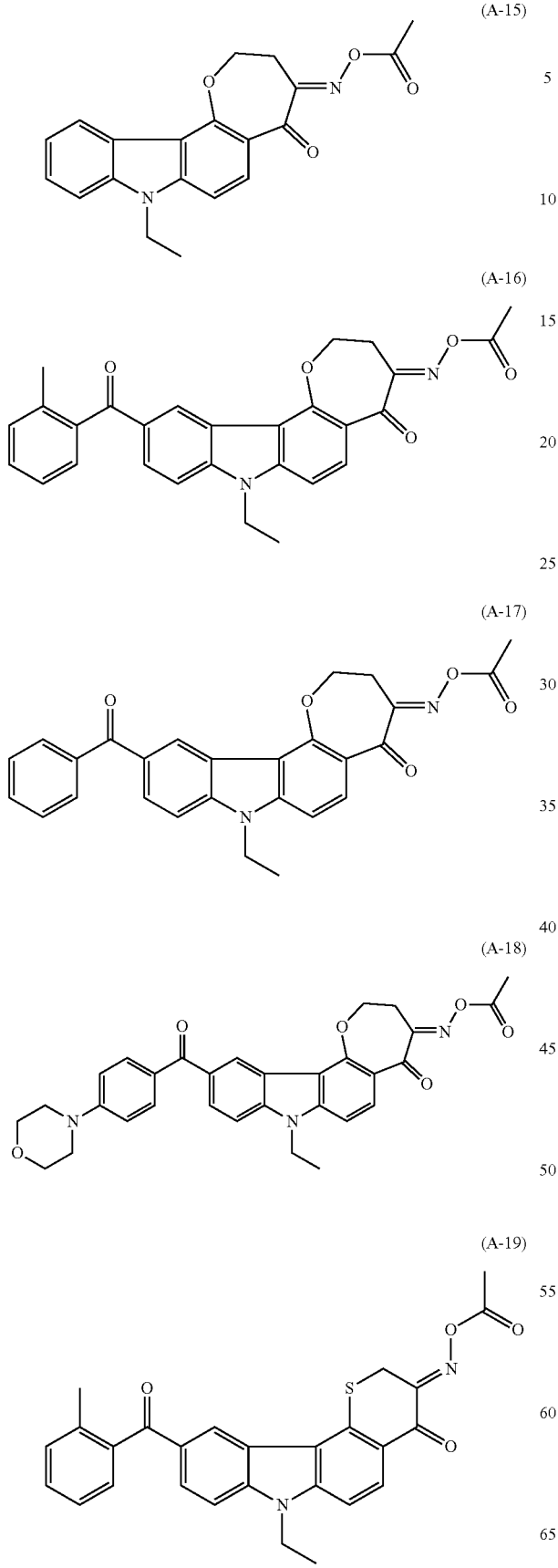
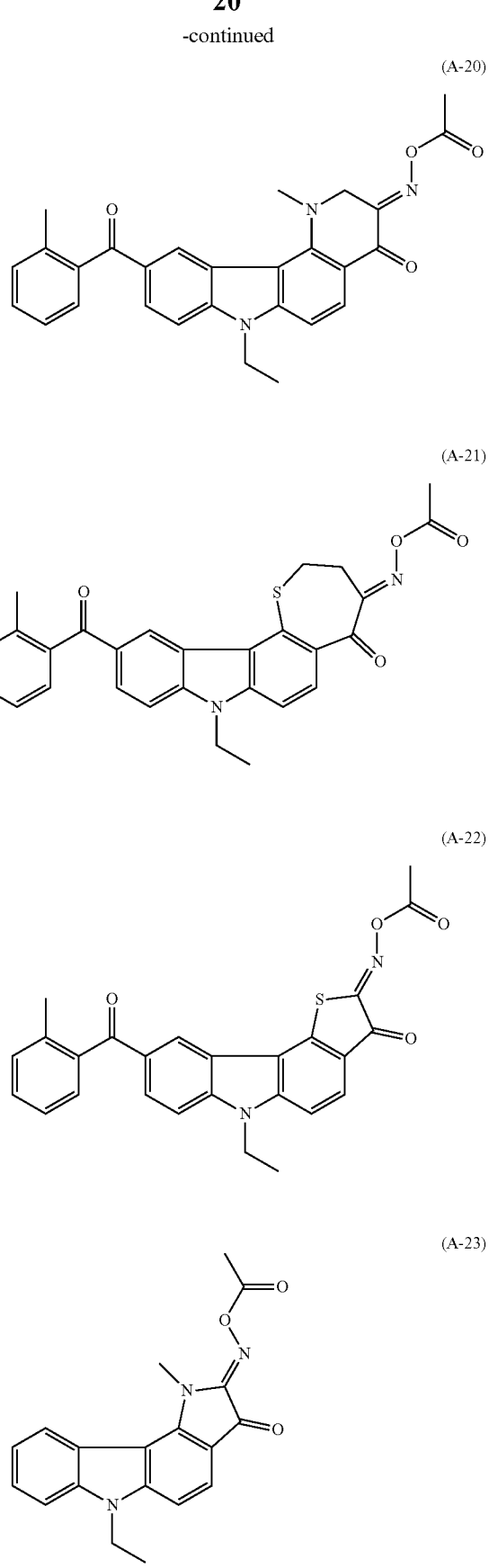

-continued
(A-24)
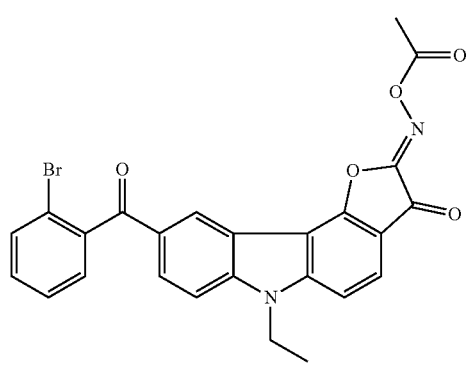
(A-25)
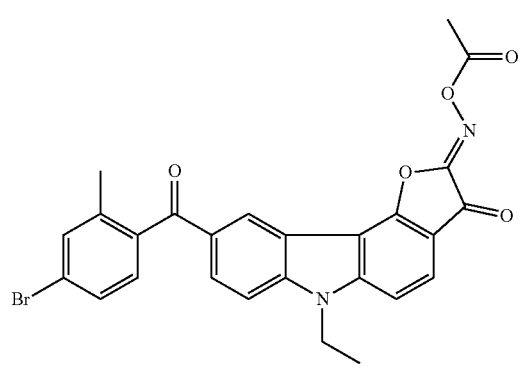
(A-26)
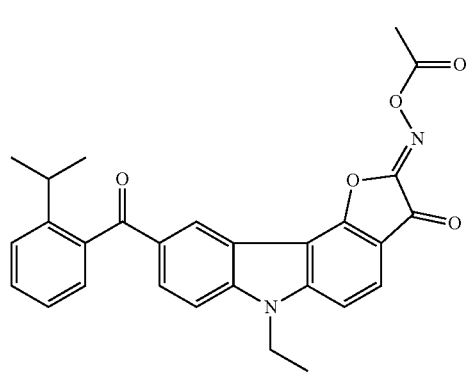
(A-27)
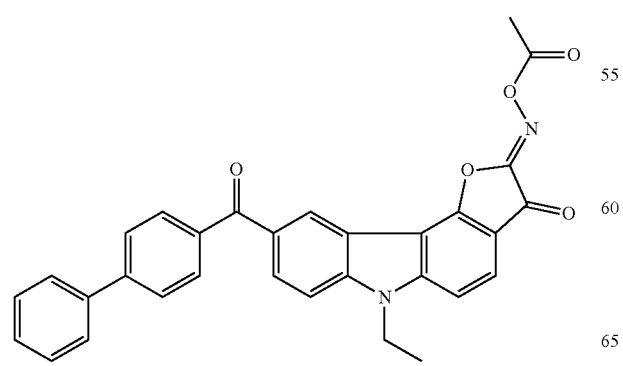
(A-28)
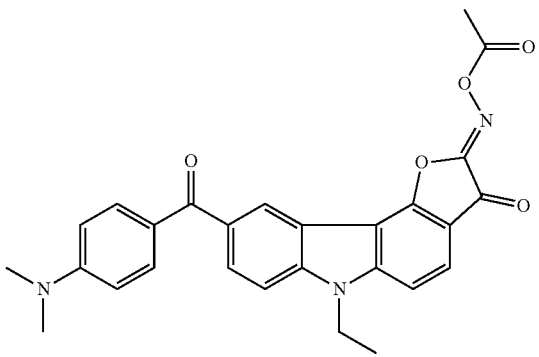
(A-29)
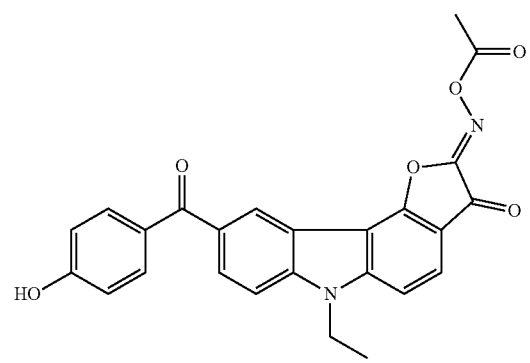
(A-30)
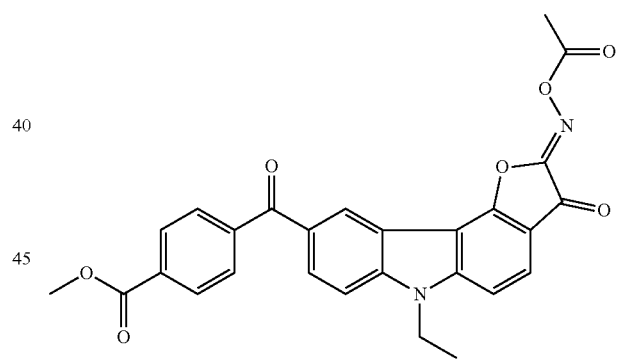
(A-31)
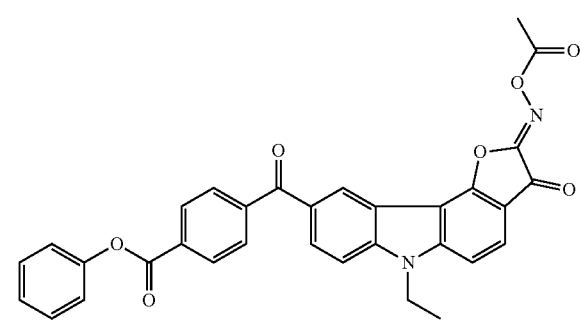

(A-32)
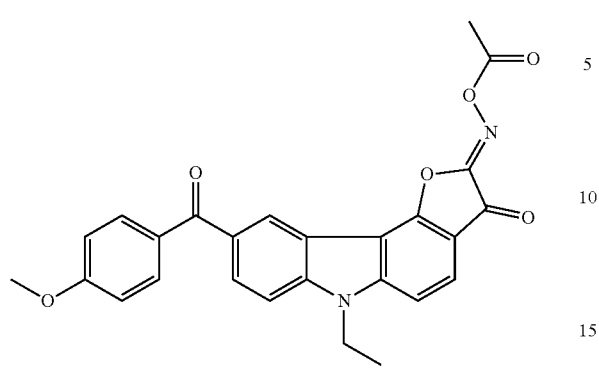
(A-33)
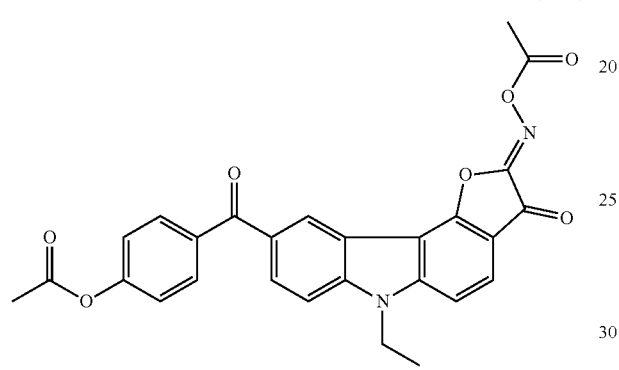
(A-34)
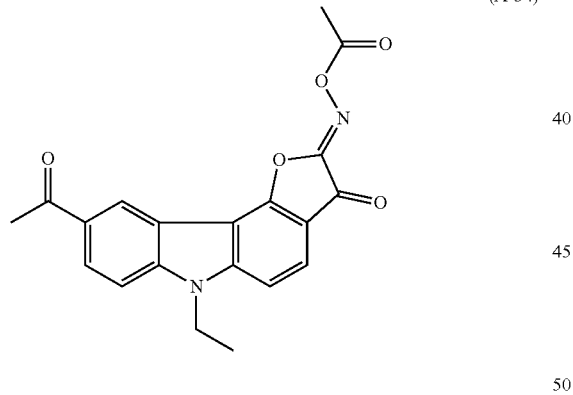
(A-35)
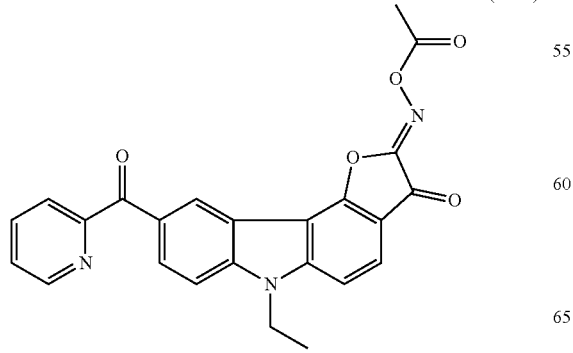
(A-36)
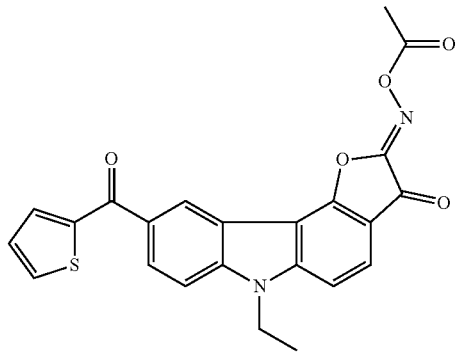
(A-37)
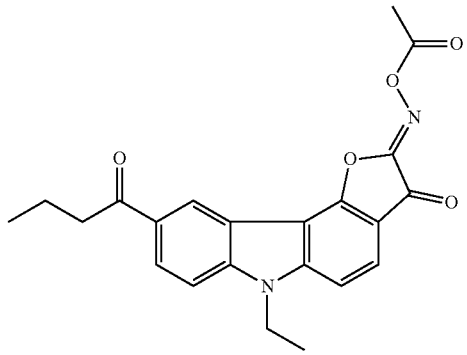
(A-38)
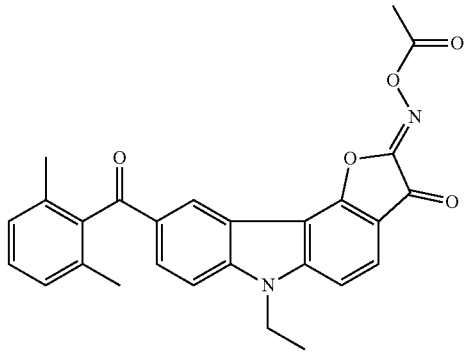
(A-39)
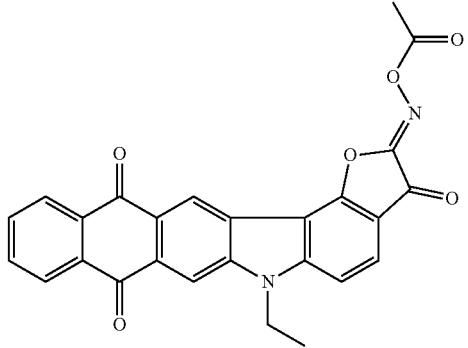

-continued
(A-40)
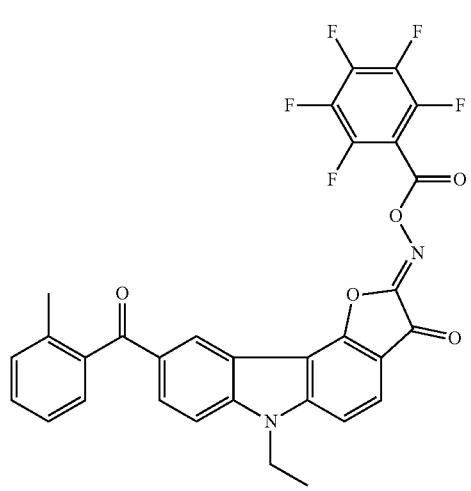
(A-41)
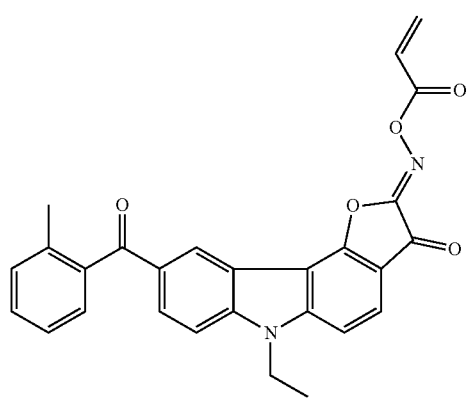
(A-42)
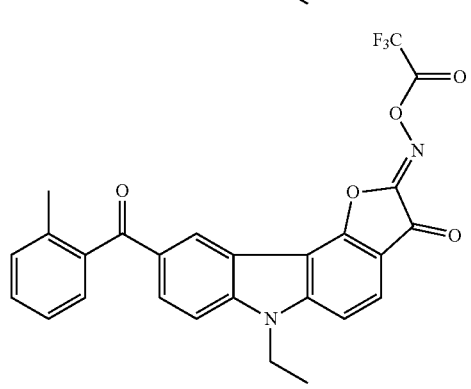
(A-43)
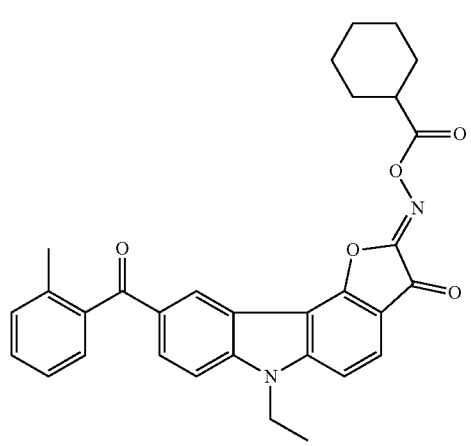
-continued
(A-44)
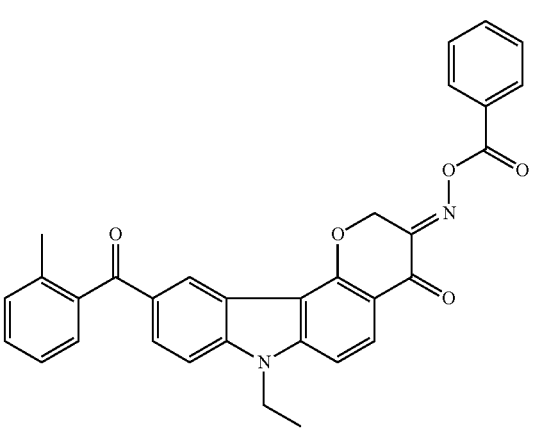
(A-45)
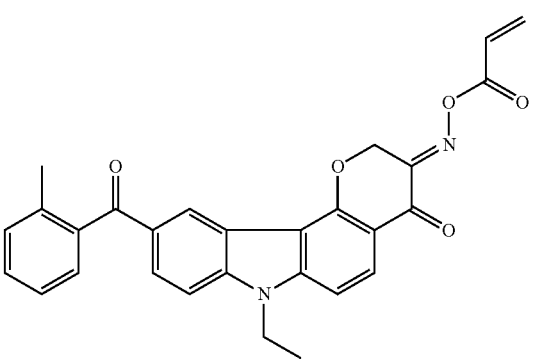
(A-46)
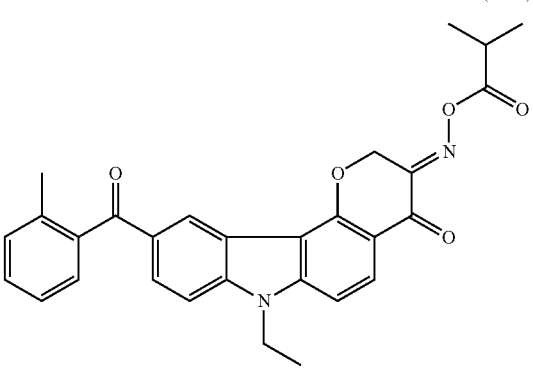
(A-47)
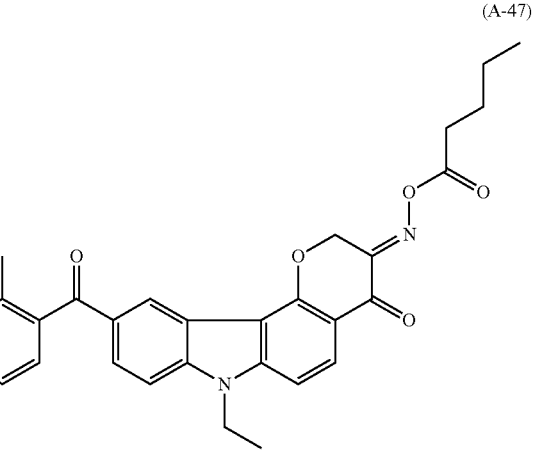

(A-48)
(A-49)
(A-50)
(A-51)
(A-52)
(A-53)
(A-54)
(A-55)
(A-56)
(A-57)

(A-58)
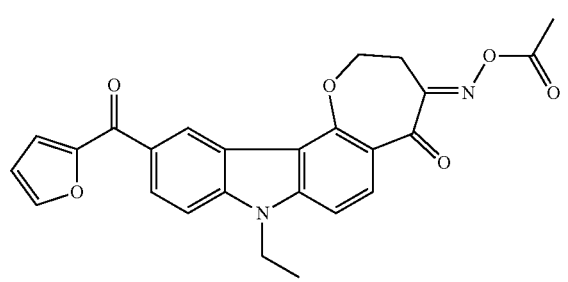
(A-59)
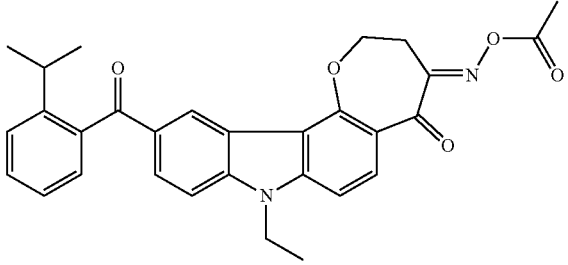
(A-60)
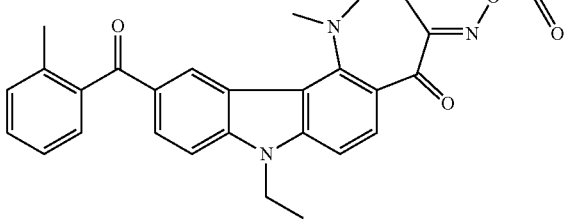
(A-61)
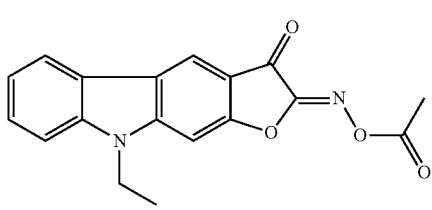
(A-62)
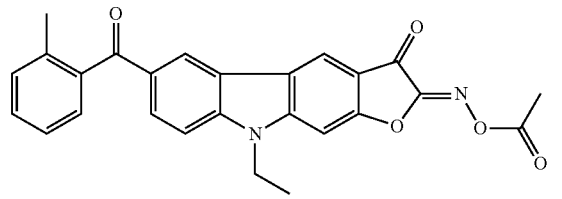
(A-63)
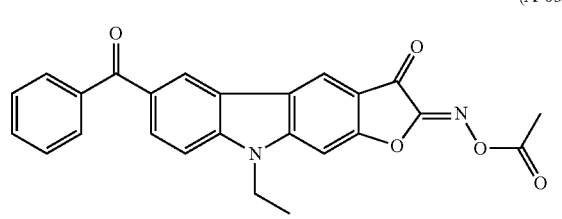
(A-64)
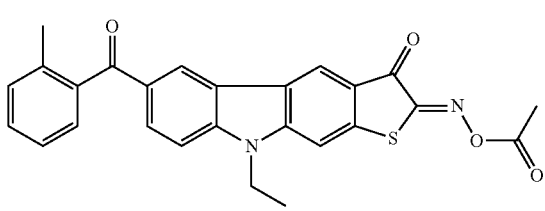
(A-65)
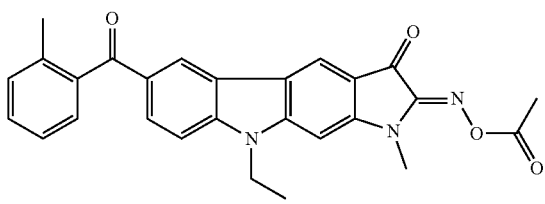
(A-66)
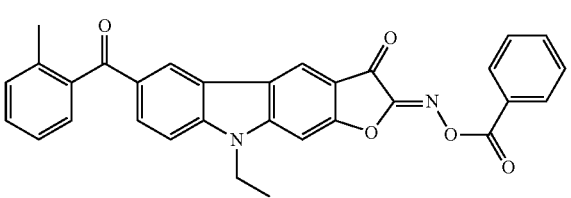
(A-67)
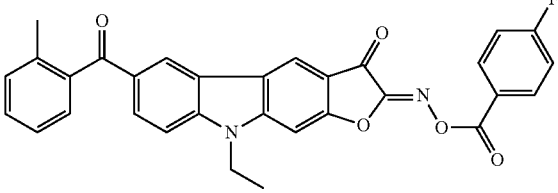
(A-68)
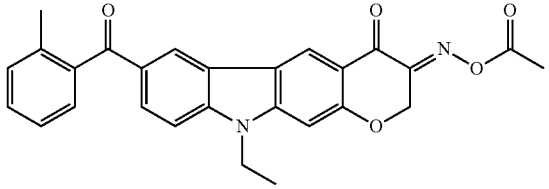
(A-69)
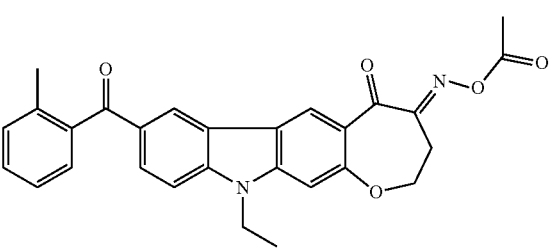

(A-70)
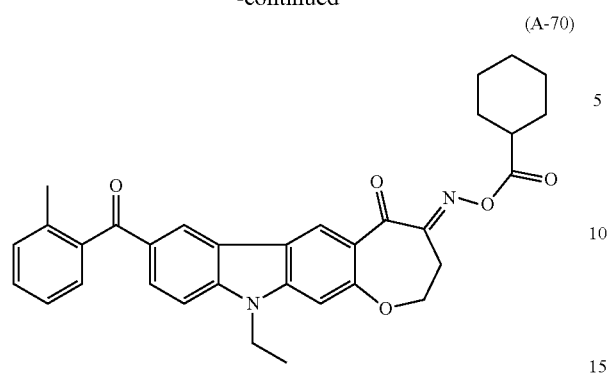
(A-71)
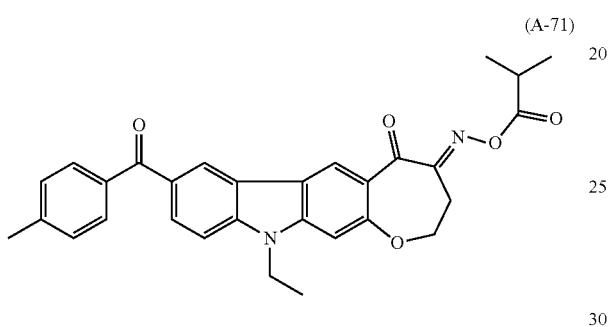
(A-72)
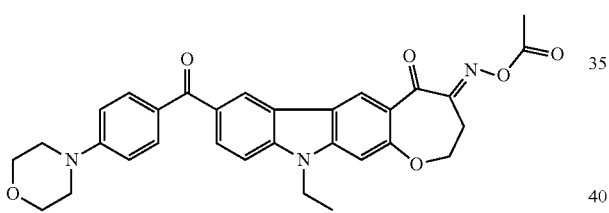
(A-73)
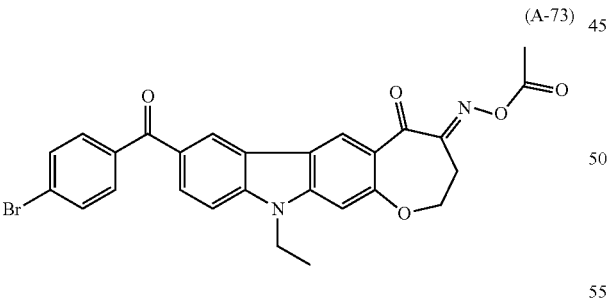
(A-74)
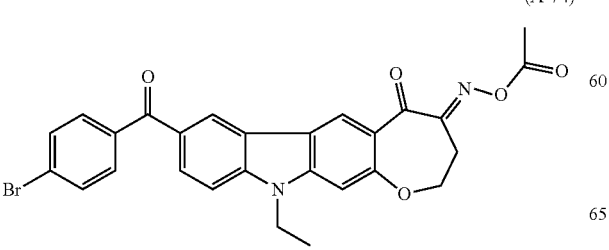
(A-75)
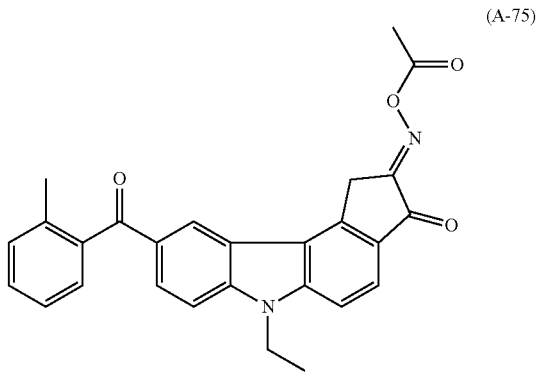
(A-76)
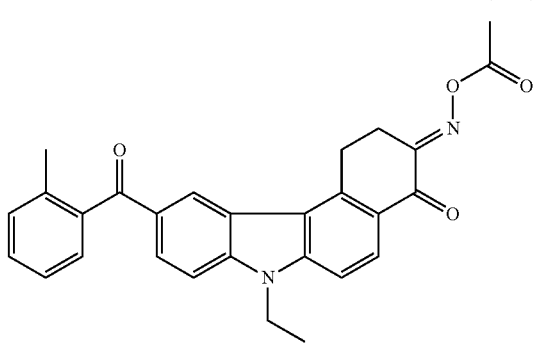
(A-77)
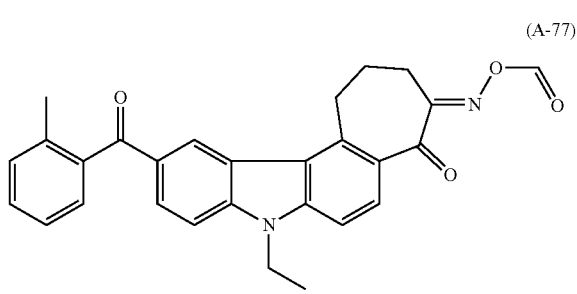
(A-78)
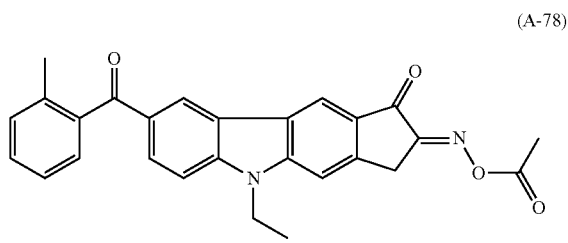
(A-79)
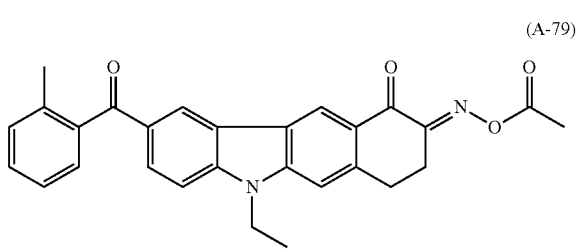 [SMILES: CCn1c2ccc(C(=O)c3ccccc3C)cc2c2cc3c(cc21)SC(C)/C(=N\OC(C)=O)C3=O]

-continued
(A-80)
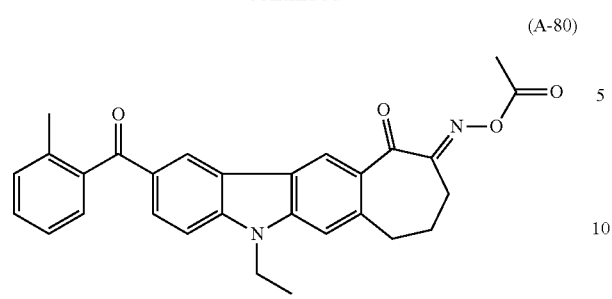
(A-81)
(A-82)
(A-83)
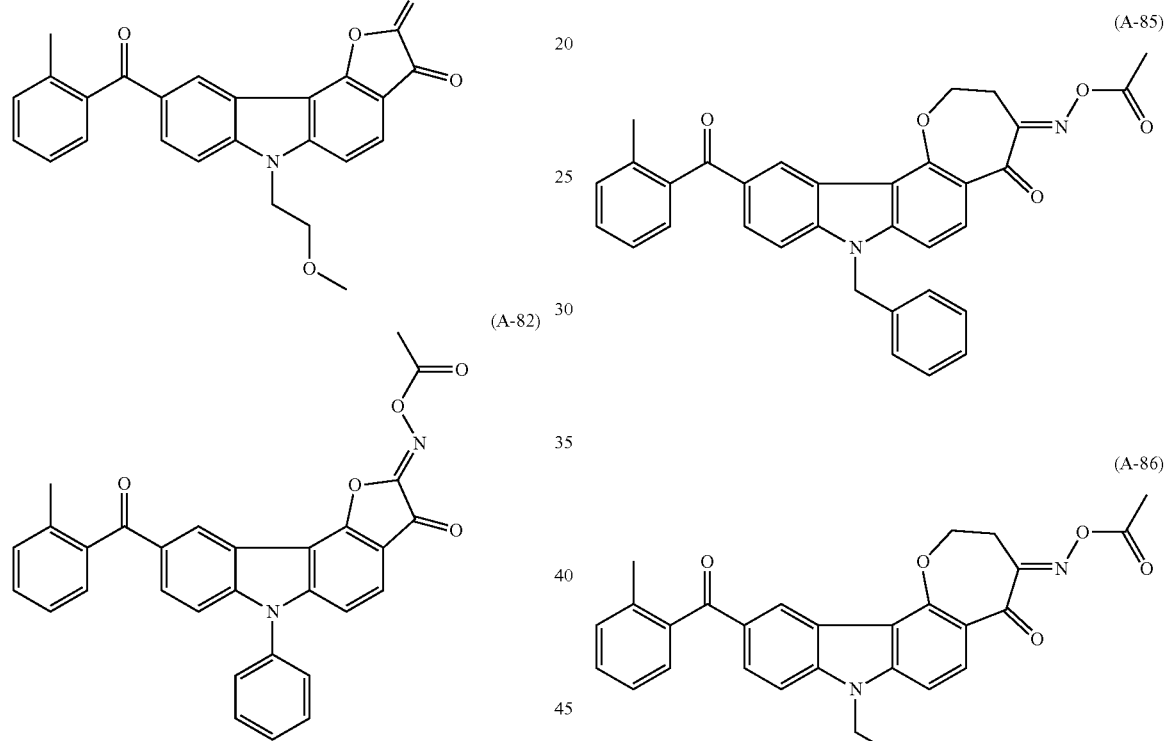
(A-84)
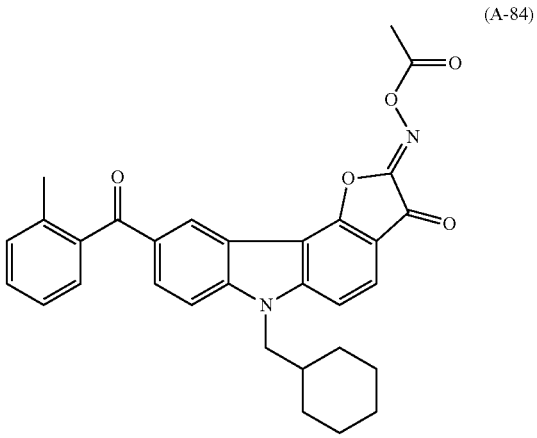
(A-85)
(A-86)
(A-87)
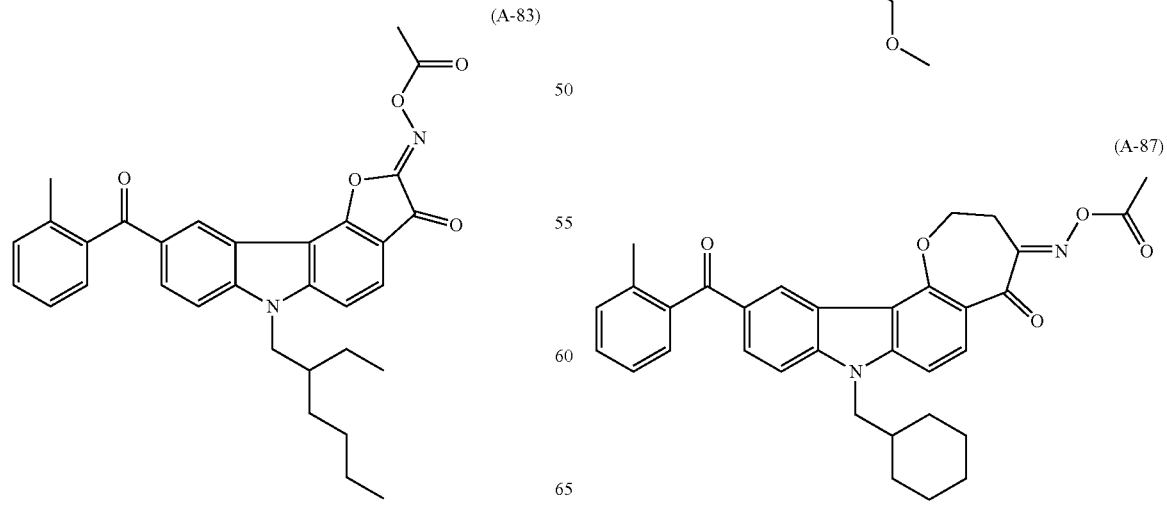

-continued
(A-88)
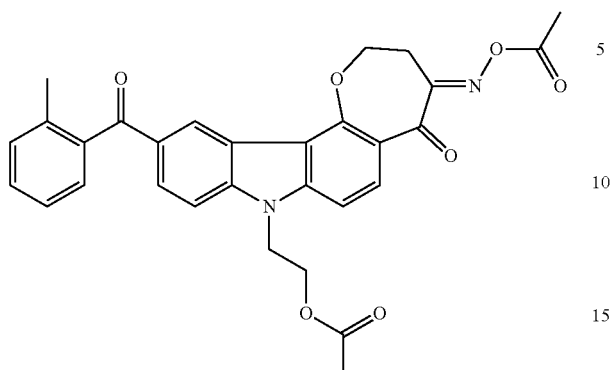
(A-89)
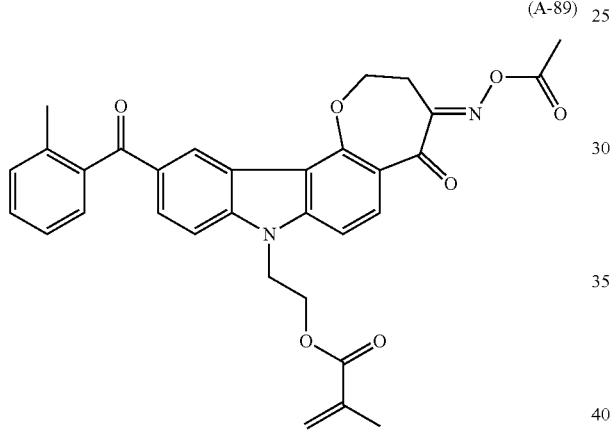
(A-90)
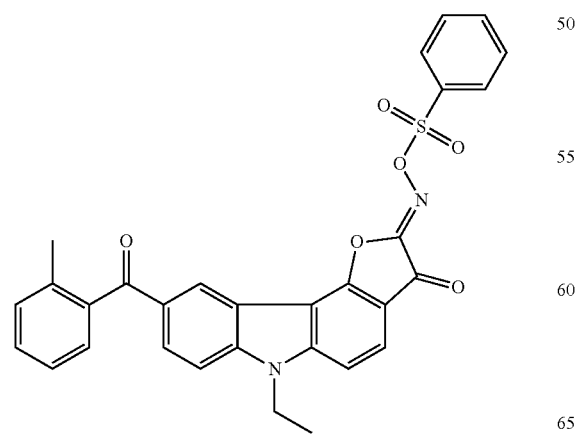
-continued
(A-91)
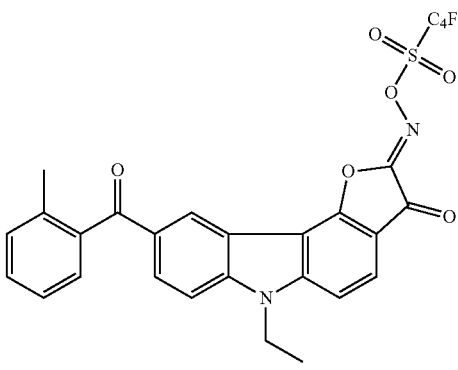
(A-92)
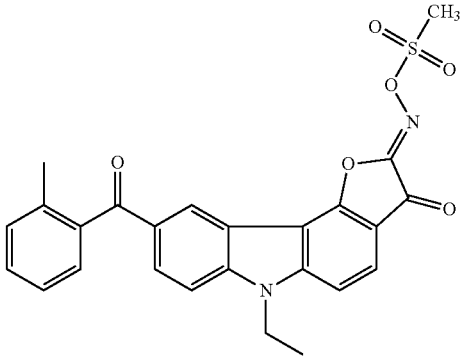
(A-93)
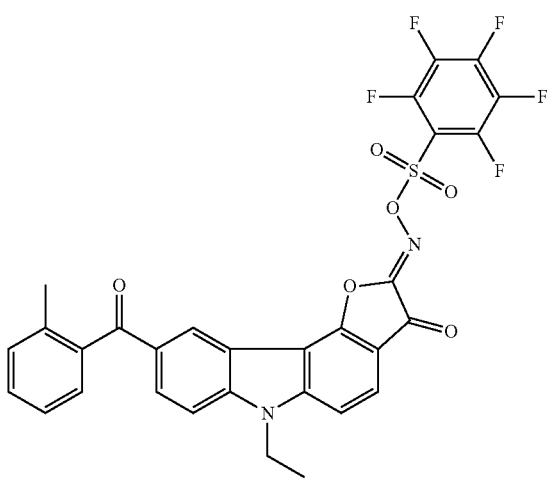
(A-94)
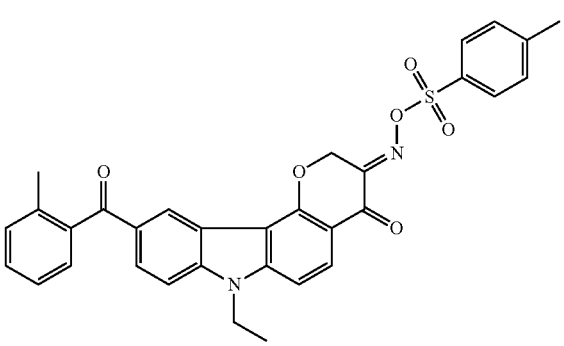

(A-95) 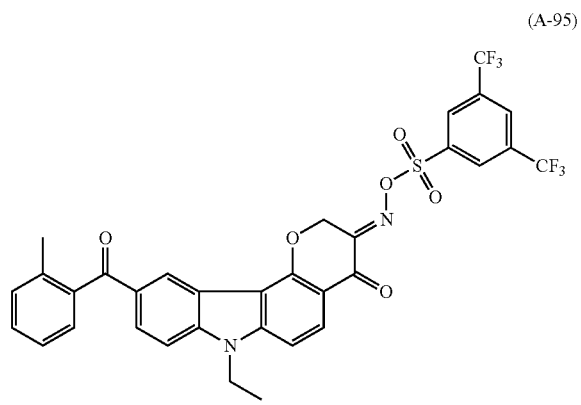
(A-96) 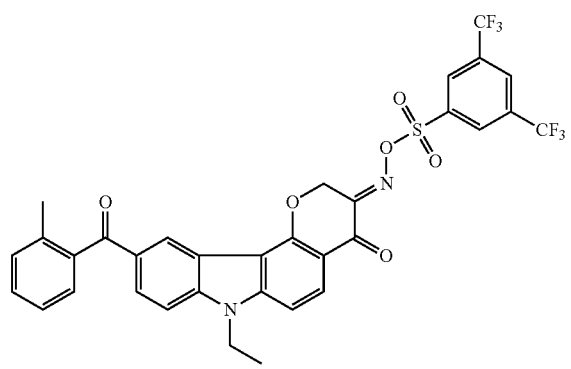
(A-97) 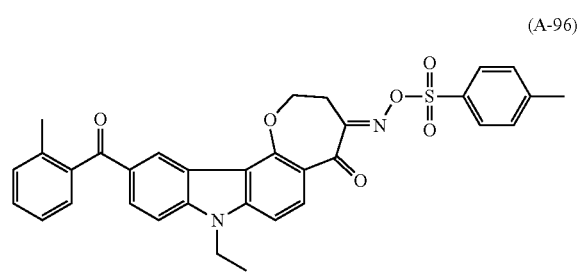
(A-98) 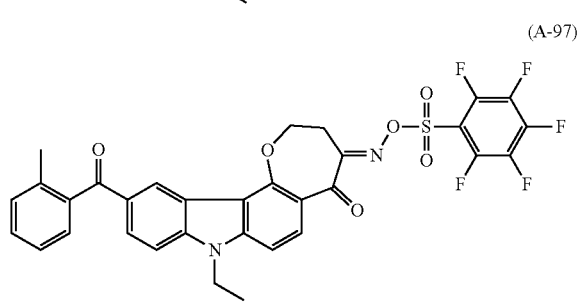
(A-99) 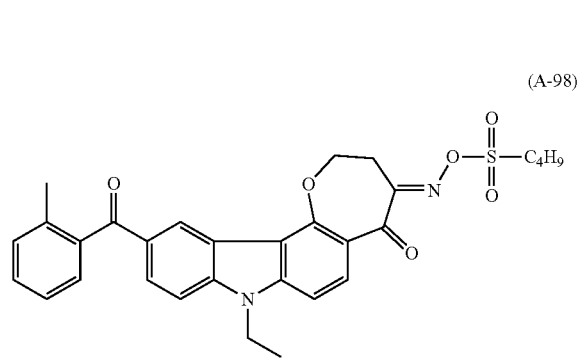
(A-100) 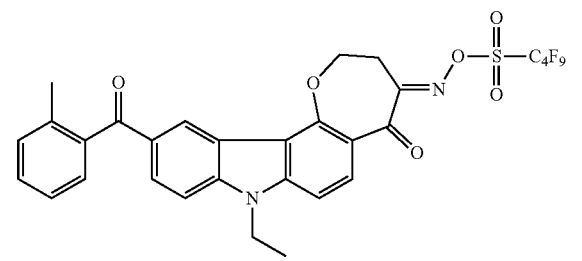
(A-101) 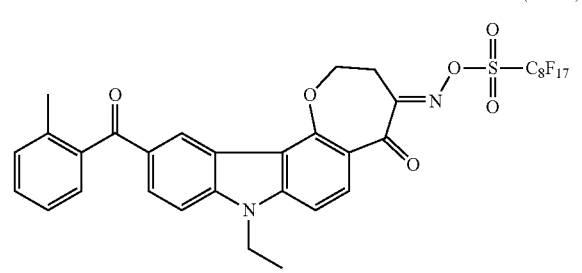
(A-102) 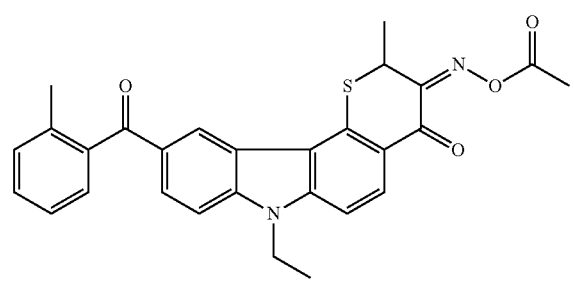
(A-103) 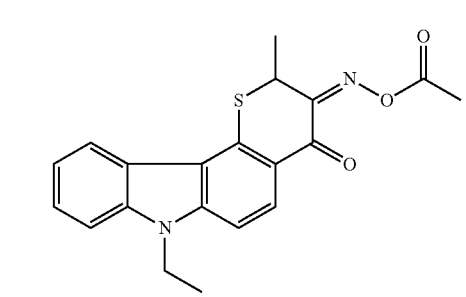
(A-104) 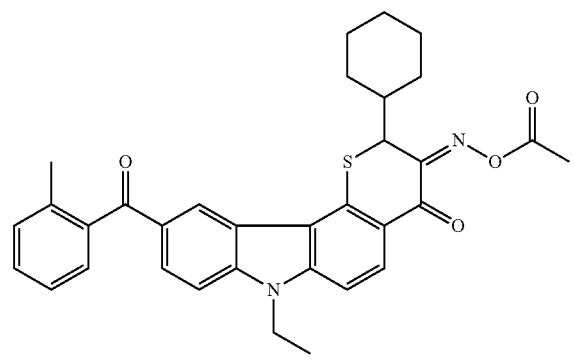

(A-105)

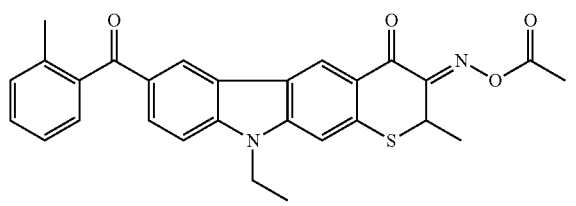

Of the above Exemplary Compounds (A-1) to (A-105), from the viewpoint of an increase in the molar extinction coefficient at 365 nm, Exemplary Compounds (A-1) to (A-18), (A-24) to (A-59), and (A-81) to (A-89) are preferable, and, Exemplary Compounds (A-1), (A-2), (A-3), (A-4), (A-8), (A-9), (A-10), (A-11), (A-15), (A-16), (A-17) and (A-18) are more preferable.

In addition, of the above Exemplary Compounds, Exemplary Compounds (A-1) to (A-18), (A-38) to (A-53), (A-57) to (A-59), (A-66) to (A-74), (A-83) to (A-87), (A-90) to (A-105) are novel compounds.

The specific oxime compound of the invention has the maximum absorption wavelength in the wavelength range of from 350 nm to 500 nm and has preferably the absorption wavelength in the wavelength range of from 360 nm to 480 nm. The specific oxime compound of the invention has a high absorbance particularly at 365 nm and 405 nm.

The molar extinction coefficient of the specific oxime compound mentioned above is 5,000 or more at 365 nm. Further, from the viewpoint of the sensitivity, the molar extinction coefficient at 365 nm or at 405 nm of the specific oxime compound is preferably from 5,000 to 300,000, more preferably from 10,000 to 300,000, and still more preferably from 20,000 to 200,000.

Thus, the specific oxime compound has an absorption in a longer wavelength range as compared with conventional oxime compounds. Accordingly, when the specific oxime compound is exposed with a light source at 365 nm and/or 405 nm, excellent sensitivity can be shown. Therefore, the polymerizable compound, which contains the specific oxime compound of the invention, is cured with high sensitivity.

The molar extinction coefficient of the specific oxime compound in this description refers to a value measured at a concentration of 0.01 g/L in an ethyl acetate solvent using an ultraviolet and visible spectrophotometer (CARRY-5 spectrophotometer; manufactured by Varian Inc.).

Of the specific oxime compounds according to the invention, for example, the oxime compounds represented by Formula (1) can be synthesized according to the scheme shown below, but the method is not construed as limiting to this method. X, Y and R³ in the following formula are as stated above.

In the following scheme, although the carboxylic acid that is a starting material may be a commercial product, when a suitable compound is not commercially available, the carboxylic acid can be easily synthesized by the Williamson ether synthesis of a heteroaryl compound and an ester halide, followed by hydrolysis by using sodium hydroxide and the like.

The acylation-cyclization by using an acid is completed by heating and stirring in methanesulfonic acid at 95° C. The cyclization efficiently proceeds, if the starting material is a 5-membered ring to a 7-membered ring. In the oximation, the cyclized product is allowed to react with a nitrite in the presence of a base at 0° C., thereby obtaining the oxime.

Further, the oxime is allowed to react with a carboxylic acid chloride or a sulfonic acid chloride in the presence of a base at 0° C. to room temperature, so that the corresponding oxime ester can be obtained. In addition, in the following scheme, X and R³ each have the same meanings as those in Formula (1) above and Y is a chlorine atom.

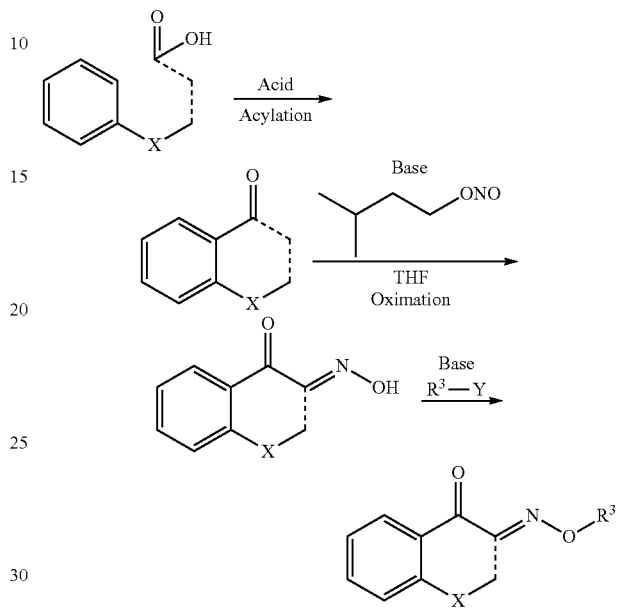

In addition to the polymerizable composition of the invention as stated above, the specific oxime compound of the invention is also applicable to the curable materials for the uses as described below by utilizing the photopolymerization initiation function of the compound.

Namely, for example, as illustrated below, examples of various uses include: printing ink materials (for example, use for the screen process printing ink, use for offset or flexographic printing ink, and use for UV curable ink); white or color finishing materials for lumber or metal, powder coating materials (particularly, use for materials for coating materials for paper, lumber, metal or plastic); marking materials for building marking or road marking; holographic recording materials, image recording materials, materials for a recording layer of a planographic printing plate precursor capable of being developed with an organic solvent or aqueous alkali, or sunlight curable materials for manufacturing screen printing mask, as photographic reproduction techniques; dental filling compositions, adhesives, pressure-sensitive adhesives, laminate resin materials, etching resist materials for both the liquid and dry thin-film; solder resist materials; electroplating materials; permanent resist materials; photoformable dielectric materials for printed circuit boards or electronic circuits; various display materials; optical switch materials, optical grid (interference grid) forming materials, optical circuit-manufacturing materials, three-dimensional article-manufacturing materials using bulk curing (UV-curing with transparent forming die) or stereolithographic techniques, (for example, materials recited in U.S. Pat. No. 4,575,330); composite materials (for example, styrene polyester which can contain glass fibers and/or other fibers and other auxiliaries, if needed) and other thick layer composition manufacturing materials; resist materials for coating or sealing electronic components and integrated circuits; optical fiber forming materials, coating materials for manufacturing optical lenses (for example, contact lenses or Fresnel lenses); materials for manufacturing medical devices, care aids or implants, and gel manufacturing materials having thermotropic properties as recited in German Patent No. 19,700,064 and European Patent No. 678,534.

Further, the specific oxime compound according to the invention functions as a radical initiator, for example, when the oxime ester comprises an acyl group, but, for example, when the oxime ester comprises a sulfonyl group, the specific oxime compound is also possible to generate an acid by being irradiated with an energy line, especially with light. Accordingly, the generated acid as a catalyst can be applied to other purposes, more specifically, by making the use of a coloring reaction of a dye precursor by using the generated acid as a catalyst, a material for image formation, forgery prevention, and energy radiation-dose detection, and further, by making the use of a decomposition reaction by using the generated acid as a catalyst, the specific oxime compound can also be utilized as a positive-working photoresist materials for semiconductor manufacture, TFT manufacture, color filter manufacture, micromachine component manufacture and the like.

As mentioned above, since the specific oxime compound according to the invention can be used as a photopolymerization initiator, it is preferable to use the specific oxime compound together with a polymerizable composition to apply the compound to a polymerizable compound (polymerizable composition of the invention) which can be polymerized and cured with light.

The photopolymerizable composition of the present invention is formed by including (A) the specific oxime compound and (B) a polymerizable compound, which will be described later. It is possible to form a cured film, which has high sensitivity to light having wavelengths of 365 nm and 405 nm, is excellent in storage stability, and is further possible to suppress coloration caused by heat-aging, by virtue of the function of (A) the specific oxime compound. Although the details of the mechanism are not clear, it is thought that since (A) the specific oxime compound absorbs light owing to the molecular structure thereof, and the recombination of radicals at the time of cleavage is suppressed, the quantity of the generated radicals is large, thereby achieving higher sensitivity. Further, since the radical recombination is suppressed, it is thought that the reaction among each of the decomposition products of the specific oxime compound at the time of heat-aging is suppressed, thereby suppressing the coloration resulting from the reaction.

That is, when the compound of the present invention having a carbonyl group at the α-position of an imino group is used, an imino radical resulting in coloration consecutively decomposes to nitrile, thereby suppressing the coloration after exposure. Further, since the decomposition efficiency of the imino radical is improved by cyclization, the recombination of the radicals with one another is efficiently suppressed, so that the coloration is effectively suppressed.

In the present invention, in order to evaluate the coloration due to heat-aging of the cured film formed from the polymerizable compound of the invention, the color difference ΔEab* can be used. Here, the color difference ΔEab* may be measured using MCPD-3000 manufactured by Otsuka Electronics Co., Ltd.

As the conditions in the evaluation, first, the polymerizable composition of the present invention is exposed to light at 385 nm with various exposure amounts in the range of from 10 mJ/cm$^2$ to 2,500 mJ/cm$^2$ by using an ultra high pressure mercury lamp proximity type exposure machine (manufactured by Hitachi High-Tech Electronics Engineering Co., Ltd.), or an i-line stepper exposure machine FPA-3000i5+ (manufactured by Canon Inc.) to form a cured film. Further, if needed, after developing, the cured film is heated at 200° C. for one hour.

The color difference ΔEab* of the cured film before and after the heating is measured, so that the change of the coloration state of the cured film due to heat-aging can be evaluated.

When the photopolymerizable composition of the present invention is used, the color difference ΔEab* before heating and after heating can be set to 5 or less.

Hereinafter, the photopolymerizable composition of the invention is explained in detail by reference to a polymerizable composition (1), which can be suitably used for forming colored areas and the like in a color filter (if needed, which may be referred to as a photopolymerizable composition for color filter hereinafter), and a polymerizable composition (2), which can be suitably used for forming a photosensitive layer and the like of a planographic printing plate precursor by way of example, but the uses of the photopolymerizable compositions of the invention are not limited to them, as described above.

Polymerizable composition (1): photopolymerizable composition for color filter

Since the photopolymerizable composition for a color filter is used for the purpose of forming a colored area used for the color filter, the composition includes (A) a specific oxime compound, (B) a polymerizable compound, and (C) a colorant. Hereinafter, each component that forms the photopolymerizable composition for a color filter is described.

(1)-(A) Specific Oxime Compound (A) the specific oxime compound contained in the polymerizable composition (1) functions as a polymerization initiator in the composition. The details of (A) the specific oxime compound are as stated above.

The content of the specific oxime compound in the a polymerizable composition (1) is preferably from 0.5 to 40% by mass, more preferably from 1 to 35% by mass, and sill more preferably from 1.5 to 30% by mass, relative to the total solid content of the composition.

The specific oxime compound may be used alone, or may used in combination of two or more kinds thereof.

Other Photopolymerization Initiators

In the polymerizable composition (1), a known photopolymerization initiator other than the specific oxime compound may be used together with the specific oxime compound to the extent that the effect of the invention is not impaired. In this case, the known photopolymerization initiator is preferably used in the range of 50% by mass or less relative to the specific oxime compound.

The photopolymerization initiator, which can be used together, is a compound that decomposes with light, and initiates and promotes polymerization of the polymerizable compound, which will be described later, and it is preferable that the photopolymerization initiator have an absorption in the range of the wavelengths of from 300 nm to 500 nm. Specifically, examples of the photopolymerization initiator include organic halide compounds, oxidiazole compounds, carbonyl compounds, ketal compounds, benzoin compounds, acridine compounds, organic peroxide compounds, azo compounds, coumarin compounds, azide compounds, metallocene compounds, biimidazole compounds, organic boric acid compounds, disulfonic acid compounds, oxime ester compounds, onium salt compounds, and acyl phosphine(oxide) compounds.

(1)-(B) Polymerizable Compound

A polymerizable compounds, which can be used for the polymerizable composition (1), is an addition-polymerizable compound having at least one ethylenic unsaturated double bond, and is selected from compounds having at least one at least one ethylenic unsaturated double bond at a terminal thereof, and preferably two more terminal unsaturated double bonds at terminals thereof. Such compounds are widely known in the art, and can be used in the invention without particular limitation. These compounds have chemical forms such as monomers or prepolymers, namely, dimers, trimers, and oligomers, or the mixtures thereof, and the copolymers thereof, for example. Examples of monomers or the copolymers thereof include unsaturated carboxylic acid (for example, acrylic acid, methacrylic acid, itaconic acid, crotonic acid, isocrotonic acid, maleic acid, and the like) and the esters and amides thereof, and esters of an unsaturated carboxylic acid and an aliphatic polyhydric alcohol compound and amides of an unsaturated carboxylic acid and an aliphatic polyvalent amine compound are preferably used. Further, addition reaction products of unsaturated carboxylic acid esters or amides, which have a nucleophilic substituent such as a hydroxyl group, an amino group or a mercapto group, with monofunctional or polyfunctional isocyanates or epoxys, and dehydration condensation products with monofunctional or polyfunctional carboxylic acids, are also preferably used. Moreover, the addition reaction products of unsaturated carboxylic acid esters or unsaturated carboxylic acid amides, which have an electrophilic substituent such as an isocyanate group or an epoxy group, with monofunctional or polyfunctional alcohols, amines or thiols; and further, substitution reaction products of unsaturated carboxyl acid esters or unsaturated carboxyl acid amides, which have a releasable substituent such as a halogen group or a tosyloxy group, with monofunctional or polyfunctional alcohols, amines or thiols; are also preferable. Furthermore, as another example, compounds, in which the unsaturated carboxylic acid is replaced by an unsaturated phosphonic acid, styrene, a vinyl ether or the like, can also be used.

Specific examples of the monomers of esters of aliphatic polyhydric alcohol compounds and unsaturated carboxylic acids include: acrylic esters such as ethylene glycol diacrylate, triethylene glycol diacrylate, 1,3-butanediol diacrylate, tetramethylene glycol diacrylate, propylene glycol diacrylate, neopentylglycol diacrylate, trimethylolpropane triacrylate, trimethylol propane-tri(acryloyloxypropyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl)isocyanurate, polyester acrylate oligomer and isocyanuric acid EO-modified triacrylate:

methacrylates such as tetramethylene glycol dimethacrylate, triethylene glycol dimethacrylate, neopentylglycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl]dimethylmethane, and bis-[p-(methacryloxyethoxy)phenyl]dimethylmethane;

itaconates such as ethylene glycol diitaconate, propylene glycol diitaconate, 1,3-butanediol diitaconate, 1,4-butanediol diitaconate, tetramethylene glycol diitaconate, pentaerythritol diitaconate, and sorbitol tetraitaconate;

crotonates such as ethylene glycol dicrotonate, tetramethylene glycol dicrotonate, pentaerythritol dicrotonate, and sorbitol tetradicrotonate;

isocrotonates such as ethylene glycol diisocrotonate, pentaerythritol diisocrotonate, and sorbitol tetraisocrotonate; and maleates such as ethylene glycol dimaleate, triethylene glycol dimaleate, pentaerythritol dimaleate, and sorbitol tetramaleate.

Preferable examples of other esters include aliphatic alcohol esters as recited in Japanese Examined Patent Application Publication (JP-B) No. 51-47334 and JP-A No. 57-196231; esters having an aromatic skeleton as recited in JP-A No. 59-5240, JP-A No. 59-5241 and JP-A No. 2-226149; and esters having an amino group as recited in JP-A No. 1-165613. The ester monomers as described above can be used as mixtures.

Further, specific examples of monomers of amides of an aliphatic polyvalent amine compound and an unsaturated carboxylic acid include methylenebis-acrylamide, methylenebis-methacrylamide, 1,6-hexamethylenebis-acrylamide, 1,6-hexamethylenebis-methacrylamide, diethylene triamine trisacrylamide, xylylenebisacrylamide, and xylylenebismethacrylamide.

Preferable examples of other desirable amide monomers include monomers having a cyclohexylene structure as recited in JP-B No. 54-21726.

Moreover, urethane addition-polymerizable compounds produced by using the addition reaction of an isocyanate and a hydroxyl group are also suitable, and specific examples of such compounds include vinyl urethane compounds containing two or more polymerizable vinyl groups in a molecule formed by adding a hydroxyl group-containing vinyl monomer represented by the following Formula (A) to a polyisocyanate compound having two or more isocyanate groups in a molecule as recited in JP-B No. 48-41708.

$$CH_2=C(R^4)COOCH_2CH(R^5)OH \qquad (A)$$

(here, $R^4$ and $R^5$ each represent H or $CH_3$ in Formula (A).)

Further, urethane acrylates as recited in JP-A No. 51-37193, JP-B No. 2-32293, and JP-B No. 2-16765, and urethane compounds having an ethylene oxide skeleton as recited in JP-B No. 58-49860, JP-B No. 56-17654, JP-B No. 62-39417, and JP-B No. 62-39418 are also preferable. Furthermore, by using addition-polymerizable compounds having an amino structure or a sulfide structure in a molecule as recited in JP-A No. 63-277653, JP-A No. 63-260909 and JP-A No. 1-105238, a photopolymerizable composition having extremely high photosensitive speed can be obtained.

Other examples include polyfunctional acrylates or methacrylates such as polyester acrylates as recited in JP-A No. 48-64183, JP-B No. 49-43191 and JP-B No. 52-30490, and epoxyacrylates formed by reacting an epoxy resin with (meth)acrylic acid. Further, other examples include certain unsaturated compounds as recited in JP-B No. 46-43946, JP-B No. 1-40337, and JP-B No. 1-40336, and vinyl sulfonic acid compounds as recited in JP-A No. 2-25493. Moreover, in some cases, a structure containing a perfluoroalkyl group as recited in JP-A No. 61-22048 may preferably be used. In addition, photocurable monomers and oligomers as recited in Journal of the Adhesion Society of Japan, Vol. 20, No. 7, pp. 300-308 can also be used.

Details of the method of the uses of the addition-polymerizable compounds, such as the structure thereof, the single use or combined use, or the addition amount of the compound, can be arbitrarily determined in accordance with the aimed design of the performance of the photopolymerizable composition. For example, the composition is selected from the following point of view.

In view of the sensitivity, the structure having a high content of unsaturated groups per one molecule is desirable, and in many cases, a bifunctional or higher functional structure is desirable. Further, in order to make the strength of a cured film high, a trifunctional or higher functional structure is preferable. Furthermore, a method of controlling both the sensitivity and the strength is also effective by using compounds having different functionalities and/or different polymerizable groups (for example, an acrylic ester, a methacrylic ester, a styrene compound, and a vinyl ether compound) in combination.

Moreover, in view of the compatibility with other components (for example, a photopolymerization initiator, a colorant (a pigment or a dye) and the like, and binder polymer and the like) and the dispersibility, the selection of addition polymerizable compounds and the use method are important factors, and, for example, in some cases, the compatibility may be enhanced by using a low purity compound or using in combination of two or more kinds of compounds. Further, for the purpose of increasing the adhesion to a hard surface of a support and the like, a compound having a specific structure may be selected.

The content of the polymerizable compound in the polymerizable composition (1) is preferably from 0.1 to 30% by mass, more preferably from 0.2 to 20% by mass, and still preferably from 0.3 to 15% by mass, relative to the total solid content of the composition.

The polymerizable compound may be used singly or may used in combination of two or more kinds.

(1)-(C) Colorant

The polymerizable composition (1) may include (C) the colorant. By containing a colorant, the colored polymerizable composition of a desired color can be obtained.

In addition, since the polymerizable composition (1) contains the specific oxime compound that is (A) the polymerization initiator of the invention having high sensitivity to a light source having wavelengths of 365 nm and 405 nm as a short wavelength light source, the colored polymerizable composition can be cured at high sensitivity even when the colorant is contained at high concentration.

The colorant used in the polymerizable composition (1) is not particularly restricted to, but one kind of conventionally known various dyes or pigments can be used alone, or a combination of two or more kinds thereof may be used, and the colorant is suitably selected in accordance with the intended use of the photopolymerizable composition. In the case where the photopolymerizable composition of the invention is used for manufacturing a color filter, any of the colorants (chromatic colorant) of the chromatic color system such as R, G, B or the like, which form color pixels of the color filter, and the colorant (black colorant) of the black system generally used for black matrix formation, can be used.

Since the photopolymerizable composition of the invention containing (A) the specific oxime compound can be cured even when the light quantity for exposure is small, the photopolymerizable composition can be particularly preferably used for a photopolymerizable composition containing a black colorant, through which light is hardly transmitted.

Hereinafter, the colorant applicable to the polymerizable composition (1) is explained by reference to a colorant suitable for the use of a color filter by way of examples.

As the chromatic color pigment, various kinds of conventionally known inorganic pigments or organic pigments can be used. Further, considering that the pigment has preferably high transmittance regardless of inorganic pigments or organic pigments, it is preferable that pigment particles having a small particle size as fine as possible be used, and taking into account of handling property, the average primary particle diameter of the pigment is preferably from 0.01 μm to 0.1 μm, and more preferably from 0.01 μm to 0.05 μm.

Examples of the inorganic pigments include metal compounds such as metal oxides or metal complexes, and specific examples thereof include metal oxides of iron, cobalt, aluminum, cadmium, lead, copper, titanium, magnesium, chromium, zinc, antimony, or the like and composite oxides of these metals.

In the invention, in particular, pigments having a basic nitrogen atom in the structural formula of the pigments can preferably be used. The pigments having a basic nitrogen atom exhibit good dispersibility in the polymerizable composition (1). Although the reason is not sufficiently clarified, it can be presumed that good affinity of the photosensitive polymerizable component and the pigment has an influence on the reason.

Examples of pigments which can be preferably used in the invention include the following pigments. However, the invention is not limited to these examples.

C.I. Pigment Yellow 11, 24, 108, 109, 110, 138, 139, 150, 151, 154, 167, 180, and 185;

C. I. Pigment Orange 36 and 71;

C. I. Pigment Red 122, 150, 171, 175, 177, 209, 224, 242, 254, 255, and 264;

C.I. Pigment Violet 19, 23, and 32;

C.I. Pigment Blue 15:1, 15:3, 15:6, 16, 22, 60, and 66; and

C.I. Pigment Black 1.

These organic pigments can be used alone, or in combination of various kinds of pigments for the purpose of increasing the color purity.

Further, as a pigment for a black matrix, carbon black, titanium black, iron oxide, and titanium oxide are used singly or mixtures thereof are used, and the combination of carbon black and titanium black is desirable. The mass ratio of carbon black and titanium black is preferably in the range of from 100:0 to 100:60, from the viewpoint of dispersion stability.

Titanium black can also be used as a pigment for a black matrix. A titanium black dispersion is explained in full detail hereinbelow.

The titanium black dispersion refers to a dispersion in which titanium black is contained as a colorant.

When the polymerizable dispersion contains titanium black as a titanium black dispersion, which is beforehand prepared, the dispersibility of titanium black and dispersion stability can be improved.

Hereafter, the titanium black is explained.

Titanium Black

The titanium black which can be used in the invention is black particles having a titanium atom, and is preferably low-order titanium oxide, titanium oxynitride or the like. The surface of the titanium black particles may be modified in accordance with the intended use such as improvement of dispersibility, suppression of coalescence or the like. The surface may be covered with silicon oxide, titanium oxide, germanium oxide, aluminum oxide, magnesium oxide, or zirconium oxide, and, alternatively, may be subjected to a treatment with a water-repellent substance as described in JP-A No. 2007-302836.

The particle diameter of titanium black particles is not specifically restricted to, but from the viewpoint of the dispersibility and coloration, the particle diameter is preferably from 3 to 2,000 nm, more preferably from 10 to 500 nm, and still preferably from 20 to 200 nm.

The specific surface area of titanium black is not specifically restricted to, but, usually, the specific surface area measured by a BET method is preferably from about 5 to 150 m²/g, and more preferably from about 20 to 100 m²/g, since the water repellency after such titanium black is subjected to a surface treatment becomes predetermined capability.

Examples of commercial products of titanium black of the invention include, but are not limited to, titanium black 10S, 12S, 13R, 13M, 13 M-C, 13R, and 13R-N (manufactured by Mitsubishi Materials Corporation) and TILACK D (manufactured by Ako Kasei Co., Ltd.).

In the polymerizable composition (1), when the colorant is a dye, a colored composition in the state where the dye is uniformly dissolved in the composition can be obtained.

As the colorants which can be used in the polymerizable composition (1), known dyes which are conventionally used for color filters can be used without particular limitation. Examples of the dyes include pyrazoleazo dyes, anilinoazo dyes, triphenylmethane dyes, anthraquinone dyes, anthrapyridone dyes, benzylidene dyes, oxonole dyes, pyrazolotriazole dyes, pyridoneazo dyes, cyanine dyes, phenothiazine dyes, pyrrolopyrazol azomethine dyes, xanthene dyes, phthalocyanine dyes, benzopyrane dyes, and indigo dyes.

In the case of a resist system in which development is performed using water or alkali, an acid dye and/or a derivative thereof may suitably be used from the viewpoint of completely removing a binder and/or a dye in the unexposed area remaining after the development.

In addition, direct dyes, basic dyes, mordant dyes, acid mordant dyes, azoic dyes, disperse dyes, oil-soluble dyes, edible dyes, and/or the derivatives thereof can usefully be used.

The acid dyes are not specifically limited to, as long as the dyes have an acidic group such as a sulfonic acid group or a carboxyl acid group, but are selected in view of all the required capabilities such as the solubility in an organic solvent or a developer, the salt-forming property with a basic compound, the light absorbance, the interaction with other components in the composition, the light fastness, the heat resistance, or the like.

Specific examples of acid dyes are listed below.

Examples include dyes such as Acid Black 24; Acid Blue 23, 25, 29, 62, 80, 86, 87, 92, 138, 158, 182, 243, 324:1; Acid Orange 8, 51, 56, 63, 74; Acid Red 1, 4, 8, 34, 37, 42, 52, 57, 80, 97, 114, 143, 145, 151, 183, 217; Acid Violet 7; Acid Yellow 17, 25, 29, 34, 42, 72, 76, 99, 111, 112, 114, 116, 184, 243; Acid Green 25, and the derivative of these dyes.

Further, the acid dyes of azo dyes, xanthene dyes, and phthalocyanine dyes other than the above, and, for example, the acid dyes such as C.I. Solvent Blue 44 and 38; C.I. Solvent Orange 45; Rhodamine B, Rhodamine 110 and the like, and the derivatives of these dyes are also preferably be used.

Among them, it is preferable that the colorant be a colorant selected from triallyl methane dyes, anthraquinone dyes, azomethine dyes, benzylidene dyes, oxonole dyes, cyanine dyes, phenothiazine dyes, pyrrolopyrazol azomethine dyes, xanthene dyes, phthalocyanine dyes, benzopyrane dyes, indigo dyes, pyrazoleazo dyes, anilinoazo dyes, pyrazolotriazole dyes, pyridoneazo dyes, and anthrapyridone dyes.

The colorants which can be used in the polymerizable composition (1) are preferably dyes or pigments. In particular, it is desirable that a pigment satisfy an average particle diameter (r): 20 nm≤r≤300 nm, preferably 25 nm≤r≤250 nm, and particularly preferably 30 nm≤r≤200 nm. By using a pigment having such an average particle diameter (r), red and green pixels having a high contrast ratio and a high light transmittance can be obtained. The "average particle diameter" herein means the average particle diameter of secondary particles, in which primary particles (single crystallite) of the pigment, are aggregated.

Further, in the particle diameter distribution of secondary particles of pigment that can be used in the invention (hereinafter, simply refers to as "particle diameter distribution"), it is preferable that the secondary particles within the range of (average particle diameter±100) nm be preferably 70% by mass or more, and more preferably 80% by mass or more, with respect to the total mass.

The pigment having the average particle diameter and the particle diameter distribution may be prepared by pulverizing a commercially available pigment while mixing and dispersing it with, as required, other pigments (having an average particle diameter usually exceeding 300 nm), preferably as a pigment mixture mixed with a dispersant and a solvent, by using, for example, a grinder such as a bead mill or a roll mill. The pigment obtained in this way usually has the form of a pigment dispersion.

The content of the colorant contained in the polymerizable composition (1) is preferably from 30% by mass to 95% by mass, more preferably from 40% by mass to 90% by mass, and still more preferably from 50% by mass to 80% by mass, in the total solid content of the photopolymerizable composition.

By setting the content of the colorant within the above range, suitable chromaticity can be obtained when a color filter is manufactured by using the polymerizable composition (1). Further, since photocuring can sufficiently proceed and the strength as a film can be maintained, it is possible to prevent the development latitude from being narrow in the case of alkali development.

That is, since (A) the specific oxime compound, which is the polymerization initiator in the invention, has high light absorption efficiency, (A) the specific oxime compound can be polymerized and cured with high sensitivity, and improvement effect on the sensitivity is notably exerted as compared with the case where other polymerization initiators are used, even when a colorant is contained in the photopolymerizable composition at high concentration.

(1)-(D) Pigment Dispersant

When the polymerizable composition (1) contains a pigment such as titanium black or an organic pigment as (C) a colorant, it is desirable to further add (D) a pigment dispersant from the viewpoint of improving the dispersibility of the pigment.

Examples of the pigment dispersant that can be used in the invention include a polymeric dispersant (for example, a polyamide amine and a salt thereof, a polycarboxylic acid and a salt thereof, a high molecular weight unsaturated acid ester, a modified polyurethane, a modified polyester, a modified poly(meth)acrylate, a (meth)acrylic copolymer, and naphthalenesulfonic acid-formalin condensate) and a polyoxyethylene alkylphosphate, a polyoxyethylene alkylamine, an alkanolamine, and pigment derivatives.

The polymeric dispersant can be further classified into a straight-chained polymer, a terminal modified polymer, a graft polymer, and a block polymer based on the structure of the dispersant.

The polymeric dispersant adheres to the surface of a pigment, and functions so as to prevent re-aggregation. Accordingly, preferable examples of the structures include a terminal modified polymer, a graft polymer, and a block polymer, which have an anchor moiety to the pigment surface.

On the other hand, pigment derivatives have an effect of promoting the adsorption of the polymeric dispersant by modifying the pigment surface.

Specific examples of the dispersant that can be used in the invention include "DISPERBYK-101 (polyamideamine phosphate), 107 (carboxylic ester), 110 (copolymer containing an acid group), 130 (polyamide), 161, 162, 163, 164, 165, 166, and 170 (high molecular copolymer)", "BYK-P104 and P105 (high molecular weight unsaturated polycarboxylic acid)" manufactured by BYK-Chemie GmbH; "EFKA 4047, 4050, 4010, and 4165 (polyurethanes)", and "EFKA4330, and 4340 (block copolymers), 4400, and 4402 (modified acrylic resins), 5010 (polyester amide), 5765 (high molecular weight polycarboxylic acid salt), 6220 (fatty acid polyester), 6745 (phthalocyanine derivative), 6750 (azo pigment derivative)" manufactured by EFKA Chemicals B.V.; "AJISPER PB821, and PB822" manufactured by Ajinomoto Fine Techno Co., Inc.; "FLOWLEN TG-710 (urethane oligomer)", "POLYFLOW No. 50E, No. 300 (acrylic copolymer)" manufactured by Kyoeisha Chemical Co., Ltd.; "DISPARLON KS-860, 873SN, 874, and #2150 (aliphatic polyvalent carboxylic acid), #7004 (polyether ester), DA-703-50, DA-705, and DA-725", manufactured by Kusumoto Chemicals Ltd.; "DEMOR RN, N (naphthalenesulfonic acid-formalin polycondensate), MS, C, and SN-B (aromatic sulfonic acid-formalin polycondensate)", "HOMOGENOL L-18 (polymeric polycarboxylic acid)", "EMULGEN 920, 930, 935, and 985 (polyoxyethylene nonylphenyl ether)", "ACETAMINE 86 (stearylamine acetate)" manufactured by Kao Corporation; "SOLSPERSE 5000 (phthalocyanine derivative), 22000 (azo pigment derivative), 13240 (polyester amine), 3000, 17000, and 27000 (polymer having a functional moiety at a terminal portion thereof), 24000, 28000, 32000, and 38500 (graft type polymer)", manufactured by Lubrizol Corporation; and "NIKKOL T106 (polyoxyethylene sorbitan monooleate) and MYS-IEX (polyoxyethylene monostealate)" manufactured by Nikko Chemicals Co., Ltd.

These dispersants may be used alone, or may be used in combination of two or more kinds. In the invention, it is particularly preferable to use a pigment derivative and a polymeric dispersant in combination.

The content of (D) the dispersant in the polymerizable composition (1) is preferably from 1 to 80 parts by mass, more preferably from 5 to 70 parts by mass, and still more preferably from 10 to 60 parts by mass, relative to 100 parts by mass of a pigment as (C) the colorant.

Specifically, when a polymeric dispersant is used, the use amount of the polymeric dispersant is preferably in the range of from 5 to 100 parts, and more preferably in the range of from 10 to 80 parts in terms of mass, relative to 100 parts by mass of the pigment.

Further, when a pigment derivative is used together with the polymeric dispersant, the use amount of the pigment derivative is preferably in the range of from 1 to 30 parts, more preferably in the range of from 3 to 20 parts, and still more preferably in the range of from 5 to 15 parts in terms of mass, relative to 100 parts by mass of the pigment.

When the pigment as (C) a colorant is used in the polymerizable composition (1), and (D) a dispersant is further used, the total sum of the contents of the colorant and the dispersant is preferably from 30% by mass to 90% by mass, more preferably from 40% by mass to 85% by mass, and still more preferably from 50% by mass to 80% by mass, relative to the total solid contents which forms the polymerizable composition.

If needed, the polymerizable composition (1) may further contain an arbitrary component, which will be explained in detail, unless the effect of the invention is impaired.

Hereafter, the arbitrary component, which may be contained in the polymerizable (1), is explained.

(1): Sensitizer

A sensitizer may be contained in the polymerizable composition (1) in order to improve the radical generation efficiency of a radical initiator, and to achieve a longer photosensitive wavelength.

As the sensitizer, which can be used in the invention, a sensitizer that sensitizes the polymerization initiator by way of an electron transfer mechanism or energy transfer mechanism is preferred.

Examples of the sensitizer, which may be used in the polymerizable composition (1), include the compounds which are described below, and those have an absorption wavelength in a wavelength region of 300 nm to 450 nm.

Examples of the sensitizer include polycyclic aromatics (for example, phenanthrene, anthracene, pyrene, perylene, triphenylene, 9,10-dialkoxyanthracene), xanthenes (for example, fluorescein, eosine, erythrosine, Rhodamine B, rose bengal), thioxanthones (isopropylthioxanthone, diethylthioxanthone, chlorothioxanthone), cyanines (for example, thiacarbocyanine, oxacarbocyanine), merocyanines (for example, merocyanine, carbomerocyanine), phthalocyanines, thiazines (for example, thionine, methylene blue, toluidine blue), acridines (for example, acridine orange, chloroflavin, acriflavine), anthraquinones (for example, anthraquinone), squaryliums (for example, squarylium), acridine orange, coumarins (for example, 7-diethylamino-4-methylcoumarin), ketocoumarin, phenothiazines, phenazines, styryl benzenes, azo compounds, diphenyl methane, triphenyl methane, distyryl benzenes, carbazoles, porphyrin, spiro compounds, quinacridone, indigo, styryl compounds, pyrylium compounds, pyromentene compounds, pyrazolotriazole compounds, benzothiazole compounds, barbituric acid derivatives, thiobarbituric acid derivatives, aromatic ketone compounds such as acetophenone, benzophenone, thioxanthone, Michler's ketone, and heterocyclic compounds such as N-aryloxazilidinone or the like.

More desirable examples of the sensitizer in a polymerizable composition (1) include the compounds represented by the following Formula (e-1):

(e-1)

In Formula (e-1), $A^1$ represents a sulfur atom or $NR^{50}$, and $R^{50}$ represents an alkyl group or an aryl group; $L^1$ represents a nonmetal atomic group that forms a basic nucleus of a dye together with $A^1$ and carbon atoms adjacent to $L^1$; $R^{51}$ and $R^{52}$ each independently represent a hydrogen atom or a monovalent nonmetal atomic group, and $R^{51}$ and $R^{52}$ may be combined with each other to form an acidic nucleus of the dye; and W represents an oxygen atom or a sulfur atom.

Further, examples of preferable sensitizers, which may be contained in the polymerizable composition (1), include at least one kind of the compounds selected from the compounds represented by the following Formula (II) and the Formula (III), which will be described later, in addition to the sensitizes mentioned above.

These may be used alone, or may be used in combination of two or more kinds

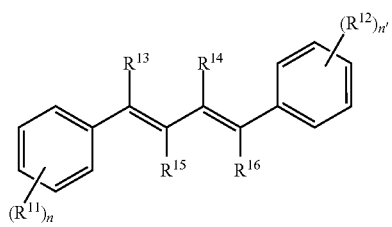

(II)

In Formula (II), $R^{11}$ and $R^{12}$ each independently represent a monovalent substituent; $R^{13}$, $R^{14}$, $R^{15}$, and $R^{16}$ each independently represent a hydrogen atom or a monovalent substituent; and n represents an integer of 0 to 5, n' represents an integer of 0 to 5, and both of n and n' do not represent 0 at the same time. When n is two or more, plural $R^{11}$(s) may be the same as, or may be different from one another. When n' is two or more, plural $R^{12}$(s) may be the same as, or may be different from one another. In addition, in Formula (II), isomers resulting from the double bond are not limited to either one of the isomers.

Preferable examples of the compounds represented by Formula (II) are listed below.

In addition, in this description, chemical formulae may be shown by simplified constitutional formulae, and the solid lines represent hydrocarbon groups, unless otherwise elements or substituents are specifically indicated.

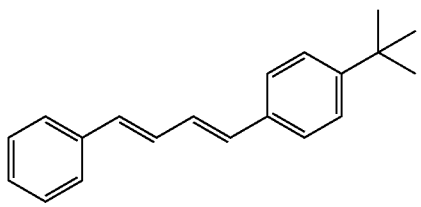

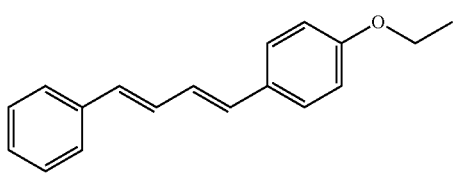

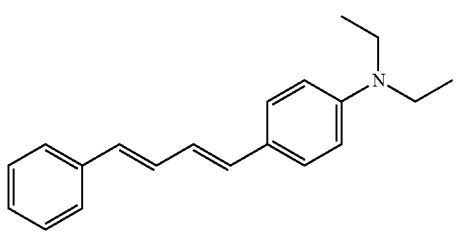

-continued

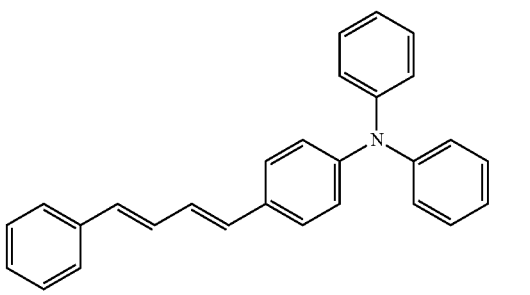

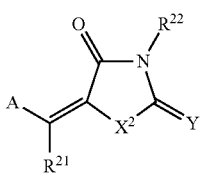

(III)

In Formula (III), A represents an aromatic ring which may have a substituent or a heterocyclic ring which may have a substituent; $X^2$ represents an oxygen atom, a sulfur atom, or —N($R^{23}$)—; Y represents an oxygen atom, a sulfur atom, or —N($R^{23}$)—; $R^{21}$, $R^{22}$, and $R^{23}$ each independently represent a hydrogen atom or a monovalent nonmetal atomic group; and A, $R^{21}$, $R^{22}$, and $R^{23}$ may be combined with each other to form an aliphatic or aromatic ring.

In Formula (III), $R^{21}$, $R^{22}$, and $R^{23}$ each independently represent a hydrogen atom or a monovalent nonmetal atomic group. When $R^{21}$, $R^{22}$, and $R^{23}$ represents a monovalent nonmetal atom, $R^{21}$, $R^{22}$, and $R^{23}$ preferably represents an unsubstituted or substituted alkyl group, an unsubstituted or substituted aryl group, an unsubstituted or substituted alkenyl group, an unsubstituted or substituted aromatic heterocyclic residue, an unsubstituted or substituted alkoxy group, an unsubstituted or substituted alkylthio group, a hydroxyl group, or a halogen atom.

Hereinafter, preferable examples of the compounds represented by Formula (III) are shown.

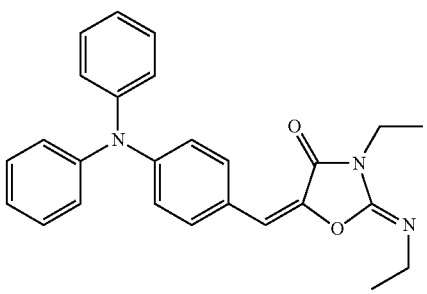

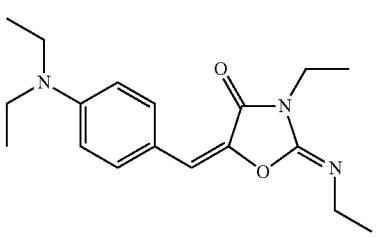

-continued

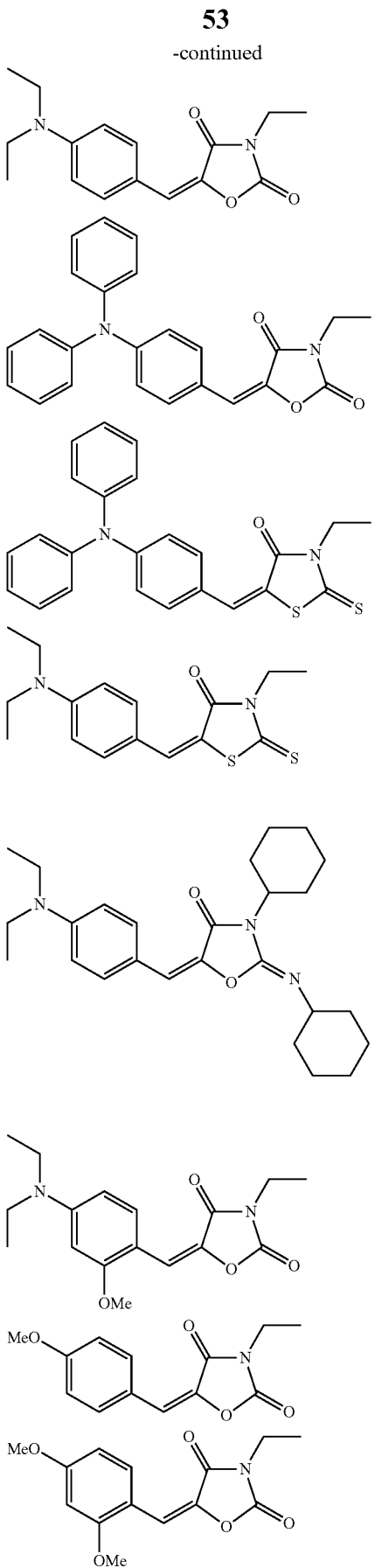

-continued

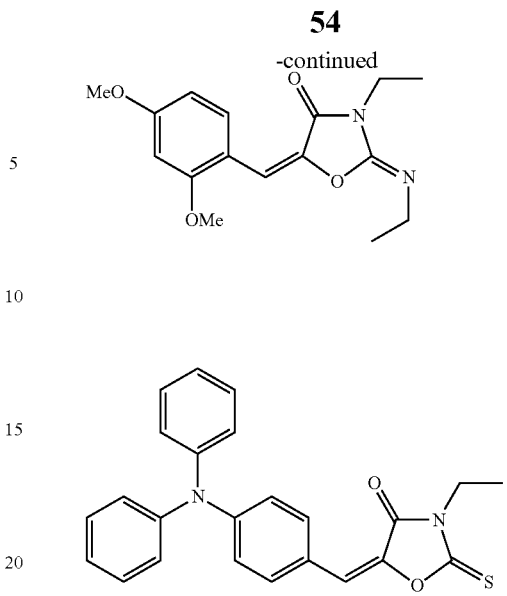

The content of the sensitizer in the polymerizable composition (1) is preferably from 0.1% by mass to 20% by mass, and more preferably from 0.5% by mass to 15% by mass in terms of solid content, from the viewpoint of the light absorption efficiency to the deep portion and the decomposition efficiency of an initiator.

The sensitizer may be used alone, or may be used in combination of two or more kinds (1): Co-sensitizer It is preferable that a co-sensitizer be further contained in the polymerizable composition (1).

In the invention, the co-sensitizer has a function of further increasing the sensitivity of (A) the specific oxime compound or the sensitizer to actinic radiation, or suppressing the polymerization inhibition of (B) the polymerizable compound due to oxygen, or the like.

Examples of such co-sensitizer include amines such as triethanol amine, ethyl p-dimethylamino benzoate, p-formyldimethyl aniline, p-methylthiodimethyl aniline; thiols and sulfides such as 2-mercaptobenzothiazole, 2-mercaptobenzoxazole, 2-mercaptobenzoimidazole, 2-mercapto-4 (3H)-quinazoline, β-mercaptonaphthalene; amino acid compounds (for example, N-phenylglycine, and the like); organic metal compounds (for example, tributyl tin acetate and the like) as recited in JP-B No. 48-42965; hydrogen donors as recited in JP-B No. 55-34414; and sulfur compounds (an example, trithiane and the like) as recited in JP-A No. 6-308727.

From the viewpoint of increasing the curing rate based on the balance of the polymerization growing rate and the chain transfer, the content of the co-sensitizer is preferably in the range of from 0.1% by mass to 30% by mass, more preferably in the range of from 1% by mass to 25% by mass, and still more preferably in the range of from 1.5% by mass to 20% by mass, relative to the total mass of the solid content of the polymerizable composition (1).

Further, a thiol compound as a co-sensitizer is preferably contained in the polymerizable composition (1).

As a thiol compound which may be contained in the polymerizable composition (1), the compound represented by following Formula (IV) is desirable.

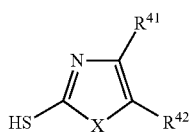
(IV)

In Formula (IV), X represent a sulfur atom, an oxygen atom, or —N(R$^{43}$)—, and R$^{43}$ represents a hydrogen atom, an alkyl group having 1 to 5 carbon atoms, or an aryl group having 6 to 13 carbon atoms. R$^{41}$ and R$^{42}$ each independently represent a hydrogen atom or an alkyl group having 1 to 5 carbon atoms, a hydroxyalkyl group having 1 to 3 carbon atoms, a phenyl group which may be substituted by an alkoxy group having 1 to 8 carbon atoms, a nitro group, an alkoxy carbonyl group having an alkyl group 1 to 8 carbon atoms, a phenoxycarbonyl group, an acetyl group, or a carboxyl group, and R$^{41}$ and R$^{42}$ together with the double bond, to which R$^{41}$ and R$^{42}$ are bonded, may form a benzene ring, and the double bond, to which R$^{41}$ and R$^{42}$ are bonded, may be hydrogenated.

Hereinafter, preferable examples of thiol compounds, which can be used in the invention, is shown together with the solubility in propylene glycol monomethyl ether acetate (PGMEA) as a solvent.

Herein, chemical formulae may be shown by simplified constitutional formulae, and the solid lines represent hydrocarbon groups, unless otherwise elements or substituents are specifically indicated. Further, in the following Examples, Me represents a methyl group.

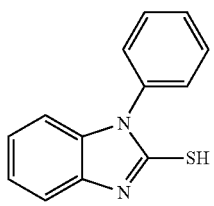
Solubility: 20 g/L or higher

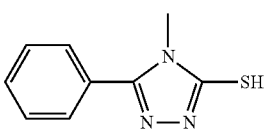
Solubility: 20 g/L or higher

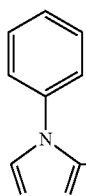
Solubility: 20 g/L or higher

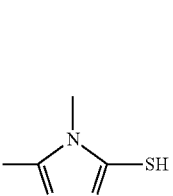
Solubility: 20 g/L or higher

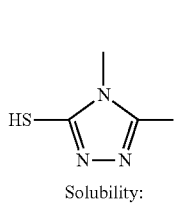
Solubility: 20 g/L or higher

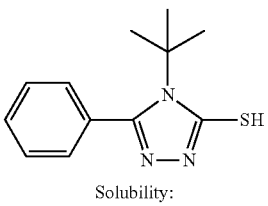
Solubility: 20 g/L or higher

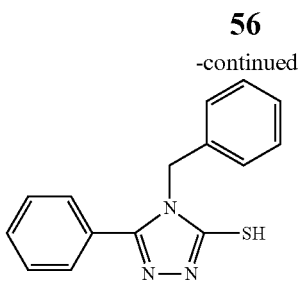
Solubility: 20 g/L or higher

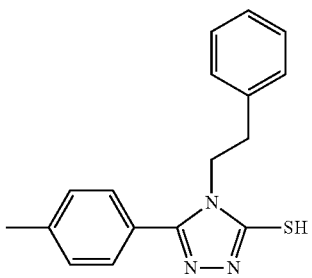
Solubility: 20 g/L or higher

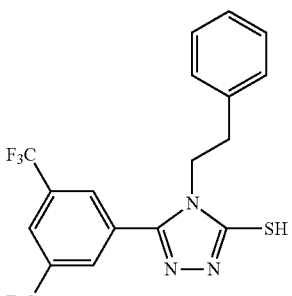
Solubility: 20 g/L or higher

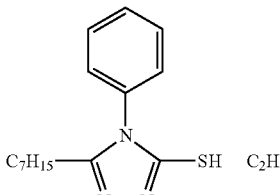
Solubility: 20 g/L or higher

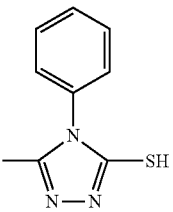
Solubility: 20 g/L or higher

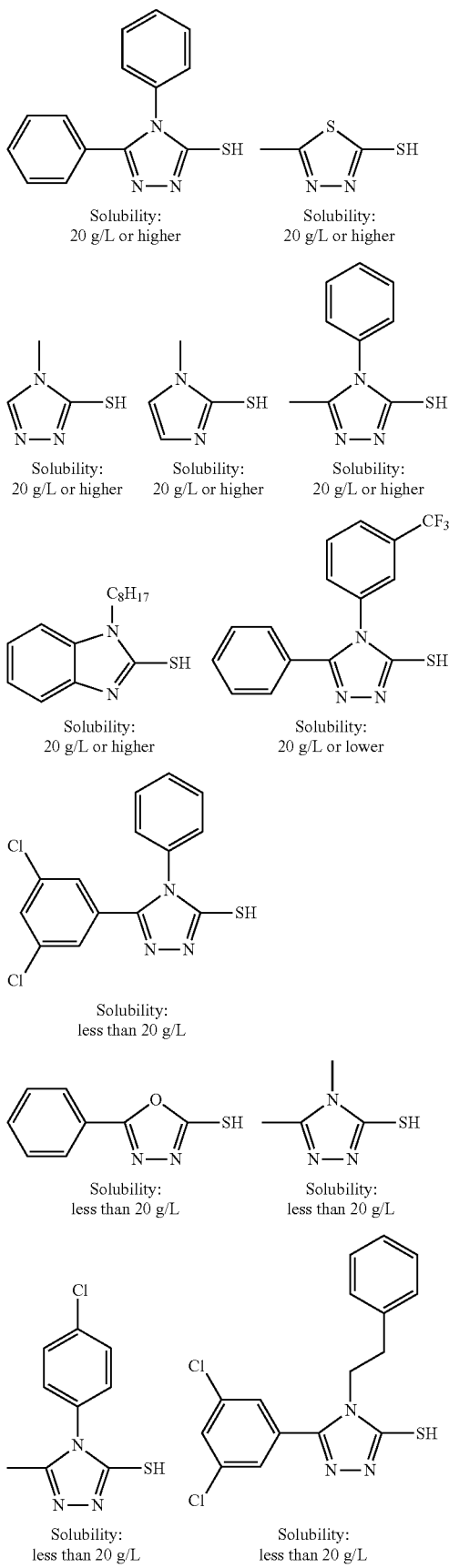
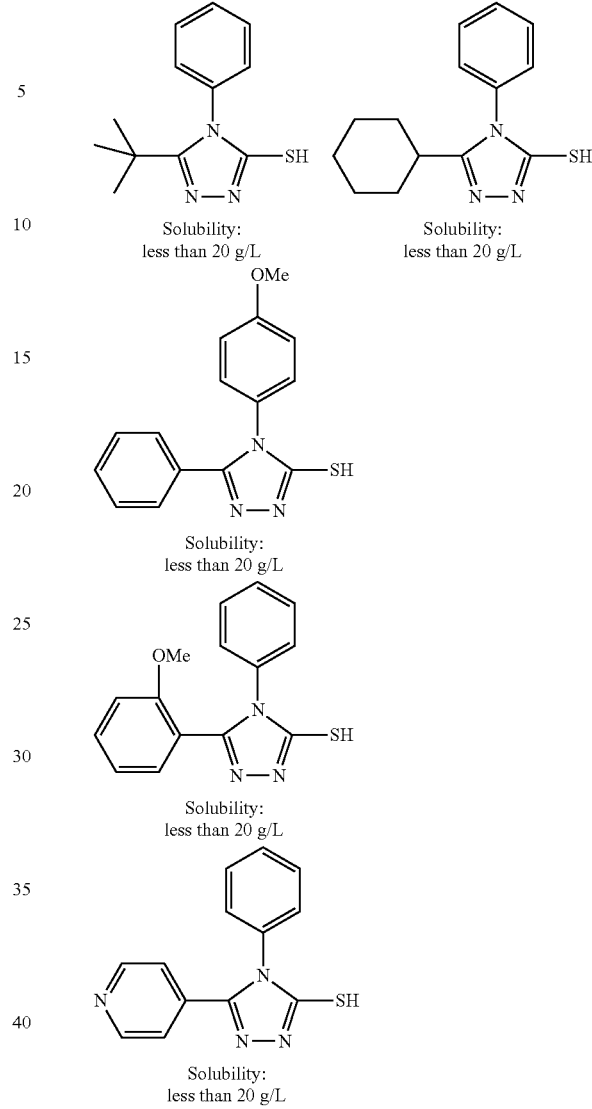

When the polymerizable composition (1) contains a thiol compound, the content of the thiol compound is preferably in the range of from 0.5% by mass to 30% by mass, more preferably in the range of from 1% by mass to 25% by mass, and still more preferably in the range of from 3% by mass to 20% by mass, relative to the total mass of the solid content of the polymerizable composition, from the viewpoint of increasing the curing rate based on the balance of the polymerization growing rate and the chain transfer.

(1): Binder Polymer

The polymerizable compositions (1) may further contain a binder polymer, if needed, for the purposes of improving film forming property or the like. As the binder polymer, it is desirable to use a linear organic polymer. As such "linear organic polymer", known polymers can arbitrarily be used. Preferably, in order to enable water development or weak alkaline solution development, a linear organic polymer which is soluble or swellable in water or weak alkaline solution is selected. The linear organic polymer is selected not only for use in a film-forming agent, but for use in water, weak alkaline solution or organic solvent developer. For example, when a water soluble organic polymer is used, water development becomes feasible. Example of such linear organic polymers include a radical polymer having a carboxylic acid group in a side chain thereof, for example, the polymers recited in JP-A No. 59-44615, JP-B No. 54-34327, JP-B No. 58-12577, JP-B No. 54-25957, JP-A No. 54-92723, JP-A No. 59-53836, and JP-A No. 59-71048, namely, resins formed by homopolymerizing or copolymerizing monomers having a carboxyl group, resins formed by homopolymerizing or copolymerizing monomers having an acid anhydride, and resins formed by hydrolyzing, or half-esterifying or half-amidating an acid anhydride unit, and epoxy acrylates formed by modifying an epoxy resin with unsaturated monocarboxylic acid or an acid anhydride. Examples of monomers having a carboxyl group include acrylic acid, methacrylic acid, itaconic acid, crotonic acid, maleic acid, fumaric acid, and 4-carboxyl styrene, and examples of monomers having an acid anhydride include maleic anhydride.

Similarly, a cellulose derivative having a carboxylic acid group at a side chain thereof may be used. In addition, a polymer formed by adding a cyclic acid anhydride to a polymer having a hydroxyl group, or the like is useful.

When an alkali soluble resin is used as a copolymer, other monomers other than the monomer aforementioned can also be used as a compound to be copolymerized. Examples of other monomers include the compounds in the following (1) to (12):

(1) acrylates and methacrylates having an aliphatic hydroxyl group, such as 2-hydroxyethyl acrylate, 2-hydroxypropyl acrylate, 3-hydroxypropyl acrylate, 4-hydroxybutyl acrylate, 2-hydroxyethyl methacrylate, 2-hydroxypropyl methacrylate, 3-hydroxypropyl methacrylate, 4-hydroxybutyl methacrylate, or the like;

(2) alkyl acrylates such as methyl acrylate, ethyl acrylate, propyl acrylate, butyl acrylate, isobutyl acrylate, amyl acrylate, hexyl acrylate, 2-ethylhexyl acrylate, octyl acrylate, benzyl acrylate, 2-chloroethyl acrylate, glycidyl acrylate, 3,4-epoxycyclohexyl methyl acrylate, vinyl acrylate, 2-phenylvinyl acrylate, 1-propenyl acrylate, allyl acrylate, 2-allyloxyethyl acrylate, propargyl acrylate, or the like;

(3) alkyl methacrylates such as methyl methacrylate, ethyl methacrylate, propyl methacrylate, butyl methacrylate, isobutyl methacrylate, amyl methacrylate, hexyl methacrylate, 2-ethylhexyl methacrylate, cyclohexyl methacrylate, benzyl methacrylate, 2-chloroethyl methacrylate, glycidyl methacrylate, 3,4-epoxycyclohexyl methyl methacrylate, vinyl methacrylate, 2-phenylvinyl methacrylate, 1-propenyl methacrylate, allyl methacrylate, 2-allyloxyethyl methacrylate, propargyl methacrylate, or the like;

(4) acrylamide or methacrylamide, such as acrylamide, methacrylamide, N-methylol acrylamide, N-ethyl acrylamide, N-hexyl methacrylamide, N-cyclohexyl acrylamide, N-hydroxyethyl acrylamide, N-phenyl acrylamide, N-nitrophenyl acrylamide, N-ethyl-N-phenyl acrylamide, vinyl acrylamide, vinyl methacrylamide, N,N-diallyl acrylamide, N,N-diallyl methacrylamide, allylacrylamide, allyl methacrylamide, or the like;

(5) vinyl ethers such as ethyl vinylether, 2-chloroethyl vinylether, hydroxyethyl vinylether, propyl vinylether, butyl vinylether, octyl vinylether, phenyl vinylether, or the like;

(6) vinyl esters such as vinyl acetate, vinyl chloroacetate, vinyl butylate, vinyl benzoate, or the like;

(7) styrenes such as styrene, α-methyl styrene, methyl styrene, chloromethyl styrene, p-acetoxy styrene, or the like;

(8) vinyl ketones such as methyl vinylketone, ethyl vinylketone, propyl vinylketone, phenyl vinylketone, or the like;

(9) olefins such as ethylene, propylene, isobutylene, butadiene, isoprene, or the like;

(10) N-vinyl pyrrolidone, acrylonitrile, methacrylonitrile, or the like;

(11) unsaturated imides such as maleimide, N-acryloyl acrylamide, N-acetyl methacrylamide, N-propionyl methacrylamide, N-(p-chlorobenzoyl)methacrylamide, or the like; and,

(12) methacrylic acid monomers having a hetero atom bonded to the α-position, for example, compounds recited in JP-A No. 2002-309057, JP-A No. 2002-311569, or the like.

Among them, a (meth)acrylate resin which has an allyl group or a vinyl ester group and a carboxyl group at a side chain thereof, an alkali soluble resin which has a double bond at a side chain thereof as recited in JP-A No. 2000-187322, or JP-A No. 2002-62698, and an alkali soluble resin which has an amide group at a side chain thereof as recited in JP-A No. 2001-242612 are excellent in the balance of film strength, sensitivity and developability, and are favorable.

Moreover, urethane binder polymers containing an acid group recited in JP-B No. 7-12004, JP-B No. 7-120041, JP-B No. 7-120042, JP-B No. 8-12424, JP-A No. 63-287944, JP-A No. 63-287947, JP-A No. 1-271741, JP-A No. 11-352691 and the like, and urethane binder polymers having an acid group and a double bond at the side chain as recited in JP-A No. 2002-107918 are excellent in the strength and are advantageous in view of printing durability, and low exposure suitability.

Further, acetal-modified polyvinyl alcohol binder polymers having an acid group as recited in European Patent No. 993966, European Patent No. 1204000, JP-A No. 2001-318463 and the like are excellent in the balance of the film strength and developability, and are favorable.

In addition to these, as a water-soluble linear organic polymer, polyvinyl pyrrolidone, polyethylene oxide, and the like are useful. Moreover, in order to increase the strength of a cured film, alcohol-soluble nylon, polyether of 2,2-bis-(4-hydroxyphenyl)-propane or epichlorohydrin, or the like is useful.

The weight average molecular weight of the binder polymer which can be used in the polymerizable composition (1) is preferably 5,000 or more, and more preferably in the range of from 10,000 to 300,000, and the number average molecular weight is preferably 1,000 or more, and more preferably in the range of from 2,000 to 250,000. The polydispersity (weight average molecular weight/number average molecular weight) is preferably one or more, and more preferably in the range of from 1.1 to 10.

These binder polymers may be any of a random polymer, a block polymer and a graft polymer.

The content of the binder polymer is preferably from 1 to 50% by mass, more preferably from 1 to 30% by mass, and sill more preferably from 1 to 20% by mass, in the total solid content of the polymerizable composition (1).

(1): Polymerization Inhibitor

In order to prevent unnecessary thermal polymerization of (B) the polymerizable compound during the manufacture or storage of the polymerizable composition (1), it is preferable to add a small amount of thermal-polymerization inhibitor in the polymerizable composition (1).

Examples of the thermal-polymerization inhibitor that can be used in the invention include hydroquinone, p-methoxy phenol, di-t-butyl-p-cresol, pyrogallol, t-butyl catechol, benzoquinone, 4,4'-thiobis(3-methyl-6-t-butylphenol), 2,2'-methylenebis(4-methyl-6-t-butylphenol), and N-nitrosophenyl hydroxyamine cerium (III) salt.

The addition amount of the thermal polymerization inhibitor is preferably from about 0.01% by mass to about 5% by mass with respect to the total solid content of the polymerizable composition (1).

If needed, in order to prevent the polymerization inhibition due to oxygen, a higher fatty acid derivative, such as behenic acid or behenic acid amide, or the like may be added, so that the additive is localized on the surface of the coated film in the process of drying after coating. The addition amount of the higher fatty acid derivative is preferably from about 0.5% by mass to about 10% by mass in the entire composition.

(1): Adhesion-Improving Agent

In order to enhance the adhesion of the formed cured film to a hard surface such as support, an adhesion-improving agent may be added to the polymerizable composition (1). The adhesion-improving agent may be exemplified by a silane coupling agent, a titanium coupling agent, or the like.

Preferable examples of the silane coupling agent include γ-methacryloxypropyl trimethoxysilane, γ-methacryloxypropyl triethoxysilane, γ-acryloxypropyl trimethoxysilane, γ-acryloyloxypropyl triethoxysilane, γ-mercaptopropyl trimethoxysilane, γ-aminopropyl triethoxysilane, and phenyl trimethoxysilane, and γ-methacryloxypropyl trimethoxysilane is more preferable.

The addition amount of the adhesion-improving agent is preferably from 0.5% by mass to 30% by mass, and more preferably from 0.7% by mass to 20% by mass, in the total solid content of the polymerizable composition (1).

(1): Diluent

Various organic solvents as diluents may be used for the polymerizable composition (1).

Examples of the organic solvents used herein include acetone, methyl ethyl ketone, cyclohexane, ethyl acetate, ethylene dichloride, tetrahydrofuran, toluene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 3-methoxypropanol, methoxymethoxy ethanol, diethylene glycol monomethyl ether, diethylene glycol monoethyl ether, diethylene glycol dimethyl ether, diethylene glycol diethyl ether, propylene glycol monomethylether acetate, propylene glycol monoethyl ether acetate, 3-methoxy propylacetate, N,N-dimethyl formamide, dimethyl sulfoxide, γ-butyrolactone, methyl lactate, and ethyl lactate.

These solvents may be used alone, or may be used in mixture.

The concentration of the solid content relative to the organic solvent in the polymerizable composition of the invention is preferably from 2% by mass to 60% by mass.

(1): Other Additives

Further, in order to improve the physical properties of the cured film, known additives such as an inorganic filler, a plasticizer, a sensitizing agent or the like may be added to the polymerizable composition (1).

Examples of the plasticizer include dioctylphthalate, didodecylphthalate, triethylene glycol dicaprylate, dimethylglycol phthalate, tricresyl phosphate, dioctyladipate, dibutyl sebacate, and triacetyl glycerin, and when a binder is used, a plasticizer can be added in an amount of 10% by mass or less relative to the total mass of a polymerizable compound and a binder polymer.

As described above, since the polymerizable composition (1) contains (A) the specific oxime compound, the polymerizable composition (1) is cured with high sensitivity, is excellent in storage stability, and further is capable of suppressing coloration at the time of heat-aging. Further, when the polymerizable composition (1) is applied to a surface of a hard material, and cured, high adhesiveness of the composition to the surface is attained.

In view of the fact that even when such a polymerizable composition (1) contains a colorant in a large quantity, the composition is capable of forming a pattern with high sensitivity, exerts excellent adhesion to a substrate, and even if the formed colored cured film is subjected to reiterative heating or light-irradiation, coloration or color changes can be suppressed, the composition is useful for forming colored areas in a color filter; accordingly, it is desirable to use the polymerizable composition (1) as a photopolymerization composition for a color filter.

Polymerizable composition (2): photopolymerizable composition for photosensitive planographic printing plate precursor Since the photopolymerizable composition of the invention can form a tough coat film in an exposed area by being cured with high sensitivity by pattern exposure, the photopolymerizable composition is useful for forming a photosensitive layer of a planographic printing plate precursor.

Hereinafter, preferable embodiments when the photopolymerizable composition of the invention is applied to the photosensitive layer of a planographic printing plate precursor are described.

(2)-(A) Specific Oxime Compound

The specific oxime compound contained in the polymerizable composition (2) can function as a polymerization initiator in the composition. The (A) specific oxime compound in this aspect is the oxime compound as stated above.

The content of (A) the specific oxime compound in the polymerizable composition (2) is preferably from 0.5% by mass to 40% by mass, more preferably from 1% by mass to 35% by mass, and still more preferably from 1.5% by mass to 30% by mass, with respect to the total solid content of the composition.

The specific oxime compound may be used alone, or may be used in combination of two or more kinds thereof.

Other Polymerization Initiators

In the polymerizable composition (2), other known polymerization initiators other than the specific oxime compound may be used to the extent that the effect of the invention is not impaired.

Examples of other polymerization initiators include (a) aromatic ketones, (b) an aromatic onium salt compound, (c) an organic peroxide, (d) a thio compound, (e) a hexaaryl biimidazole compound, (f) a ketoxime ester compound, (g) a borate compound, (h) an azinium compound, (i) a metallocene compound, (j) an active ester compound, and (k) a compound having a carbon-halogen bond. More specifically, examples of the polymerization initiators include polymerization initiators as recited in paragraphs [0081] to [0139] of JP-A No. 2006-78749.

(2)-(B) Polymerizable Compound

Preferable examples of (B) the polymerizable compound contained in the polymerizable composition (2) include addition-polymerizable compounds similarly to those as described in the polymerizable composition (1).

Details of methods for using the addition-polymerizable compound such as the structure, the single use or combined use, or the addition amount of these addition-polymerizable compounds can arbitrarily be determined in accordance with the design of performance of the target sensitive material. For example, the addition-polymerizable compound can be selected from the following point of view.

In view of sensitization speed, the structure having a higher content of unsaturated groups per one molecule is desirable, and in many cases, a bifunctional or higher functional structure is desirable. Further, in order to strengthen an image area, namely a cured film, a trifunctional or higher functional compound is preferable, and furthermore, a method of controlling both the photosensitivity and the strength by using polymerizable compounds having different number of functional groups or different polymerizable groups (for example, an acrylic ester, a methacrylic ester, a styrene compound, and a vinyl ether compound) in combination, is also effective. Compounds having a higher molecular weight or compounds having higher hydrophobicity provide excellent photosensitivity and film strength, whereas in some cases, these compounds may not be desirable in view of developing speed and precipitation in a developer.

Further, regarding the compatibility with other components (for example, a binder polymer, an initiator, a colorant, and the like) in the photosensitive layer, and the dispersibility, the selection and the method for use of the addition-polymerization compound are an important factor; and for example, the compatibility may be improved by the use of a low purity compound, or two or more kinds of addition-polymerization compounds. In some cases, a specific structure can be selected for the purpose of enhancing adhesion to a support, an overcoat layer, or the like. In view of sensitivity, it is advantageous to make the compound ratio of the addition-polymerizable compound in the photosensitive layer higher, but, in the case where the compound ratio is too high, an unfavorable phase separation may arise, or problems in the manufacturing process resulting from the tackiness of the photosensitive layer (for example, failure in manufacturing process resulting from transfer or tackiness of a component in the photosensitive components), or problems in precipitation in a developer, may arise.

From these points of view, the content of the addition-polymerizable compound is preferably from 5% by mass to 80% by mass, and more preferably from 25% by mass to 75% by mass, relative to the total solid content of the polymerizable composition (2).

Further, the addition-polymerizable compounds may be used alone, or may be used in combination of two or more kinds In addition, as to the method of use of the addition-polymerizable compound, suitable structure, compounding ratio and addition amount can be appropriately selected from the viewpoint of the degree of polymerization inhibition due to oxygen, resolution, fogging property, change in refractive index, surface tackiness and the like. In some cases, the addition-polymerizable compound may be applied to a layer structure such as an undercoat, an overcoat, or by a coating method.

(2): Binder Polymer

The polymerizable composition (2) preferably contains a binder polymer. The binder polymer is contained from the viewpoint of improving film property, and various binder polymers can be used as long as the binder polymer functions to improve the film property.

As the binder polymer, it is preferable to use a linear organic polymeric polymer. Such a "linear organic polymeric polymer" is not specifically limited to, and any linear organic polymeric polymer may be used. Preferably, a linear organic polymeric polymer which enables development using water or a weak alkaline solution, or is swellable in water or a weak alkaline solution is selected.

The linear organic polymeric polymer is used not only for a film-forming agent of the photopolymerizable composition, but is selected and used in accordance with the formulation of a developer including water, a weak alkaline solution or an organic solvent. For example, when a water soluble organic polymeric polymer is used, water development is feasible. Examples of such a linear organic polymeric polymer include addition polymers having a carboxylic group at the side chain as recited in JP-A No. 59-44615, JP-B No. 54-34327, JP-B No. 58-12577, JP-B No. 54-25957, JP-A No. 45-92723, JP-A No. 59-53836, and JP-A No. 59-71048, namely, a methacrylic acid copolymer, an acrylic acid copolymer, an itaconic acid copolymer, a crotonic acid copolymer, a maleic acid copolymer, and a partially esterified maleic acid copolymer. Similarly, examples also include acidic cellulose derivatives having a carboxylic acid group at the side chain. In addition, a polymer, in which a cyclic anhydride is added to an addition polymer having a hydroxyl group, is useful.

Further, suitable examples of the polymer include the binder polymer represented by the general formula (1) in JP-A No. 2006-301565.

The binder polymer may be mixed in the polymerizable composition (2) in an arbitrary quantity. From the viewpoint of the image strength and the like, the content of the binder polymer is preferably in the range of from 30% by mass to 85% by mass relative to the total solid content that forms a photosensitive layer. Further, it is preferable that the addition-polymerizable compound and the binder polymer be in the range of from 1/9 to 7/3 by mass ratio.

In a preferable exemplary embodiment, the binder polymer which is substantially insoluble in water but is soluble in alkali is used. In this way, an organic solvent, which is environmentally unfavorable, is not used, or can be limited to an extremely small amount. In such a method of use, the acid number (acid content in 1 g of polymer is expressed in terms of chemical equivalent number) and the molecular weight of the binder polymer are suitably selected from the viewpoint of the image strength and the developability. The acid number is preferably in the range of from 0.4 meq/g to 3.0 meq/g, and the molecular weight is preferably in the range of from 3,000 to 500,000. The acid number is more preferably in the range of from 0.6 to 2.0, and the molecular weight is more preferably in the range of from 10,000 to 300,000.

(2): Sensitizer

The polymerizable composition (2) desirably contains a sensitizer together with a polymerization initiator such as (A) the specific oxime compound. Examples of the sensitizer that can be used in the invention include a spectral sensitizing colorant, and a dye or pigment which absorbs light from a light source to interact with a polymerization initiator.

Preferable examples of spectral sensitizing colorant or dye include those recited in paragraphs [0144] to [0202] of JP-A No. 2006-78749 or the like.

Further, examples of sensitizers to be applied to the polymerizable composition (2) include the sensitizers described in the explanations of the polymerized composition (1).

The sensitizer may be used alone, or may be used in combination of two or more kinds thereof. The molar ratio of the total polymerization initiators and the sensitizer is from 100:0 to 1:99, more preferably from 90:10 to 10:90, and most preferably from 80:20 to 20:80, in the polymerizable composition (2).

(2): Co-Sensitizer

Known compounds, which additionally increase the sensitivity, suppress the polymerization inhibition due to oxygen, or the like, may be added as co-sensitizers to the polymerizable composition (2).

Examples of the co-sensitizers include the co-sensitizers described in the photopolymerizable composition (1). In addition to these, the examples of co-sensitizers include phosphorous compounds (diethylphosphite and the like) as recited in JP-A No. 6-250387.

When a co-sensitizer is used, the co-sensitizer is suitably used in an amount of from 0.01 part by mass to 50 parts by mass relative to 100 parts by mass of the total amount of the polymerization initiator contained in the polymerizable composition (2).

(2): Polymerization Inhibitor

In order to prevent compounds having a polymerizable ethylenic unsaturated double bond from unnecessary thermal polymerization during the manufacture or the storage of the composition, it is desirable to add a small amount of a thermal polymerization inhibitor to a polymerizable composition (2). Examples of the thermal polymerization inhibitors include hydroquinone, p-methoxy phenol, di-t-butyl-p-cresol, pyrogallol, t-butyl catechol, benzoquinone, 4,4'-thiobis(3-methyl-6-t-butylphenol), 2,2'-methylenebis(4-methyl-6-t-butyl phenol), and N-nitrosophenyl hydroxyamine cerium (III) salt.

The addition amount of the thermal polymerization inhibitor is preferably from about 0.01% by mass to about 5% by mass with respect to the mass of the entire composition. If needed, in order to prevent the polymerization inhibition due to oxygen, a higher fatty acid derivative, such as behenic acid or behenic acid amide, or the like is added, so that the additive is localizes on the surface of the coated film in the process of drying after coating. The addition amount of the higher fatty acid derivative is preferably about 0.5% by mass to about 10% by mass in the entire composition.

(2): (C) Colorant

A dye or a pigment may be added to the composition for the purpose of coloring a photosensitive layer. In this way, plate quality inspecting property of a printing plate, such as the visibility after plate-making or the suitability for an image density measuring apparatus, may be improved. Since most dyes cause reduction in the sensitivity of a photopolymerization-type photosensitive layer, the use of a pigment particularly as a colorant is desirable. Specific examples the colorant include pigments such as a phthalocyanine pigment, an azo pigment, carbon black, or titanium oxide, and dyes such as Ethyl Violet, Crystal Violet, an azo dye, an anthraquinone dye, or a cyanine dye. The addition amount of the dye and the pigment is preferably from about 0.5% by mass to about 5% by mass with respect to the entire composition.

(2): Other Additives

Further, in order to improve the physical properties of the cured film, an inorganic filler or other known additives such as a plasticizer, a sensitizer that can increase inking property on the surface of a photosensitive layer may be added.

Examples of the plasticizer include dioctylphthalate, didodecylphthalate, triethylene glycol dicaprylate, dimethylglycol phthalate, tricresyl phosphate, dioctyladipate, dibutyl sebacate, and triacetyl glycerin, and when a binder is used, a plasticizer can be added in an amount of 10% by mass or less relative to the total mass of a compound having an ethylenic unsaturated double bond and a binder polymer.

Further, a UV initiator, a thermal crosslinking agent, or the like may be added for enhancing the effect of heating and exposure after development for the purpose of improving film strength (printing durability).

Such a polymerizable composition (2) is applied on a support to form a photosensitive layer, thereby obtaining a planographic printing plate precursor of the invention. The planographic printing plate precursor of the invention will be described later.

Preferred uses of the polymerizable compositions of the invention, and representative compositions suitable for the respective uses, are described by way of the polymerizable composition (1) and the polymerizable composition (2). However, the uses of the polymerizable compositions of the invention are not limited to these uses, and the polymerizable compositions of the invention are suitably used for various materials to be polymerized and cured, and are used by controlling the addition amount of constituent components, the kind and amount of other additives and the like in accordance with the formulations.

Examples of other uses include molding resins, casting resins, stereolithographic resins, sealing agents, dental polymerization materials, printing inks, paints, photosensitive resins for printing plate, color proof for printing, photopolymerizable compositions for color filter, resists for black matrix, resists for printed circuit board, resists for manufacturing semiconductor, resists for microelectronics, resists for manufacturing micromachine components or the like, insulating materials, hologram materials, materials for wave guides, overcoat agents, adhesives, pressure-sensitive adhesives, curable pressure-sensitive adhesives, and release coating agents; and the polymerizable composition can used for these versatile uses.

Color filter and manufacturing method thereof.

Next, a color filter of the invention and the manufacturing method of the color filter are explained.

The color filter of the invention has, on a support, a colored pattern formed by using the photopolymerizable composition for color filter (the polymerizable composition (1)) of the invention.

Hereinafter, the color filter of the invention is explained in detail by way of the manufacturing method (manufacturing method of the color filter of the invention).

The manufacturing method of the color filter of the invention include at least: a process of applying a photopolymerizable composition (the polymerizable composition (1)) for color filter of the invention on a support to form a colored polymerizable composition layer (hereinafter, which may be simply referred to as a "polymerizable composition layer forming process", as occasion demands); a process of subjecting the polymerizable composition layer to pattern exposure (hereinafter, which may be simply referred to as an "exposure process", as occasion demands); and a process of forming a colored pattern by developing the polymerizable composition layer after the exposure and by removing an unexposed portion thereof (hereinafter, which may be simply referred to as a "developing process", as occasion demands).

Specifically, the photopolymerizable composition for color filter of the invention is coated directly on a support (substrate) or via another layer therebetween, to form a polymerizable composition layer (polymerizable composition layer forming process), the polymerizable composition layer is exposed to light through a predetermined mask pattern to cure only the light-irradiated coated film areas of the polymerizable composition layer (exposure process), and the exposed layer is developed using a developer (developing process) to form a patterned film including respective color pixels (three colors or four colors), whereby a color filter of the invention can be manufactured.

Hereinafter, each process in the manufacturing method of the color filter of the invention is explained.

Polymerizable Composition Layer Forming Process

In the polymerizable composition layer forming process, a layer including a colored polymerizable composition is formed by coating a support with the photopolymerizable composition for color filter of the invention.

Examples of the support which can be used in this process include soda glass used for a liquid crystal display element, PYREX (registered trademark) glass, quartz glass and any of the glass to which a transparent electroconductive film is adhered, a photoelectric conversion element substrate used for an image pick-up element such as a silicon board or the like or a complementary metal oxide semiconductor (CMOS). In some cases, black stripes are formed for separating pixels from one another on these substrates.

If needed, an undercoat layer may be formed on the supports, for improving adhesion to an upper-side layer on the undercoat layer, for preventing diffusion of substances, or for flattening the surface of the substrate.

As the coating method of the photopolymerizable composition for color filter of the invention on a support, various coating methods such as a slit coating, an inkjet method, a spin coating, a cast coating, a roll coating, or a screen printing method, are applicable.

The thickness of the coated film of the photopolymerizable composition for color filter is preferably from 0.1 μm to 10 μm, more preferably from 0.2 μm to 5 μm, and still more preferably from 0.2 μm to 3 μm.

Further, when a color filter for solid-state imaging device is manufactured, the thickness of the coated film of the photopolymerizable composition for color filter is preferably from 0.35 μm to 1.5 μm, and more preferably from 0.40 μm to 1.0 μm, from the viewpoint of resolution and developability.

The photopolymerizable composition for color filter coated on a support is usually dried under the conditions of about 70° C. to 110° C. for about 2 minutes to about 4 minutes, whereby a colored polymerizable composition layer is formed.

Exposure Process

In the exposure process, the polymerizable composition layer formed in the polymerizable composition layer forming process is subjected to pattern exposure. The pattern exposure is generally performed using a mask so that only the area irradiated with light in the coated film is cured, but, in some cases, the pattern exposure may be performed using scanning exposure according to the intended use.

The exposure is preferably performed by irradiation with radiation rays, and as the radiation rays used in the exposure, in particular, ultraviolet rays such as g-line, i-line or the like are preferably used, and an ultraviolet mercury lamp is more preferably used. The irradiation intensity is preferably from 5 mJ/cm$^2$ to 1,500 mJ/cm$^2$, more preferably from 10 mJ/cm$^2$ to 1,000 mJ/cm$^2$, and most preferably from 10 mJ/cm$^2$ to 800 mJ/cm$^2$.

Development Process

Subsequently, after the exposure process, an alkali development (development process) is performed, whereby a portion of the polymerizable composition layer, which is not irradiated with light in the exposure process, is eluted in an aqueous alkaline solution; as a result, only the photocured portion remains.

As the developer, an organic alkaline developer which does not damage the underlaid circuit or the like is desirable. Usually, the developing temperature is from 20° C. to 30° C., and developing time is from 20 seconds to 90 seconds.

As the alkali used for the developer, for example, an alkaline aqueous solution formed by diluting an organic alkaline compound such as aqueous ammonia, ethylamine, diethylamine, dimethyl ethanolamine, tetramethyl ammonium hydroxide, tetraethyl ammonium hydroxide, choline, pyrrole, piperidine, or 1,8-diazabicyclo[5,4,0]-7-undecene, with pure water to a concentration of from 0.001% by mass to 10% by mass, and preferably from 0.01% by mass to 1% by mass, is used. When a developer including such an alkaline aqueous solution is used, generally, washing (rinse) with pure water is preformed after development.

In addition, the manufacturing method of the color filter of the invention may include a curing process that cures the formed colored pattern by heating and/or exposure, if necessary, after performing the coloring polymerizable composition layer forming process, the exposure process, and the development process as described above.

The colored photopolymerizable composition layer forming process, the exposure process, and the developing process (and further a curing process, if necessary) as described above, are repeatedly performed to the desired number of times, whereby a color filter having the desired color hue can be manufactured.

Solid-State Imaging Device

The solid-state imaging device of the invention includes at least the color filter of the invention.

Since the photopolymerizable composition for color filter of the invention is used in the color filter of the invention, the formed colored pattern exhibits high adhesion to a support substrate, and the cured composition is excellent in development resistance. Accordingly, a high-resolution pattern having excellent exposure sensitivity, good adhesion to the substrate in exposed areas, and a desired cross-sectional profile, can be formed. Therefore, the color filter is suitably used for a liquid crystal display element and a solid-state imaging device such as a CCD element, or the like, and in particular, is suitable for a CCD and a CMOS having a high resolution exceeding 1,000,000 pixels. That is, it is preferable that the color filter of the invention be used for the solid-state imaging device.

The color filter of the invention, for example, can be used as a color filter arranged between a light receiving portion of each pixel which constitutes a CCD and a microlens for light condensing.

Planographic Printing Plate Precursor

Next, a planographic printing plate precursor of the invention is explained.

The planographic printing plate precursor of the invention includes at least: a support; and a photosensitive layer including the polymerizable composition (2) of the invention on the support.

For making a printing plate using the planographic printing plate precursor of the invention, the polymerizable composition (2) of the invention is directly applied on a support for a planographic printing plate or via another layer therebetween, to obtain a photopolymerizable composition layer, whereby a planographic printing plate precursor is obtained. Then, the photosensitive layer of the planographic printing plate precursor is subjected to pattern exposure to cure only the exposed area thereof, and unexposed areas are developed using a developer. As a result, the remaining photosensitive layer forms an ink receiving layer for printing, and the area, in which the photosensitive layer has been removed and a hydrophilic support is exposed, serves an area for receiving dampening water, thereby obtaining a planographic printing plate.

The planographic printing plate precursor of the invention may have other layers such as a protective layer, an intermediate layer or the like, if needed. Since the photosensitive layer contains the polymerizable composition of the invention, the planographic printing plate precursor of the invention is highly sensitive, is excellent in stability with the passage of time and excellent in printing durability. Hereinafter, each element of the planographic printing plate precursor of the invention is explained.

Photosensitive Layer

The photosensitive layer is a layer containing the photopolymerizable composition of the invention. Specifically, the polymerizable composition (2), which is one of the suitable aspects of the photopolymerizable compositions of the invention, is used as a composition for forming a photosensitive layer (hereinafter, may be referred to as a "composition for photosensitive layer", as occasion demands), and a coating solution, which includes the composition, is applied on a support and is dried, whereby the photosensitive layer is formed.

When a support is to be coated with the composition for the photosensitive layer, each component to be included in the composition is dissolved in various solvents and used. The solvent can suitably be selected from the viewpoint of solubility.

The appropriate concentration of solid content in the coating solution is from 2 to 50% by mass.

The coating amount of the photosensitive layer on a support may influence mainly the sensitivity of the photosensitive layer, the developability, the toughness and printing durability of the exposed film, and it is desirable to select in accordance with the intended use. When the coating amount is too small, the printing durability becomes insufficient. On the other hand, when the coating amount is too large, the sensitivity becomes low, the exposure is time consuming, and the developing processing requires longer time. Accordingly, both the cases are not desirable.

In the photosensitive layer for the planographic printing plate precursors for scanning exposure, which is a main purpose of the invention, the coating amount of the photosensitive layer is preferably in the range of from 0.1 $g/m^2$ to 10 $g/m^2$, and more preferably in the range of from 0.5 $g/m^2$ to 5 $g/m^2$.

Support

As the support of the planographic printing plate precursor in the invention, a support whose surface is hydrophilic is preferable. As the hydrophilic support, any conventionally known hydrophilic support, which is used for the planographic printing plate, can be used without limitation.

Examples of desirable supports include paper, a polyester film and an aluminum plate. Among them, an aluminum plate, which has excellent dimensional stability and is relatively inexpensive and which can provide a surface having excellent hydrophilicity and strength by being subjected to a surface treatment, as needed, is desirable.

In the case of a support having aluminum surface, it is desirable that the surface be subjected to a surface treatment such as a surface roughening (graining) processing or an immersion processing in an aqueous solution of sodium silicate, zirconium potassium fluoride, phosphate, or the like, or anodic oxidation processing.

The surface roughening processing of the surface of an aluminum plate may be performed by various methods. For example, a method in which the surface is mechanically roughened, a method in which the surface is electrochemically dissolved and roughened, or a method in which the surface is selectively chemically dissolved is used. As the mechanical method, known methods such as ball polishing, a brush polishing, a blast polishing, buff polishing, or the like can be used. Further, as the electrochemical surface roughening method, there is a method in which the surface roughening is carried out in an electrolytic solution using alternate current or direct current. Further, as disclosed in JP-A No. 54-63902, a method in which both the methods are combined together can also be utilized.

Further, an aluminum plate which is subjected to an immersion processing in a aqueous sodium silicate solution after the surface treatment is preferably used. As disclosed in JP-B No. 47-5125, an aluminum plate, which is subjected to immersion processing in an aqueous alkali metal silicate, after the aluminum plate is subjected to an anodic oxidation processing, is suitably used. The anodic oxidation processing can be performed, for example, in such a manner that an electric current is passed, by using an aluminum plate as an anode, through an electrolytic liquid formed by one kind, or combining two or more kinds of an aqueous solution or a non-aqueous solution of an inorganic acid such as phosphoric acid, chromic acid, sulfuric acid, or boric acid, or an organic acid such as oxalic acid, sulfamic acid or the like, or the salts thereof.

Furthermore, after performing an anodic oxidation processing, a hydrophilicizing processing such as a silicate processing or the like can be performed. Moreover, an aluminum plate, on which a water-soluble resin, for example, a polymer or a copolymer having a polyvinyl phosphonic acid or a sulfonic acid group at the side chain thereof, polyacrylic acid, a water-soluble metal salt (for example, zinc borate), or a yellow dye, an amine salt, or the like, is undercoated, is also preferable.

Protective Layer

The planographic printing plate precursor of the invention has desirably a protective layer further on the photosensitive layer.

As a material that can be used for the protective layer, for example, it is desirable that a water-soluble polymeric compound having relatively high crystallinity be used. Specific examples of materials of the protective layer include a water-soluble polymer such as polyvinyl alcohol, polyvinyl pyrrolidone, acidic celluloses, gelatin, gum Arabic, or polyacrylic acid. Among them, when a polyvinyl alcohol is used as a principal component, most positive results in basic characteristics such as oxygen blocking property or removability in development may be attained.

As long as the polyvinyl alcohol used for the protective layer has an unsubstituted vinyl alcohol unit having a required oxygen blocking property and water solubility, a part of the polyvinyl alcohol may be substituted by ester, ether, or acetal. Similarly, a part of the polyvinyl alcohol may include another copolymerizable component. Specific examples of the polyvinyl alcohol include a polyvinyl alcohol, in which 71% by mol to 100% by mol thereof is hydrolyzed and which has a molecular weight in the range of from 300 to 2,400 in terms of mass average molecular weight.

Further, the protective layer may also have other functions. For example, when a colorant (water-soluble dye or the like), which highly transmits light of 350 nm to 450 nm used for exposure, and efficiently absorbs light of 500 nm or longer, is added, safelight property can be further improved without reducing the sensitivity.

Other Layers

In addition, it is possible to arrange an additional layer in order to improve the adhesion between the photosensitive layer and the support, or improving the removability of an unexposed photosensitive layer in development.

For example, a compound, which has relatively strong interaction with a substrate, such as a compound having a diazonium structure, a phosphonic compound or the like may be added to the photosensitive layer, or an undercoat layer containing such compound may be formed between the substrate and the photosensitive layer, whereby it is possible to enhance the adhesion between the support and the photosensitive layer, and the printing durability.

On the other hand, when a hydrophilic polymer such as a polyacrylic acid or a polysulfone acid is added to the photosensitive layer, or an undercoat layer containing these compounds is formed, the developability of a non-image area can be improved, and scumming resistance can be improved.

Plate-Making

Usually, after the planographic printing plate precursor is subjected to an image-exposure to cure the photosensitive layer in the exposed area, an unexposed area of the photosensitive layer is removed using a developer to form an image, and thus, plate-making is performed. In this way, a printing plate can be obtained.

As the exposing method applicable to the planographic printing plate precursor of the invention, known methods may be used without limitation. In the invention, since (A) the specific oxime compound is used as a photopolymerization initiator, the wavelengths of an exposure light source are desirably from 350 nm to 450 nm, and specially, an InGaN semiconductor laser is suitable.

The exposure mechanism may be any mechanism such as an internal drum system, an external drum system, a flat-bed system, or the like. Further, the components in the photosensitive layer may be highly water-soluble so that the components can be soluble in neutral water or weak alkaline water; and a planographic printing plate having such a constitution can be applied to a so-called on-machine development method without using a wet development such that the planographic printing plate is exposed and developed on a printing machine after the printing plate is mounted on the machine.

Examples of available laser light sources of 350 to 450 nm include a gas laser, a solid-state laser, and a semiconductor laser.

In particular, an AlGaInN semiconductor laser (commercially available InGaN semiconductor laser of from 400 to 410 nm, 5 to 30 mW) is suitable in view of wavelength characteristics and cost.

Regarding a planographic printing plate exposure machine with a scanning exposure system, an exposure mechanism such as an internal drum system, an external drum system, or a flat-bed system may be used, and the light source thereof may be selected from the light sources described above and can be used in accordance with the intended use.

Examples of developer suitable for the planographic printing plate precursor of the invention include a developer as recited in JP-B. No. 57-7427, and aqueous solutions including an inorganic alkali agent such as sodium silicate, potassium silicate, sodium hydroxide, potassium hydroxide, lithium hydroxide, sodium tertiary phosphate, sodium secondary phosphate, ammonium tertiary phosphate, ammonium secondary phosphate, sodium metasilicate, sodium bicarbonate or aqueous ammonia, or an organic alkali agent such as monoethanolamine or diethanolamine are suitable. Such an alkaline solution is added so as to be a concentration of from 0.1% by mass to 10% by mass, and preferably from 0.5% by mass to 5% by mass, in the composition.

Further, a small amount of a surfactant or an organic solvent such as benzyl alcohol, 2-phenoxyethanol or 2-butoxyethanol can be included in such an alkaline aqueous solution, if needed. For example, examples of compounds include those recited in U.S. Pat. No. 3,375,171 and U.S. Pat. No. 3,615,480.

Furthermore, the developers as recited in JP-A. No. 50-26601, JP-A No. 58-54341, JP-B No. 56-39464, and JP-B No. 56-42860 are also preferable.

In addition, in the plate-making process of the planographic printing plate precursor, the entire surface of planographic printing plate precursor may be heated before exposure, during exposure, or after exposure and before development, if needed. The image forming reaction in the photosensitive layer is promoted by the heating, and advantages such as enhancement of sensitivity or printing durability, and stabilization of sensitivity can be attained. Furthermore, for the purpose of improving the image strength or printing durability, it is also effective to perform a post-heating of the entire surface of an image after development, or to perform an exposure of the entire surface of the image after development. In general, it is desirable to perform heating before development under a moderate condition of 150° C. or less. When heating is performed at 150° C. or less, the problem of fogging in a non-image area does not arise. The heating after development is performed under harsh conditions. That is, the temperature is usually in the range of from 200° C. to 500° C. Sufficient image strengthening action can be obtained at 200° C. or higher, and problems such as deterioration of the support or thermal decomposition of an image area are not caused at 500° C. or less.

EXAMPLES

Hereinafter, the invention will be explained by way of examples in more detail, but without departing from the sprit and scope of the invention, the invention is not limited to the following Examples. In addition, the term "part" is mass basis, and "%" is "% by mass", unless otherwise specified.

First, the details of the specific oxime compounds (Specific Compound 1 to Specific Compound 9) used in Examples and the comparative compounds (Comparative Compound 1 to Comparative Compound 4) used in Comparative Example are shown.

| Compound | Structure |
| --- | --- |
| Specific Compound 1 | 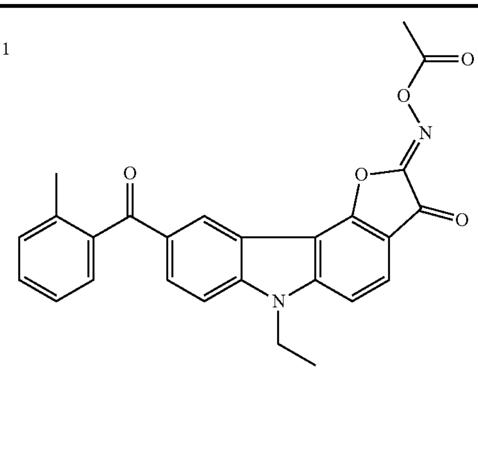 |

-continued
Specific Compound 2
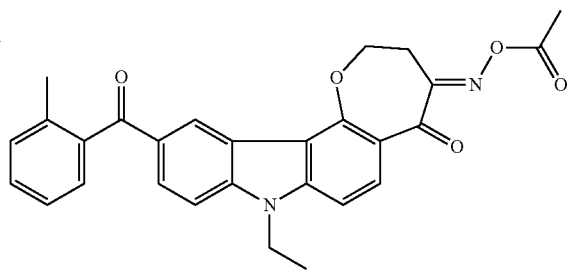 [SMILES: CCn1c2ccc(C(=O)c3ccccc3C)cc2c2c3c(ccc21)C(=O)/C(=N/OC(C)=O)CCO3]
Specific Compound 3
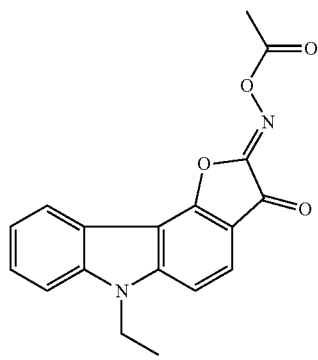 [SMILES: CCn1c2ccccc2c2c3c(ccc21)C(=O)/C(=N/OC(C)=O)O3]
Specific Compound 4
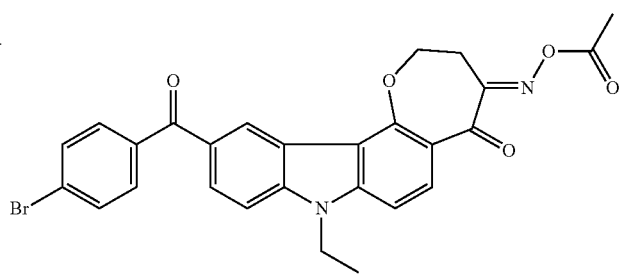
Specific Compound 5
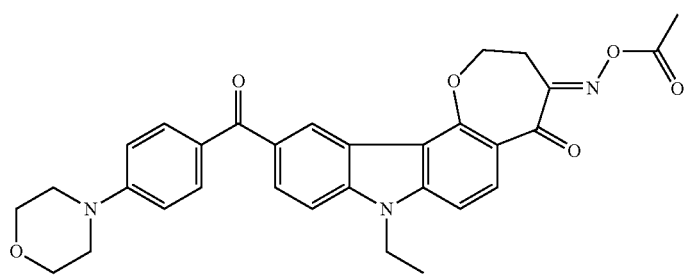 [SMILES: CCn1c2ccc(C(=O)c3ccc(N4CCOCC4)cc3)cc2c2c3c(ccc21)C(=O)/C(=N/OC(C)=O)CCO3]
| Compound | Compound |
|---|---|
Specific Compound 6
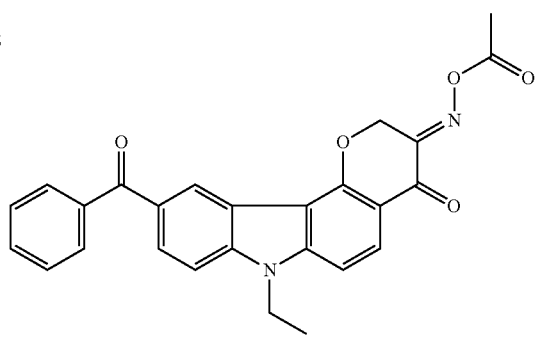

| | |
|---|---|
| Specific Compound 7 | 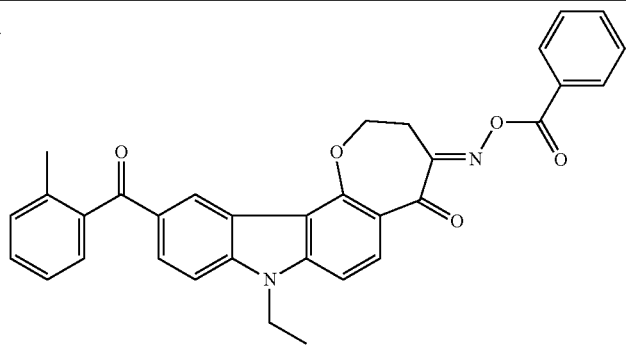 |
| Specific Compound 8 | 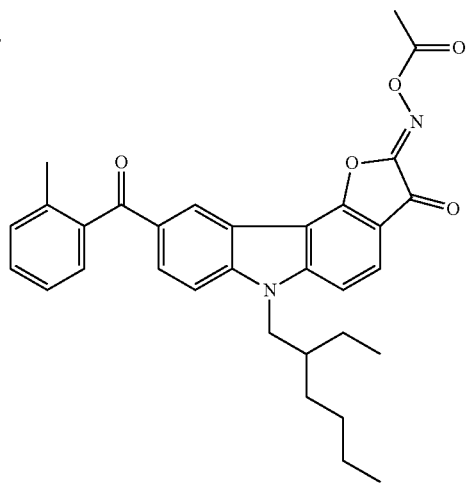 |
| Specific Compound 9 | 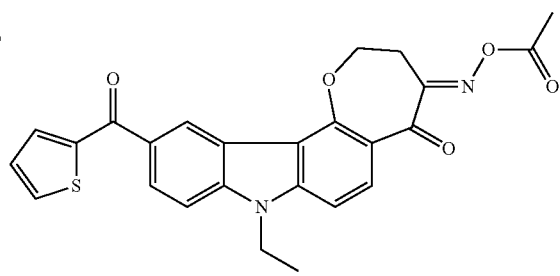 |
| Compound | Compound |
|---|---|
| Comparative Compound 1 | IRGACURE OXE 01 (manufactured by manufactured by Ciba Specialty Chemicals Inc.) |
| Comparative Compound 2 | IRGACURE OXE 02 (manufactured by manufactured by Ciba Specialty Chemicals Inc.) |
| Comparative Compound 3 | 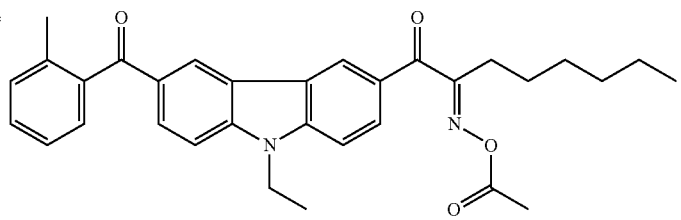 |

| Compound | Compound |
|---|---|
| Comparative Compound 4 | 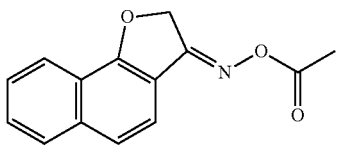 [SMILES: CC(=O)O/N=C1\COc2c1ccc1ccccc21] |

The structures of Comparative Compound 1 (trade name: IRGACURE OXE 01) and Comparative Compound 2 (trade name: IRGACURE OXE 02) shown in the above Table are as follows:

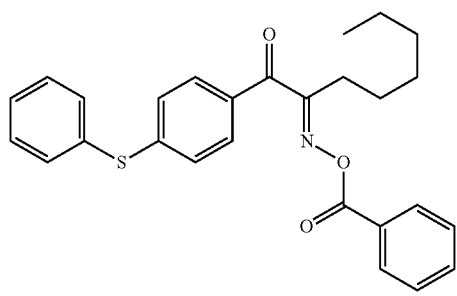

IRGACURE OXE 01

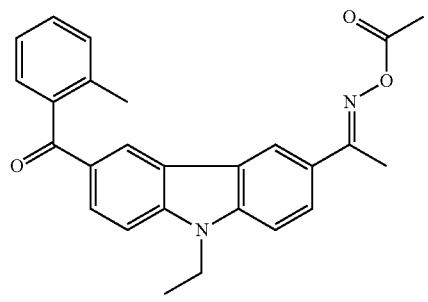

IRGACURE OXE 02

Specific Compound 1 to Specific Compound 9 as the specific oxime compounds were synthesized by the following methods.

Synthesis Example 1

Synthesis of Specific Compound 1 as Specific Oxime Compound

1. Synthesis of Compound A as Starting Substance 4-hydroxycarbazole (100 g) (0.546 mol) was dissolved in 1 L of acetone. To this solution, 150.6 g (1.09 mol) of potassium carbonate and 100.2 g (0.600 mol) of bromoethyl acetate were simultaneously added, and the resultant mixture was gently refluxed for 5 hours. This mixture was crystallized in 2 L of a 1N hydrochloric acid and filtered, thereby obtaining 134.5 g of Compound ($A^3$).

The obtained Compound ($A^3$) (30 g) (0.114 mol) was dissolved in 2 L of NMP. To this solution, 30.1 g (0.456 mol) of an 85% potassium hydroxide and 20.5 g (0.137 mol) of sodium iodide were added. To this reaction liquid, 14.9 g (0.137 mol) of ethyl bromide was added by dropping, and the mixture was stirred at 50° C. for 3 hours. The reaction liquid was added by dropping to 1N hydrochloric acid, and a solid was leached and dried at 40° C. for 5 hours, thereby obtaining Compound ($A^2$).

When 27.0 g of Compound ($A^2$) thus obtained is dissolved in 270 mL of methanesulfonic acid, the solution is changed from light brown color to dark brown color. This solution is stirred at 95° C. for 3 hours. A solid is crystallized in 1.5 L of distilled water and leached. The solid is dissolved in 300 mL of NMP and further crystallized in 1.5 L of distilled water, thereby obtaining a yellow solid of Compound ($A^1$) at a 73% yield.

The obtained Compounds ($A^1$) (10.0 g) was added to 200 mL of chlorobenzene, and dissolved at 50° C., thereby forming a clear liquid with orange color. After 10.5 g of aluminum chloride was added to this solution, and the mixture was stirred for 10 minutes, 6.1 g of o-toluic acid chloride was added by dropping to the resultant mixture over for 10 minutes. After this solution was heated and stirred at 50° C. for 3 hours, the solution was dropped to 1 L of a cool 1 N hydrochloric acid. Then, the water phase was decanted off, 200 mL of hexane was added to the remnant, and the mixture was stirred, thereby precipitating a brown solid. This solid was leached by filtration, washed with water and methanol, and dried at 50° C. for 5 hours, thereby obtaining Compound A at a 60% yield.

In the following, the synthetic scheme of Compound A is shown.

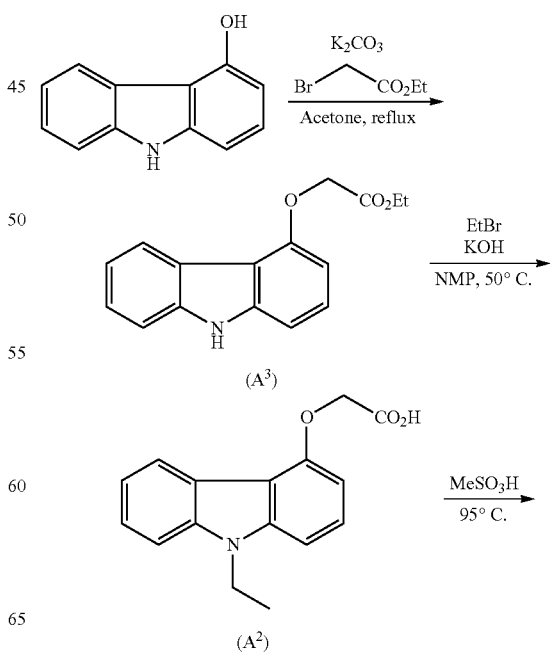

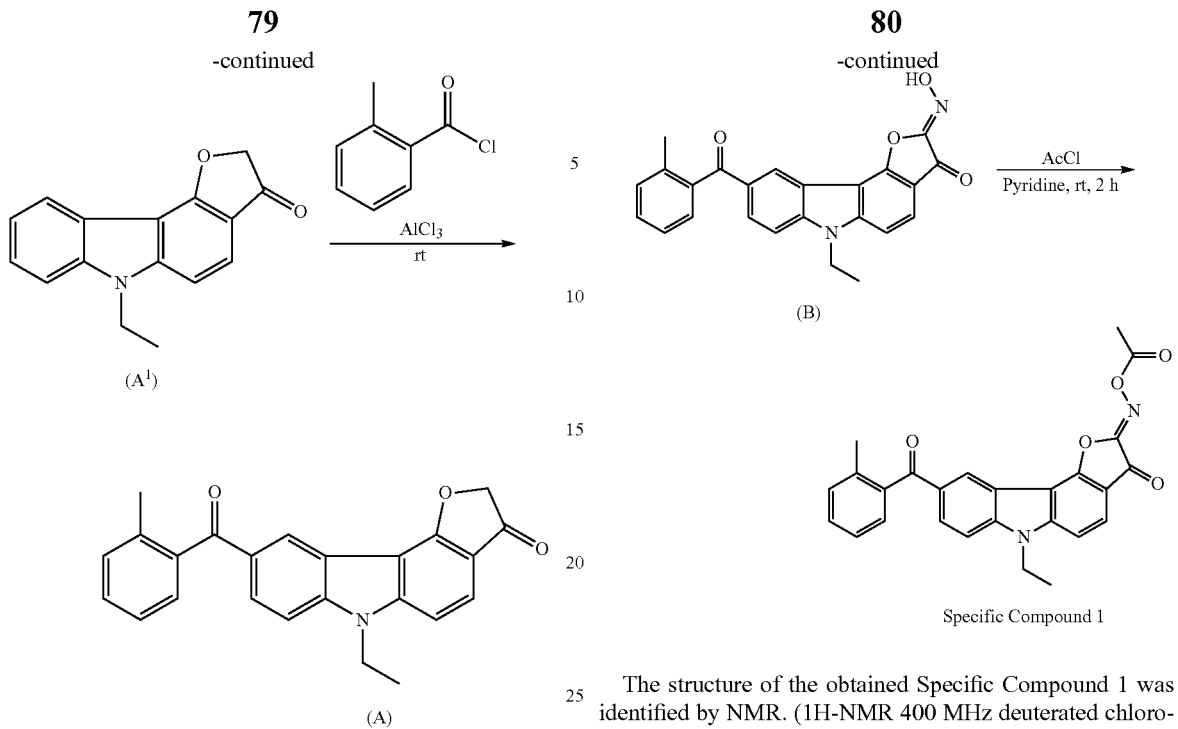

2. Synthesis of Specific Compound 1

Compound A (1.0 g, 2.71 mmol) obtained as described above was suspended in THF, and the suspension was cooled to 0° C. To this suspension, potassium t-butoxide (0.36 g, 3.25 mmol) was added, and the mixture was stirred at room temperature for one hour. In the meantime, Compound A was dissolved, and the reaction liquid became dark red. To this solution, 0.38 g (3.25 mmol) of isopentyl nitrate was added, and the mixture was further stirred for one hour. The solution was subjected to extraction with ethyl acetate, and after the extract was washed with 1N aqueous hydrochloric acid, the washed product was subjected to dehydration and decoloration operation using magnesium sulfate and active carbon. This ethyl acetate solution was reprecipitated in hexane, and was purified by column chromatography (hexane/ethyl acetate=1/1), thereby obtaining 0.21 g of Compounds B.

Compound B (0.3 g, 0.74 mmol) shown below was dissolved in 5 ml of pyridine, and the solution was cooled to 0° C. After acetyl chloride (0.87 g, 1.11 mmol) was added by dropping to the solution, the temperature of the solution was raised to room temperature and the solution was stirred for 2 hours. The reaction liquid was added by dropping to 150 ml of a 1N aqueous hydrochloric acid cooled at 0° C., and the precipitated crystal was purified by re-slurrying with methanol, thereby obtaining Specific Compound 1 having the following structure (yield: 0.11 g).

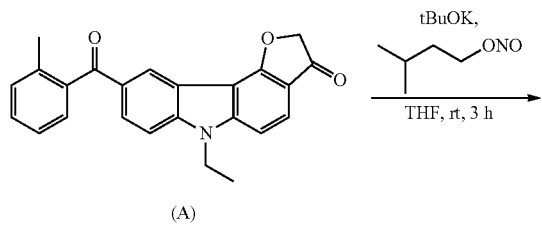

The structure of the obtained Specific Compound 1 was identified by NMR. (1H-NMR 400 MHz deuterated chloroform): 8.65 (s, 1H), 8.20 (dd, 1H, J=8.4, 1.5 Hz), 7.85 (d, 1H, J=8.4 Hz), 7.58 (d, 1H, J=8.7 Hz), 7.42-7.26 (m, 5H), 4.49 (q, 2H, J=7.2 Hz) 2.38 (s, 3H), 2.29 (s, 3H). 1.55 (t, 3H, 7.2 Hz).

The molar extinction coefficient at 365 nm of Specific Compound 1 measured by the method described above, was 5,200 in ethyl acetate.

Synthesis Example 2

Synthesis of Specific Compound 2 as Specific Oxime Compound

1. Synthesis of Compound C

Compound C was synthesized in a manner similar to the synthetic method of Compound A above, except that the ethyl bromoacetate used in the synthesis of Compound A was changed to methyl bromobutyrate.

2. Synthesis of Specific Compound 2

The obtained Compound C (2.0 g, 5.03 mmol) was dissolved in THF, and was cooled to 0° C. To this suspension, potassium t-butoxide (0.68 g, 6.04 mmol) was added, and the mixture was stirred at room temperature for one hour. In the meantime, Compound C was dissolved and the reaction liquid became dark red. To this solution, isopentyl nitrate (0.71 g, 6.04 mmol) was added, and the mixture was further stirred for one hour. The solution was subjected to extraction with ethyl acetate, and after the extract was washed with a 1N aqueous hydrochloric acid, the washed product was subjected to dehydration and decoloration operation using magnesium sulfate and active carbon. This ethyl acetate solution was reprecipitated in hexane, and was purified by column chromatography (hexane/ethyl acetate=1/1), thereby obtaining 0.71 g of Compound D.

The above Compound D (0.7 g, 1.64 mmol) was dissolved in 5 ml of pyridine, and the solution was cooled to 0° C. After acetyl chloride (0.19 g, 2.46 mmol) was added by dropping to the solution, the temperature of the solution was raised to room temperature and the solution was stirred for 2 hours. The reaction liquid was added by dropping to 150 ml of a 1N aqueous hydrochloric acid cooled to 0° C., and the precipitated crystal was purified by re-slurrying with 2-propanol, thereby obtaining Specific Compound 2 having the following structure (yield: 0.43 g).

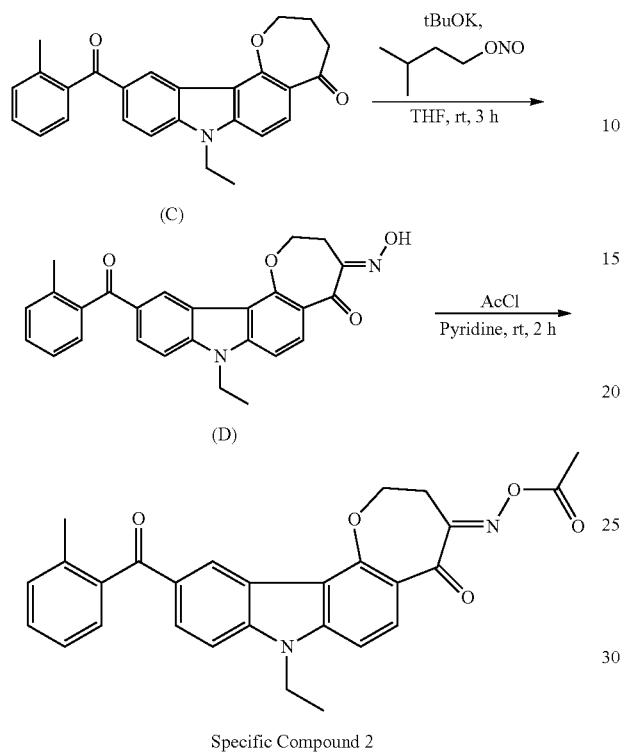

Specific Compound 2

The structure of the obtained Specific Compound 2 was identified by NMR. (1H-NMR 400 MHz deuterated chloroform): 8.87 (s, 1H), 8.07 (d, 1H, J=7.8 Hz), 7.92 (d, 1H, J=7.8 Hz), 7.43-7.27 (m, 5H), 7.15 (d, 1H, J=7.8 Hz), 4.67 (t, 2H, J=5.7 Hz), 4.41 (q, 2H, J=6.8 Hz), 3.40 (t, 2H, J=5.7 Hz), 2.36 (s, 3H), 2.27 (s, 3H), 1.47 (t, 3H, J=6.8 Hz).

The molar extinction coefficient at 365 nm of Specific Compound 2 measured in the same manner as in Synthesis Example 1, was 17,800 in ethyl acetate.

Further, Specific Compound 3 to Specific Compound 9, which are specific oxime compounds recited in the above list, were synthesized in a manner similar to Synthesis Example 1 and Synthesis Example 2.

That is, Specific Compound 3 was synthesized in the same manner as in Synthesis Example 1 except that Compound (A¹) obtained in the process of synthesizing Compound (A) was used as a starting substance in place of Compound (A) used in the Synthesis Example 1.

Specific Compound 4 was synthesized in the same manner as in Synthesis Example 2 except that p-bromobenzoyl chloride was used in place of o-toluic acid chloride used in the synthesis of Compound (C) which was an intermediate in Synthesis Example 2.

Specific Compound 5 was synthesized in the same manner as in Synthesis Example 2 except that p-fluorobenzoyl chloride was used in place of o-toluic acid chloride used in the synthesis of Compound (C) which was an intermediate in Synthesis Example 2, and thereafter, a process of substituting the fluorine atom by morpholine was performed.

Specific Compound 6 to Specific Compound 9 were synthesizable by similar methods as the above.

Synthesis Example 3

Synthesis of Exemplary Compound (A-62)

The following Exemplary Compound (A-62), which is encompassed in Formula (1B), was obtained in the same manner as in Synthesis Example 1 except that 2-hydroxycarbazole was used in place of 4-hydroxycarbazole used in the synthesis of Compound A that was the starting substance in Synthesis Example 1.

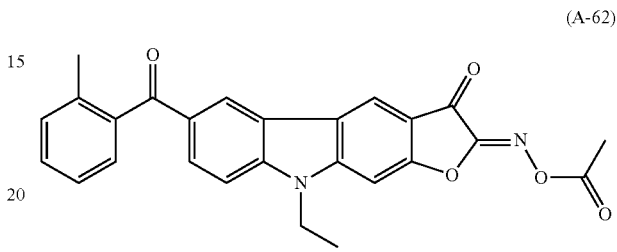

(A-62)

Synthesis Example 4

Synthesis of Exemplary Compound (A-69)

The following Exemplary Compound (A-69), which is encompassed in Formula (1B), was obtained in the same manner as in Synthesis Example 2 except that 2-hydroxycarbazole was used in place of 4-hydroxycarbazole used in the synthesis of Compound C which was the starting substance in Synthesis Example 2.

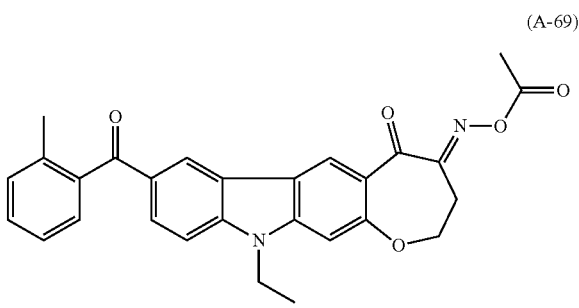 [SMILES: CCn1c2ccc(C(=O)c3ccccc3C)cc2c2cc3c(cc21)OCC/C(=N\OC(C)=O)C3=O]

(A-69)

Example 1-1

Manufacture of photopolymerizable composition 1 and evaluation thereof.

The photopolymerizable composition 1 was prepared as described below, and the sensitivity thereof was evaluated.

A homogeneous composition which contained 0.08 mmol of Specific Compound 1 as a specific oxime compound, 1 g of pentaerythritol tetraacrylate as a radical polymerizable compound, 1 g of polymethyl methacrylate (manufactured by Aldrich Corporation; molecular weight: ca. 996,000) as a binder resin, and 16 g of cyclohexanone as a solvent, was prepared.

The obtained polymerizable composition 1 was used as a coating liquid, and was applied on a glass plate by using a spin coater, and the coated liquid was dried at 40° C. for 10 minutes to form a coated film having a thickness of 1.5 μm. A 21√2 step tablet (gray scale film manufacture by Dainippon Screen Mfg. Co., Ltd.) was placed on the coated film, and after the film was exposed to light from a 500 mW high pressure mercury lamp (manufactured by Ushio, Inc.) for 30 seconds through a heat ray cut filter, the film was subjected to developing processing by being impregnated with toluene for 60 seconds.

The sensitivity was evaluated based on the number of steps corresponding to the step tablet, at which the film was completely cured, and it was found that the sensitivity was 7.

In addition, the sensitivity is higher as the number of the steps is larger.

Example 1-2 to Example 1-9, and Comparative Example 1-1 to Comparative Example 1-4

The photopolymerizable composition 2 to the photopolymerizable composition 13 were each prepared in the same manner as in Example 1-1, except that Specific Compound 1 (0.08 mmol) used as the specific oxime compound used in Example 1-1 was replaced with each compound (0.08 mmol) shown in the list above (Specific Compound 2 to Specific Compound 9 and Comparative Compound 1 to Comparative Compound 4). The sensitivity thereof was evaluated in the same manner as in Example 1-1.

The evaluation results of Examples 1-1 to 1-9 and Comparative Example 1-1 to Comparative Example 1-4 are shown in the following Table 1.

TABLE 1

| | Photo-polymerizable Composition | Compound | Photo-polymerizable Composition | Sensitivity Step |
|---|---|---|---|---|
| Example 1-1 | 1 | Specific Compound 1 | 1 | 7 |
| Example 1-2 | 2 | Specific Compound 2 | 2 | 9 |
| Example 1-3 | 3 | Specific Compound 3 | 3 | 8 |
| Example 1-4 | 4 | Specific Compound 4 | 4 | 9 |
| Example 1-5 | 5 | Specific Compound 5 | 5 | 8 |
| Example 1-6 | 6 | Specific Compound 6 | 6 | 8 |
| Example 1-7 | 7 | Specific Compound 7 | 7 | 9 |
| Example 1-8 | 8 | Specific Compound 8 | 8 | 8 |
| Example 1-9 | 9 | Specific Compound 9 | 9 | 9 |
| Comparative Example 1-1 | 10 | Comparative Compound 1 | 10 | 5 |
| Comparative Example 1-2 | 11 | Comparative Compound 2 | 11 | 5 |
| Comparative Example 1-3 | 12 | Comparative Compound 3 | 12 | 5 |
| Comparative Example 1-4 | 13 | Comparative Compound 4 | 13 | 6 |

Example 2-1

1. Manufacture of Colored Photopolymerizable Composition A-1

As a photopolymerizable composition for forming a color filter, a negative-working colored photopolymerizable composition A-1 containing a colorant (pigment) was prepared, and by using this, a color filter was manufactured.

1-1. Preparation of Pigment Dispersion (P1)

A mixed solution which contained 40 parts by mass of a mixture containing 30/70 (mass ratio) of C.I. Pigment Green 36 and C. I. Pigment Yellow 219 (C. I. Pigment Green 36/C.I. Pigment Yellow 219) as a pigment, 10 parts by mass (about 4.51 parts by mass in terms of solid content) of BYK2001 (DISPERBYK; solid concentration: 45.1% by mass, manufactured by BYK-Chemie GmbH) as a dispersant, and 150 parts by mass of ethyl-3-ethoxypropionate as a solvent, was mixed and dispersed using a beads mill for 15 hours, thereby obtaining a pigment dispersion (P1).

As a result of measurement of the average particle diameter of the pigment by a dynamic light scattering method, the average particle diameter of the pigment in the obtained pigment dispersion (P1) was 200 nm.

1-2. Preparation of Colored Photopolymerizable Composition A-1 (Coating Liquid)

The components of the following composition A-1 were mixed, and a colored photopolymerizable composition A-1 was prepared.

| Composition A-1 | |
|---|---|
| Pigment dispersion (P1) | 600 parts by mass |
| Alkali soluble resin (benzyl methacrylate/methacrylic acid/hydroxyethyl methacrylate copolymer; molar ratio: 80/10/10; Mw: 10,000) | 200 parts by mass |
| Polyfunctional monomer: dipentaerythritol hexaacrylate | 60 parts by mass |
| Specific oxime compound: Specific Compound 1 | 60 parts by mass |
| Solvent: propylene glycol monomethylether acetate | 1,000 parts by mass |
| Surfactant (TETRONIC 150R1 (trade name): manufactured by BASF SE.) | 1 part by mass |
| γ-Methacryloxypropyl triethoxysilane | 5 parts by mass |

2. Preparation of Color Filter 2-1. Formation of Colored Photopolymerizable Composition Layer The thus-obtained colored photopolymerizable composition A-1 containing the pigment, which was used as a resist liquid, was applied by slit-coating on a glass substrate having a size of 550 mm×650 mm. Thereafter, the substrate coated with the composition was left as it is for 10 minutes, and was subjected to a vacuum drying and prebaking (at 80° C. for 80 seconds), thereby forming a photopolymerizable composition-coated film (colored photopolymerizable composition layer).

Slit-Coating Conditions

Clearance of the opening portion at the tip end of coating head: 50 μm;

Coating speed: 100 mm/second;

Clearance between the substrate and the coating head: 150 μm;

Coated thickness (dry thickness): 2 μm; and

Coating temperature: 23° C.

2-2. Exposure and Development

Thereafter, the colored photopolymerizable composition layer was subjected to pattern exposure using a 2.5 kW ultra-high-pressure mercury lamp. The entire surface of the colored photopolymerizable composition layer after exposure was covered with a 10% aqueous solution of an organic developer (trade name: CD, manufactured by FujiFilm Electronic Materials Co., Ltd.), and was left as it is for 60 seconds.

2-3. Heat-Processing

Thereafter, pure water was sprayed in a shower-like flow onto the colored photopolymerizable composition layer to remove the developer, and subsequently, the glass plate with the composition layer thereon was heated in an oven at 220° C. for one hour (post-baking), thereby obtaining a color filter including the glass substrate having a colored pattern thereon.

3. Performance Evaluation

The storage stability and exposure sensitivity of the colored photopolymerizable composition, the developability when a colored pattern was formed on the glass plate by using the colored photopolymerizable composition, the coloration due to heat and the adhesion to the substrate of the obtained colored pattern, and the pattern cross-sectional profile at the time of heat-aging and the post-heating pattern cross-sectional profile were evaluated. The evaluation results are collectively shown in Tables 2A and 2B.

3-1. Storage Stability of Colored Photopolymerizable Composition

After storage of the colored photopolymerizable composition for one month at room temperature, the degree of deposition of foreign matters was visually inspected and evaluated in accordance with the following evaluation criteria:

Evaluation Criteria

A: No deposition was recognized;

B: deposition was slightly recognized; and

C: deposition was recognized.

3-2. Exposure Sensitivity of Colored Photopolymerizable Composition

The colored photopolymerizable composition was applied by spin-coating on a glass substrate, and was dried to form a coated layer having a layer thickness of 1.0 μm. The spin coating conditions were set to 300 rpm for 5 seconds, followed by 800 rpm for 20 seconds, and the drying conditions were set to 100° C. for 80 seconds. The obtained coated film was exposed to light through a test photomask having a line width of 2.0 μm with various exposure amounts in the range of from 10 mJ/cm$^2$ to 1,600 mJ/cm$^2$ by using a proximity type exposure machine having an ultra high-pressure mercury lamp (manufactured by Hitachi High-Tech Electronics Engineering Co., Ltd.). Next, the exposed coated film was developed using a 60% CD-2000 (trade name: CD, manufactured by FujiFilm Electronic Materials Co., Ltd.) developer under the condition of 25° C. for 60 seconds. Subsequently, the coated film was rinsed with running water for 20 seconds, and was spray dried, thereby finishing the patterning.

The exposure sensitivity was evaluated by defining the minimum exposure amount that achieves a film thickness after development in the area irradiated with light in the exposure process or 95% or more relative to the film thickness 100% before the exposure, as the exposure sensitivity. This shows that the sensitivity is higher as the value of exposure sensitivity is smaller.

3-3. Developability, Pattern Cross-Sectional Profile, and Adhesion to Substrate

The developability, the adhesion to a substrate, the change in color at the time of forced heat-aging, and the pattern cross-sectional profile were evaluated by observing the surface of the substrate and the cross-sectional profile after performing the post-baking in "2-3. heat-processing" by using an optical microscopic and SEM photographs in the usual way. The details of the valuation method are as follows.

Developability

The developability was evaluated by observing whether or not residues were present in the area where light was not irradiated (unexposed portion) in the exposure process. The evaluation criteria are as follows.

Evaluation Criteria

A: no residues in the unexposed area were recognized at all;

B: residues in the unexposed area were slightly recognized, but were not at a level of being problematic in practical use; and C: residues were remarkably recognized in the unexposed area.

Adhesion to Substrate

The adhesion to substrate was evaluated by observing whether or not defects in pattern arose. The evaluation criteria are as follows.

Evaluation Criteria

A: defects in pattern were not recognized at all;

B: defects in pattern were hardly recognized, but deficit in pattern were recognized in part; and C: significantly a large number of defects in pattern were recognized.

Evaluation of Coloration Caused by Forced Heat-Aging

The photopolymerizable composition layer (colored pattern) after exposure and development was heated using a hot plate at 200° C. for one hour. The color difference ΔEab* before and after heating by using MCPD-3000 manufactured by Otsuka Electronics Co., Ltd was evaluated in accordance with the following evaluation criteria;

Evaluation Criteria

A: ΔEab*≤5

B: 5<ΔEab*<8

C: ΔEab*≥8

Pattern Cross-Sectional Profile

The cross-sectional profile of the formed pattern was observed and evaluated. A rectangular cross-sectional profile of pattern is most desirable, and a forward tapered profile is secondarily desirable, but a reverse tapered profile is not desirable.

Post-Heating Pattern Cross-Sectional Profile

The cross-sectional profile of pattern that was formed after the post-baking performed in the "2-3. heat-processing" was observed and evaluated. A rectangular cross-sectional profile of the pattern is most desirable, and a forward tapered profile is secondarily desirable, but a reverse tapered profile is not desirable.

Examples 2-2 to 2-17, and Comparative Examples 2-1 to 2-3

Colored photopolymerizable compositions A-2 to A-17 and A'-1 to A'-3 were respectively produced in the same manner as in Example 2-1, except that 60 parts by mass of Specific Compound 1 (specific oxime compound) included in the composition A-1, which was used in the preparation of the colored photopolymerizable composition A-1 in Example 2-1, was replaced with the compounds and the amounts as shown in the following Tables 2A and 2B, respectively, and, furthermore, the sensitizers and co-sensitizers, of which kinds and amounts are shown in Tables 2A and 2B, were added in Examples 2-10 to 2-17, and color filters were prepared. Furthermore, the evaluation was performed in the same manner as in Example 2-1. The results are shown in Tables 2A and 2B.

TABLE 2A

| | Colored polymerizable composition | Polymerization initiator | | | Sensitizer | | Co-sensitizer | |
|---|---|---|---|---|---|---|---|---|
| | | Specific compound | Comparative compound | Content (parts by mass) | Kind | Content (parts by mass) | Kind | Content (parts by mass) |
| Example 2-1 | A-1 | 1 | — | 60 | — | — | — | — |
| Example 2-2 | A-2 | 2 | — | 60 | — | — | — | — |
| Example 2-3 | A-3 | 3 | — | 60 | — | — | — | — |
| Example 2-4 | A-4 | 4 | — | 60 | — | — | — | — |
| Example 2-5 | A-5 | 5 | — | 60 | — | — | — | — |
| Example 2-6 | A-6 | 6 | — | 60 | — | — | — | — |
| Example 2-7 | A-7 | 7 | — | 60 | — | — | — | — |
| Example 2-8 | A-8 | 8 | — | 60 | — | — | — | — |
| Example 2-9 | A-9 | 9 | — | 60 | — | — | — | — |
| Example 2-10 | A-10 | 2 | — | 50 | A-1 | 10 | — | — |
| Example 2-11 | A-11 | 2 | — | 50 | A-2 | 10 | — | — |
| Example 2-12 | A-12 | 2 | — | 50 | A-3 | 10 | — | — |
| Example 2-13 | A-13 | 2 | — | 50 | — | — | F1 | 10 |
| Example 2-14 | A-14 | 2 | — | 40 | A-1 | 10 | F1 | 10 |
| Example 2-15 | A-15 | 2 | — | 40 | A-2 | 10 | F2 | 10 |
| Example 2-16 | A-16 | 2 | — | 40 | A-2 | 10 | F3 | 10 |
| Example 2-17 | A-17 | 2 | — | 40 | — | — | F3 LD-5 | 10 10 |
| Comp. example 2-1 | A'-1 | — | 1 | 60 | — | — | — | — |
| Comp. Example 2-2 | A'-2 | — | 2 | 60 | — | — | — | — |
| Comp. Example 2-3 | A'-3 | — | 3 | 60 | — | — | — | — |

TABLE 2B

| | Storage stability | Exposure sensitivity (mJ/cm$^2$) | Developability | Change in color in forced heat-aging | Adhesion to substrate | Pattern cross-sectional profile | Post-heating pattern cross-sectional profile |
|---|---|---|---|---|---|---|---|
| Example 2-1 | A | 110 | A | A | A | Rectangular | Rectangular |
| Example 2-2 | A | 90 | A | A | A | Rectangular | Rectangular |
| Example 2-3 | A | 90 | A | A | A | Rectangular | Rectangular |
| Example 2-4 | A | 90 | A | A | A | Rectangular | Rectangular |
| Example 2-5 | A | 90 | A | A | A | Rectangular | Rectangular |
| Example 2-6 | A | 90 | A | A | A | Rectangular | Rectangular |
| Example 2-7 | A | 90 | A | A | A | Rectangular | Rectangular |
| Example 2-8 | A | 120 | A | A | A | Rectangular | Rectangular |
| Example 2-9 | A | 100 | A | A | A | Rectangular | Rectangular |
| Example | A | 90 | A | A | A | Rectangular | Rectangular |

TABLE 2B-continued

| | Storage stability | Exposure sensitivity (mJ/cm$^2$) | Developability | Change in color in forced heat-aging | Adhesion to substrate | Pattern cross-sectional profile | Post-heating pattern cross-sectional profile |
|---|---|---|---|---|---|---|---|
| Example 2-10 | | | | | | | |
| Example 2-11 | A | 80 | A | A | A | Rectangular | Rectangular |
| Example 2-12 | A | 90 | A | A | A | Rectangular | Rectangular |
| Example 2-13 | A | 80 | A | A | A | Rectangular | Rectangular |
| Example 2-14 | A | 80 | A | A | A | Rectangular | Rectangular |
| Example 2-15 | A | 80 | A | A | A | Rectangular | Rectangular |
| Example 2-16 | A | 70 | A | A | A | Rectangular | Rectangular |
| Example 2-17 | A | 70 | A | A | A | Rectangular | Rectangular |
| Comp. example 2-1 | A | 150 | A | B | C | Reverse tapered | Forward tapered |
| Comp. Example 2-2 | A | 140 | A | C | B | Reverse tapered | Forward tapered |
| Comp. Example 2-3 | A | 140 | A | B | B | Reverse tapered | Forward tapered |

In Tables 2A and 2B, and the following Tables 3A to 8, the numerical values 1 to 9 of the "specific compound" column in the "polymerization initiator" column indicate Specific Compounds 1 to Specific Compound 9, respectively, and the numerical values 1 to 3 of the "comparative compound" column indicate Comparative Compound 1 to Comparative Compound 3, respectively.

The sensitizers A1 to A3, and the c-sensitizers F1 to F3 and LD-5 shown in Tables 2A and 2B are the following compounds.

A1: 4,4-bisdiethyl aminobenzophenone
A2: diethyl thioxanthone
A3:

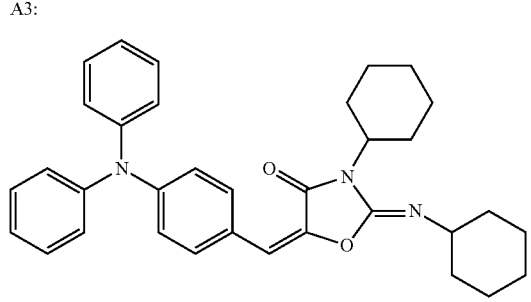 [SMILES: O=C1/C(=C\c2ccc(N(c3ccccc3)c3ccccc3)cc2)O/C(=N\C2CCCCC2)N1C1CCCCC1]

F1: 2-mercaptobezimidazole
F2: 2mercaptobenzothiazole
F3: N-phenyl-2-mercaptobenzimidazole
LD-5: 2,2'-bis(o-chlorophenyl)-4,4',5,5'-tetraphenylbiimidazole The results of Tables 2A and 2B show that the colored photopolymerizable composition of each Example, which contains the specific oxime compound (Specific Compound 1 to Specific Compound 9), is excellent in the storage stability (stability with the passage of time). Further, it turns out that these colored photopolymerizable compositions each have high exposure sensitivity, are excellent in the developability when used for forming a colored pattern of a color filter, do not cause coloration due to the heat-aging of the obtained colored pattern, and are excellent in the adhesion to the substrate, the pattern cross-sectional profile, and the post-heating pattern cross-sectional profile.

Example 3-1

1. Manufacture of Resist Liquid

A resist liquid was prepared by mixing and dissolving the components of the following composition.

| Composition of resist liquid | |
|---|---|
| Propylene glycol monomethylether acetate (PGMEA) | 19.20 parts by mass |
| Ethyl lactate | 36.67 parts by mass |
| Resin (40% PGMEA solution of benzyl methacrylate/methacrylic acid/2-hydroxyethyl methacrylate copolymer (molar ratio = 60/22/18)) | 30.51 parts by mass |
| Dipentaerythritol hexaacrylate (polymerizable compound) | 12.20 parts by mass |
| Polymerization inhibitor (p-methoxy phenol) | 0.0061 part by mass |
| Fluorine-containing surfactant (F-475; manufactured by DIC Corporation) | 0.83 parts by mass |
| Photopolymerization initiator (TAZ-107 (trihalomethyl triazine photopolymerization initiator; manufactured by Midori Kagaku Co., Ltd.) | 0.586 part by mass |

2. Manufacture of Silicon Wafer Board with Undercoat

A 6-inch silicon wafer was subjected to a heat processing at 200° C. for 30 minutes in an oven. Subsequently, the resist liquid was applied on the silicon wafer to attain a dry thickness of 2 μm, and further was heat-dried at 220° C. for one hour in an oven to form an undercoat layer, thereby obtaining a silicon wafer board with an undercoat.

3. Preparation of Colored Photopolymerizable Composition B-1

The components of the following composition B-1 were mixed, and the colored photopolymerizable composition B-1 containing a colorant (dye) was prepared.

| Composition B-1 | |
|---|---|
| Cyclohexanone | 80 parts by mass |
| Colorant: C.I. Acid Blue 108 | 7.5 parts by mass |
| Colorant: C.I. Solvent Yellow 162 | 2.5 parts by mass |
| Radical polymerizable monomer (polymerizable compound) (3:7 mixture of pentaerythritol triacrylate and dipentaerythritol hexaacrylate) | 7.0 parts by mass |
| Specific Compound 1 (specific oxime compound) | 2.5 parts by mass |
| Glycerol propoxylate (number average molecular weight Mn: 1,500, molar extinction coefficient $\epsilon$ = 0) | 0.5 part by mass |

4. Evaluation of Storage Stability of Colored Photopolymerizable Composition B-1 (Coating Liquid)

After storing the colored photopolymerizable composition B-1 for one month at room temperature, the degree of deposition of foreign matters was evaluated by visually inspecting in accordance with the following judgment criteria. The results are shown in the following Tables 3A and 3B.

Judgment Criteria

A: deposition was not recognized;
B: deposition was slightly recognized; and
C: deposition was recognized.

5. Manufacture and Evaluation of Color Filter Formed Using Colored Photopolymerizable Composition B-1

The colored photopolymerizable composition B-1 prepared in the above section 3. was applied on the undercoat layer of the silicon wafer board having an undercoat layer, which was obtained in the above section 2, to form a photocurable coated film. The coated film was subjected to a heat processing using a hot plate at 100° C. for 120 seconds, thereby forming a coated film having a dry thickness of 0.9 µm.

Subsequently, the coated film was irradiated with light of a wavelength of 365 nm at an exposure amount of 10 to 1,600 mJ/cm$^2$ through an island pattern mask having a 2 µm-square pattern by using an i-line stepper exposure machine FPA-3000i5+ (manufactured by Canon Inc.).

Thereafter, the silicon wafer board having the light-irradiated coated film thereon was placed on the horizontally rotary table of a spin shower development machine (DW-30 type; manufactured by Chemitronics Co., Ltd.), and was paddle developed using CD-2000 (manufactured by FujiFilm Electronic Materials Co., Ltd.) at 23° C. for 60 seconds, thereby forming a colored pattern on the silicon wafer board.

The silicon wafer board with the colored pattern formed thereon was fixed onto the horizontally rotary table with a vacuum chuck method. While rotating the silicon wafer board by a rotary machine at a number of revolutions of 50 rpm, pure water in a shower-like flow was sprayed from a spray nozzle from above the rotation center to perform a rinse processing, and thereafter, spray drying was performed.

In this way, a color filter, in which a colored pattern was formed on the board, was obtained.

Exposure Sensitivity and Pattern Size

The exposure sensitivity was evaluated by defining the minimum exposure amount that achieves a film thickness after development in the area irradiated with light in the exposure process of 95% or more relative to the film thickness 100% before the exposure. This shows that the sensitivity is higher as the value of the exposure sensitivity is smaller.

In this case, the size of the colored pattern was measured by using a critical dimension SEM "S-9260A" (manufactured by Hitachi High-Technologies Corporation). This shows that the curability is sufficient and the sensitivity is high as the pattern size become close to 2 µm.

The results are shown in the following Tables 3A and 3B.

Evaluation of developability, coloration due to heat-aging, adhesion to substrate, pattern cross-sectional profile, and post-heating pattern cross-sectional profile The evaluation of developability, coloration due to heat-aging, adhesion to substrate, pattern cross-sectional profile, and post-heating pattern cross-sectional profile was performed based on the evaluation methods and evaluation criteria performed in Example 2-1.

The results are shown in the following Tables 3A and 3B.

Examples 3-2 to 3-17, and Comparative Example 3-1 to 3-3

Colored photopolymerizable compositions B-2 to B-17 and B'-1 to B'-3 were respectively produced in the same manner as in Example 3-1, except that 2.5 parts by mass of Specific Compound 1 (specific oxime compound) included in the composition B-1, which was used in the preparation of the colored photopolymerizable composition B-1 in Example 3-1, was replaced with the compounds and the amounts as shown in the following Tables 3A and 3B, respectively, and, furthermore, the sensitizers and co-sensitizers, of which kinds and amounts are shown in Tables 3A an 3B, were added in Examples 3-10 to 3-17, and color filters were prepared. Furthermore, the evaluation similar to that of Example 3-1 was performed. The results are shown in Tables 3A and 3B.

TABLE 3A

| | Colored polymerizable composition | Polymerization initiator | | | Sensitizer | | Co-sensitizer | |
|---|---|---|---|---|---|---|---|---|
| | | Specific compound | Comparative compound | Content (parts by mass) | Kind | Content (parts by mass) | Kind | Content (parts by mass) |
| Example 3-1 | B-1 | 1 | — | 2.5 | — | — | — | — |
| Example 3-2 | B-2 | 2 | — | 2.5 | — | — | — | — |
| Example 3-3 | B-3 | 3 | — | 2.5 | — | — | — | — |
| Example 3-4 | B-4 | 4 | — | 2.5 | — | — | — | — |
| Example 3-5 | B-5 | 5 | — | 2.5 | — | — | — | — |
| Example 3-6 | B-6 | 6 | — | 2.5 | — | — | — | — |

TABLE 3A-continued

| | Colored polymerizable composition | Polymerization initiator | | | Sensitizer | | Co-sensitizer | |
|---|---|---|---|---|---|---|---|---|
| | | Specific compound | Comparative compound | Content (parts by mass) | Kind | Content (parts by mass) | Kind | Content (parts by mass) |
| Example 3-7 | B-7 | 7 | — | 2.5 | — | — | — | — |
| Example 3-8 | B-8 | 8 | — | 2.5 | — | — | — | — |
| Example 3-9 | B-9 | 9 | — | 2.5 | — | — | — | — |
| Example 3-10 | B-10 | 2 | — | 2.0 | A1 | 0.5 | — | — |
| Example 3-11 | B-11 | 2 | — | 2.0 | A2 | 0.5 | — | — |
| Example 3-12 | B-12 | 2 | — | 2.0 | A3 | 0.5 | — | — |
| Example 3-13 | B-13 | 2 | — | 2.0 | — | — | F1 | 0.5 |
| Example 3-14 | B-14 | 2 | — | 1.5 | A2 | 0.5 | F1 | 0.5 |
| Example 3-15 | B-15 | 2 | — | 1.5 | A2 | 0.5 | F2 | 0.5 |
| Example 3-16 | B-16 | 2 | — | 1.5 | A2 | 0.5 | F3 | 0.5 |
| Example 3-17 | B-17 | 2 | — | 1.5 | | | F3 LD-5 | 0.5 0.5 |
| Comp. example 3-1 | B'-1 | — | 1 | 2.5 | — | — | — | — |
| Comp. Example 3-2 | B'-2 | — | 2 | 2.5 | — | — | — | — |
| Comp. Example 3-3 | B'-3 | — | 3 | 2.5 | — | — | — | — |

TABLE 3B

| | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-1 | A | 1000 | 1.96 | A | A | A | Rectangular | Rectangular |
| Example 3-2 | A | 900 | 1.97 | A | A | A | Rectangular | Rectangular |
| Example 3-3 | A | 900 | 1.97 | A | A | A | Rectangular | Rectangular |
| Example 3-4 | A | 900 | 1.97 | A | A | A | Rectangular | Rectangular |
| Example 3-5 | A | 900 | 1.97 | A | A | A | Rectangular | Rectangular |
| Example 3-6 | A | 900 | 1.97 | A | A | A | Rectangular | Rectangular |
| Example 3-7 | A | 1200 | 1.94 | A | A | A | Rectangular | Rectangular |
| Example 3-8 | A | 900 | 1.97 | A | A | A | Rectangular | Rectangular |
| Example 3-9 | A | 900 | 1.97 | A | A | A | Rectangular | Rectangular |
| Example 3-10 | A | 850 | 1.97 | A | A | A | Rectangular | Rectangular |
| Example 3-11 | A | 850 | 1.97 | A | A | A | Rectangular | Rectangular |
| Example 3-12 | A | 800 | 1.98 | A | A | A | Rectangular | Rectangular |
| Example 3-13 | A | 850 | 1.98 | A | A | A | Rectangular | Rectangular |
| Example 3-14 | A | 800 | 1.98 | A | A | A | Rectangular | Rectangular |

TABLE 3B-continued

|  | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-15 | A | 800 | 1.98 | A | A | A | Rectangular | Rectangular |
| Example 3-16 | A | 750 | 1.98 | A | A | A | Rectangular | Rectangular |
| Example 3-17 | A | 750 | 1.98 | A | A | A | Rectangular | Rectangular |
| Comp. example 3-1 | A | 1400 | 1.92 | A | B | C | Reverse tapered | Forward tapered |
| Comp. Example 3-2 | A | 1300 | 1.92 | A | C | B | Reverse tapered | Forward tapered |
| Comp. Example 3-3 | A | 1300 | 1.92 | A | B | B | Reverse tapered | Forward tapered |

The sensitizers A1 to A3, the co-sensitizers F1 to F3, and LD-5 which are shown in Tables 3A and 3B are the aforementioned compounds.

Example 3-18

The components of the following composition C-1 were mixed, and the colored photopolymerizable composition C-1 containing a colorant (pigment) was prepared.

| Composition C-1 | |
|---|---|
| Ethyl-3-ethoxypropionate (solvent) | 17.9 parts by mass |
| Colorant (dispersion of C.I. Pigment Red 25) (solid content: 15% by mass; pigment content in solid content: 60%) | 26.7 parts by mass |
| Colorant (dispersion of C.I. Pigment Yellow 139) (solid content: 15 mass %, pigment content in solid content 60%) | 17.8 parts by mass |
| Radical polymerizable monomer (polymerizable compound) (mixture of 3:7 of pentaerythritol triacrylate and dipentaerythritol hexaacrylate) | 3.5 parts by mass |
| Specific Compound 1 (specific oxime compound) | 0.5 part by mass |

-continued

| Composition C-1 | |
|---|---|
| Benzyl methacrylate/methacrylic acid copolymer (molar ratio = 70/30) | 2.0 parts by mass |

Examples 3-19 to 3-34, and Comparative Example 3-4 to 3-6

Colored photopolymerizable compositions C-2 to C-17 and C'-1 to C'-3 were respectively produced in the same manner as in Example 3-18, except that 0.5 part by mass of Specific Compound 1 (specific oxime compound) included in the composition C-1, which was used in the preparation of the colored photopolymerizable composition C-1 in Example 3-18, was replaced with the compounds and the amounts as shown in the following Tables 4A and 4B, respectively, and, furthermore, the sensitizers and co-sensitizers, of which kinds and amounts are shown in Tables 4A and 4B, were added in Example 3-27 to 3-34, and color filters were prepared.

The obtained colored photopolymerizable compositions each were evaluated in a manner similar to those in Example 3-1. The results are shown in Tables 4A and 4B.

TABLE 4A

| | Colored polymerizable composition | Polymerization initiator | | | Sensitizer | | Co-sensitizer | |
|---|---|---|---|---|---|---|---|---|
| | | Specific compound | Comparative compound | Content (parts by mass) | Kind | Content (parts by mass) | Kind | Content (parts by mass) |
| Example 3-18 | C-1 | 1 | — | 0.5 | — | — | — | — |
| Example 3-19 | C-2 | 2 | — | 0.5 | — | — | — | — |
| Example 3-20 | C-3 | 3 | — | 0.5 | — | — | — | — |
| Example 3-21 | C-4 | 4 | — | 0.5 | — | — | — | — |
| Example 3-22 | C-5 | 5 | — | 0.5 | — | — | — | — |
| Example 3-23 | C-6 | 6 | — | 0.5 | — | — | — | — |
| Example 3-24 | C-7 | 7 | — | 0.5 | — | — | — | — |

TABLE 4A-continued

| | Colored polymerizable composition | Polymerization initiator | | | Sensitizer | | Co-sensitizer | |
|---|---|---|---|---|---|---|---|---|
| | | Specific compound | Comparative compound | Content (parts by mass) | Kind | Content (parts by mass) | Kind | Content (parts by mass) |
| Example 3-25 | C-8 | 8 | — | 0.5 | — | — | — | — |
| Example 3-26 | C-9 | 9 | — | 0.5 | — | — | — | — |
| Example 3-27 | C-10 | 2 | — | 0.4 | A1 | 0.1 | — | — |
| Example 3-28 | C-11 | 2 | — | 0.4 | A2 | 0.1 | — | — |
| Example 3-29 | C-12 | 2 | — | 0.4 | A3 | 0.1 | — | — |
| Example 3-30 | C-13 | 2 | — | 0.4 | — | — | F1 | 0.1 |
| Example 3-31 | C-14 | 2 | — | 0.3 | A2 | 0.1 | F1 | 0.1 |
| Example 3-32 | C-15 | 2 | — | 0.3 | A2 | 0.1 | F2 | 0.1 |
| Example 3-33 | C-16 | 2 | — | 0.3 | A2 | 0.1 | F3 | 0.1 |
| Example 3-34 | C-17 | 2 | — | 0.3 | — | — | F3 / LD-5 | 0.1 / 0.1 |
| Comp. example 3-4 | C'-1 | — | 1 | 0.5 | — | — | — | — |
| Comp. Example 3-5 | C'-2 | — | 2 | 0.5 | — | — | — | — |
| Comp. Example 3-6 | C'-3 | — | 3 | 0.5 | — | — | — | — |

TABLE 4B

| | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-18 | A | 900 | 1.97 | A | A | A | Rectangular | Rectangular |
| Example 3-19 | A | 700 | 1.98 | A | A | A | Rectangular | Rectangular |
| Example 3-20 | A | 700 | 1.98 | A | A | A | Rectangular | Rectangular |
| Example 3-21 | A | 700 | 1.98 | A | A | A | Rectangular | Rectangular |
| Example 3-22 | A | 700 | 1.98 | A | A | A | Rectangular | Rectangular |
| Example 3-23 | A | 700 | 1.98 | A | A | A | Rectangular | Rectangular |
| Example 3-24 | A | 700 | 1.96 | A | A | A | Rectangular | Rectangular |
| Example 3-25 | A | 1000 | 1.98 | A | A | A | Rectangular | Rectangular |
| Example 3-26 | A | 800 | 1.98 | A | A | A | Rectangular | Rectangular |
| Example 3-27 | A | 650 | 1.98 | A | A | A | Rectangular | Rectangular |
| Example 3-28 | A | 650 | 1.98 | A | A | A | Rectangular | Rectangular |
| Example 3-29 | A | 650 | 1.98 | A | A | A | Rectangular | Rectangular |
| Example 3-30 | A | 650 | 1.98 | A | A | A | Rectangular | Rectangular |
| Example 3-31 | A | 650 | 1.98 | A | A | A | Rectangular | Rectangular |
| Example 3-32 | A | 650 | 1.98 | A | A | A | Rectangular | Rectangular |

TABLE 4B-continued

| | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-33 | A | 600 | 1.98 | A | A | A | Rectangular | Rectangular |
| Example 3-34 | A | 600 | 1.98 | A | A | A | Rectangular | Rectangular |
| Comp. example 3-4 | A | 1200 | 1.92 | A | B | C | Reverse tapered | Forward tapered |
| Comp. Example 3-5 | A | 1100 | 1.92 | A | C | B | Reverse tapered | Forward tapered |
| Comp. Example 3-6 | A | 1100 | 1.92 | A | A | B | Reverse tapered | Forward tapered |

The sensitizers A1 to A3, the co-sensitizers F1 to F3, and LD-5 as shown in Tables 3A and 4B are the aforementioned compounds.

Example 3-35

The components of the following composition D-1 were mixed, and a colored photopolymerizable composition D-1 containing a colorant (pigment) was prepared.

| Composition D-1 | |
|---|---|
| Ethyl-3-ethoxypropionate (solvent) | 17.9 parts by mass |
| Colorant (dispersion of C.I. Pigment Red 254) (solid content: 15% by mass; pigment content in solid content: 60%) | 33.34 parts by mass |
| Colorant (dispersion of C.I. Pigment Yellow 139) (solid content: 15% by mass pigment content in solid content 60%) | 22.23 parts by mass |
| Radical polymerizable monomer (polymerizable compound) (mixture of 3:7 of pentaerythritol triacrylate and dipentaerythritol hexaacrylate) | 2.5 parts by mass |
| Specific Compound 1 (specific oxime compound) | 0.5 part by mass |
| Benzyl methacrylate/methacrylic acid copolymer (molar ratio = 70/30) | 2.0 parts by mass |

Example 3-36 to Example 3-51, and Comparative Example 3-7 to Comparative Example 3-9

Colored photopolymerizable compositions D-2 to D-17, and D'-1 to D'-3 were respectively produced in the same manner as in Example 3-35, except that 0.5 part by mass of Specific Compound 1 (specific oxime compound) included in the composition D-1, which was used in the preparation of the colored photopolymerizable composition D-1 in Example 3-35, was replaced with the compounds and the amounts as shown in the following Tables 5A and 5B, respectively, and, furthermore, the sensitizers and co-sensitizers, of which kinds and amounts are shown in Tables 5A and 5B, were added in Example 3-44 to 3-61.

The obtained colored photopolymerizable compositions were each evaluated in a manner similar to that in Example 3-1. The results are shown in Tables 5A and 5B.

TABLE 5A

| | Colored polymerizable composition | Polymerization initiator | | | Sensitizer | | Co-sensitizer | |
|---|---|---|---|---|---|---|---|---|
| | | Specific compound | Comparative compound | Content (parts by mass) | Kind | Content (parts by mass) | Kind | Content (parts by mass) |
| Example 3-35 | D-1 | 1 | — | 0.5 | — | — | — | — |
| Example 3-36 | D-2 | 2 | — | 0.5 | — | — | — | — |
| Example 3-37 | D-3 | 3 | — | 0.5 | — | — | — | — |
| Example 3-38 | D-4 | 4 | — | 0.5 | — | — | — | — |
| Example 3-39 | D-5 | 5 | — | 0.5 | — | — | — | — |
| Example 3-40 | D-6 | 6 | — | 0.5 | — | — | — | — |
| Example 3-41 | D-7 | 7 | — | 0.5 | — | — | — | — |
| Example 3-42 | D-8 | 8 | — | 0.5 | — | — | — | — |
| Example 3-43 | D-9 | 9 | — | 0.5 | — | — | — | — |

TABLE 5A-continued

| | Colored polymerizable composition | Polymerization initiator | | | Sensitizer | | Co-sensitizer | |
|---|---|---|---|---|---|---|---|---|
| | | Specific compound | Comparative compound | Content (parts by mass) | Kind | Content (parts by mass) | Kind | Content (parts by mass) |
| Example 3-44 | D-10 | 2 | — | 0.4 | A-1 | 0.1 | — | — |
| Example 3-45 | D-11 | 2 | — | 0.4 | A-2 | 0.1 | — | — |
| Example 3-46 | D-12 | 2 | — | 0.4 | A-3 | 0.1 | — | — |
| Example 3-47 | D-13 | 2 | — | 0.4 | — | — | F1 | 0.1 |
| Example 3-48 | D-14 | 2 | — | 0.3 | A-2 | 0.1 | F1 | 0.1 |
| Example 3-49 | D-15 | 2 | — | 0.3 | A-2 | 0.1 | F2 | 0.1 |
| Example 3-50 | D-16 | 2 | — | 0.3 | A-2 | 0.1 | F3 | 0.1 |
| Example 3-51 | D-17 | 2 | — | 0.3 | — | — | F3 LD-5 | 0.1 0.1 |
| Comp. example 3-7 | D'-1 | — | 1 | 0.5 | — | — | — | — |
| Comp. Example 3-8 | D'-2 | — | 2 | 0.5 | — | — | — | — |
| Comp. Example 3-9 | D'-3 | — | 3 | 0.5 | — | — | — | — |

TABLE 5B

| | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-35 | A | 1,500 | 1.96 | A | A | A | Rectangular | Rectangular |
| Example 3-36 | A | 1,400 | 1.96 | A | A | A | Rectangular | Rectangular |
| Example 3-37 | A | 1,400 | 1.96 | A | A | A | Rectangular | Rectangular |
| Example 3-38 | A | 1,400 | 1.96 | A | A | A | Rectangular | Rectangular |
| Example 3-39 | A | 1,400 | 1.96 | A | A | A | Rectangular | Rectangular |
| Example 3-40 | A | 1,400 | 1.96 | A | A | A | Rectangular | Rectangular |
| Example 3-41 | A | 1,600 | 1.94 | A | A | A | Rectangular | Rectangular |
| Example 3-42 | A | 1,400 | 1.96 | A | A | A | Rectangular | Rectangular |
| Example 3-43 | A | 1,400 | 1.96 | A | A | A | Rectangular | Rectangular |
| Example 3-44 | A | 1,300 | 1.96 | A | A | A | Rectangular | Rectangular |
| Example 3-45 | A | 1,300 | 1.96 | A | A | A | Rectangular | Rectangular |
| Example 3-46 | A | 1,300 | 1.96 | A | A | A | Rectangular | Rectangular |
| Example 3-47 | A | 1,300 | 1.96 | A | A | A | Rectangular | Rectangular |
| Example 3-48 | A | 1,300 | 1.96 | A | A | A | Rectangular | Rectangular |
| Example 3-49 | A | 1,300 | 1.96 | A | A | A | Rectangular | Rectangular |
| Example 3-50 | A | 1,200 | 1.96 | A | A | A | Rectangular | Rectangular |
| Example 3-51 | A | 1,200 | 1.96 | A | A | A | Rectangular | Rectangular |

TABLE 5B-continued

|  | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Comp. example 3-7 | A | 3,000 | 1.92 | A | B | C | Reverse tapered | Forward tapered |
| Comp. Example 3-8 | A | 2,800 | 1.92 | A | C | C | Reverse tapered | Forward tapered |
| Comp. Example 3-9 | A | 2,800 | 1.92 | A | A | B | Reverse tapered | Forward tapered |

The sensitizers A1 to A3, the co-sensitizers F1 to F3, and LD-5 as shown in Tables 5A and 5B are the aforementioned compounds.

The results of Tables 3A to 5B show that the colored photopolymerizable composition in each Example containing a specific oxime compound (Specific Compound 1 to Specific Compound 9) is excellent in the storage stability (stability with the passage of time). Further, it can be seen that these colored photopolymerizable compositions have high exposure sensitivity, are excellent in the developability when used for forming a colored pattern of a color filter, do not cause coloration due to heat-aging of the obtained colored pattern, and are excellent in the adhesion to the substrate, the pattern cross-sectional profile, and the post-heating pattern cross-sectional profile.

Moreover, it is can be seen from Tables 5A and 5B that excellent exposure sensitivity can be obtained, even when the content of pigment is high.

Examples 4-1 to 4-38, and Comparative Examples 4-1 to a 4-12

Preparation of Black Photopolymerizable Composition

Preparation of Carbon Black Dispersion A

The following composition 1 was subjected to a high viscous dispersing processing using two rolls to obtain a dispersion. At this time, the viscosity of the dispersion was 70,000 mPa·s.

Thereafter, the following composition 2 was added to this dispersion, and the mixture was stirred under the condition of 3,000 rpm by using a homogenizer for 3 hours. The obtained mixed solution was subjected to a dispersing processing using a dispersing machine (trade name: DISPERMAT; manufactured by Getzmann GmbH) using 0.3 mm zirconia beads for 4 hours, thereby preparing Carbon Black Dispersion A (hereinafter, denoted as CB Dispersion A). At this time, the viscosity of the mixed solution was 37 mPa·s.

| Composition 1 | |
|---|---|
| Carbon black (Pigment Black 7) having an average primary particle diameter of 15 nm | 23 parts by mass |
| Solution (45%) of propylene glycol monomethylether acetate of copolymer of benzyl methacrylate/ methacrylic acid (BzMA/MAA = 70/30; Mw: 30,000) | 22 parts by mass |
| SOLSPERSE 5000 (manufactured by Zeneca Co., Ltd.) | 1.2 parts by mass |

| Composition 2 | |
|---|---|
| Solution (45%) of propylene glycol monomethylether acetate of copolymer of benzyl methacrylate/ methacrylic acid (BzMA/MAA = 70/30; Mw: 30,000) | 22 parts by mass |
| Propylene glycol monomethylether acetate | 200 parts by mass |

Preparation of Titanium Black Dispersion A

The following composition 3 was subjected to a high viscous dispersing processing using two rolls to obtain a dispersion. At this time, the viscosity of the dispersion was 40,000 mPa·s.

Prior to the high viscous dispersing processing, kneading may be carried out using a kneader for 30 minutes.

| Composition 3 | |
|---|---|
| Titanium black 13M-C having a primary average particle diameter of 75 nm (Pigment Black 35; manufactured by Mitsubishi Materials Corporation) | 39 parts by mass |
| Propylene glycol monomethylether acetate solution of copolymer of benzyl (meth)acrylate/(meth)acrylic acid (BzMA/MAA = 70/30; Mw: 30,000; solid content: 40% by mass) | 8 parts by mass |
| SOLSPERSE 5000 (manufactured by Zeneca Co., Ltd.) | 1 part by mass |

The following component 4 was added to the obtained dispersion, and the mixture was stirred under the condition of 3,000 rpm by using a homogenizer for 3 hours. The obtained mixed solution was subjected to a dispersing processing using a dispersing machine (trade name: DISPERMAT; manufactured by Getzmann GmbH) using 0.3 mm zirconia beads for 4 hours, thereby preparing Titanium Black Dispersion A (hereinafter, denoted as TB Dispersion A). At this time, the viscosity of the mixed solution was 7.0 mPa·s.

| Composition 4 | |
| --- | --- |
| Propylene glycol monomethylether acetate solution of copolymer of benzyl (meth)acrylate/(meth)acrylic acid (BzMA/MAA = 70/30; Mw: 30,000; solid content: 40% by mass) | 8 parts by mass |
| Propylene glycol monomethylether acetate | 200 parts by mass |

Preparation of Black Photopolymerizable Compositions E-1 to E-18, and E'-1 to E'-6

The components of following composition E-a were mixed using a stirrer, and the black photopolymerizable compositions E-1 to E-18 and E'-1 to E'-6 were prepared.

| Composition E-a | |
| --- | --- |
| Methacrylate/acrylic acid copolymer (alkali-soluble resin) | 1.6 part by mass |
| Dipentaerythritol hexaacrylate | 2.3 parts by mass |
| Ethoxylated pentaerythritol tetraacrylate | 0.8 part by mass |
| CB Dispersion A or TB Dispersion A described above | 24 parts by mass |
| Propylene glycol monomethylether acetate | 10 parts by mass |
| Ethyl-3-ethoxypropionate | 8 parts by mass |
| Compound recited in the following Tables 6A and 6B: specific oxime compound or comparative compound: | quantities recited in Tables 6A and 6B |
| Co-sensitizer: F3 | not added or 0.1 part by mass |

Preparation of Black Photopolymerizable Compositions E-19 to E-38, and E'-7 to E'-12

The components of following composition E-b were mixed using a stirrer, and black photopolymerizable compositions E-19 to E-38 and E'-7 to E'-12 were prepared.

| Composition E-b | |
| --- | --- |
| Dipentaerythritol hexaacrylate | 2.3 part by mass |
| CB Dispersion A or TB Dispersion A described above | 24 parts by mass |
| Propylene glycol monomethylether acetate | 10 parts by mass |
| Ethyl-3-ethoxypropionate | 8 parts by mass |
| Compound recited in the following Tables 7A and 7B: specific oxime compound or comparative compound: | quantities recited in Table 7A and 7B |
| Co-sensitizer: F3 | not added or 0.1 part by mass |

Evaluations

The following evaluations were performed using the black photopolymerizable compositions E-1 to E-38 and E'-1 to E'-12 obtained in the above manner. The results are collectively shown in Tables 6A and 6B, and Tables 7A and 7B.

Exposure Sensitivity Evaluation

The exposure sensitivities of the black photopolymerizable compositions E-1 to E-38 and E'-1 to E'-12 obtained in the above manner were determined and evaluated by the following methods.

The black photopolymerizable compositions E-1 to E-38 and E'-1 to E'-12 each were used, and were uniformly applied on a silicon wafer in such a manner that a number of revolutions of spin coating was adjusted so as to attain a film thickness of 1.0 μm after the heat processing, using a hot plate having a surface temperature of 120° C. for 120 seconds, thereby obtaining a coated film having a thickness of 1 μm.

Subsequently, the coated film was irradiated with light through a mask having a L&S (line and space) pattern of 10 nm, using an i-line stepper exposure machine FPA-3000i5+ (manufactured by Canon Inc.) with an exposure amount in the range of from 100 to 5,100 mJ/cm$^2$ in increments of 100 mJ/cm$^2$.

After the irradiation, paddle development was performed using a 0.3% aqueous solution of tetramethyl ammonium hydroxide (TMAH) at 23° C. for 60 seconds. Thereafter, the coated wafer was rinsed with pure water using a spin shower for 20 seconds, and was further washed with pure water. Then, water droplets adhered to the board were removed with high air and the substrate was naturally dried, thereby obtaining a black image pattern.

The obtained colored image patterns each were evaluated by using an optical microscope in accordance with the following criteria.

The exposure sensitivity was evaluated by defining the minimum exposure amount that achieves a film thickness after development in the area irradiated with light in the exposure process of 95% or more relative to the film thickness 100% before the exposure, as the exposure sensitivity. It means that the sensitivity is higher as the value of exposure sensitivity is smaller.

Evaluation of Storage Stability (Stability with Passage of Time)

The storage stability (stability with the passage of time) of the black photopolymerizable compositions E-1 to E-38 and E'-1 to E'-12 obtained in the above was evaluated according the following method.

That is, after the colored photopolymerizable compositions E-1 to E-38 and E'-1 to E'-12 were each stored for one month at room temperature, the degree of deposition of foreign matters was visually inspected and evaluated in accordance with the following evaluation criteria:

Evaluation Criteria

A: No deposition was recognized;

B: deposition was slightly recognized; and

C: deposition was recognized.

Evaluation of Developability

Further, the developability of the black photopolymerizable compositions E-1 to E-38 and E'-1 to E'-12 each were evaluated in the following manner.

That is, the developability was evaluated by observing whether or not residues were present in the area where light was not irradiated (unexposed portion) in the exposure process. The evaluation criteria are as follows.

Evaluation Criteria

A: no residues in the unexposed area were recognized at all;

B: residues in the unexposed area were slightly recognized, but were not at a level of being problematic in practical use; and C: residues were remarkably recognized in the unexposed area.

TABLE 6A

| Black photo-polymerizable composition | Com-position | Dispersion | Polymerization initiator Specific compound | Polymerization initiator Com-parative compound | Polymerization initiator Content (parts by mass) | Co-sensitizer Kind | Co-sensitizer Content (mass by parts) | Exposure sensitivity (mJ/cm$^2$) | Storage storability | Develop-ability |
|---|---|---|---|---|---|---|---|---|---|---|
| Example 4-1 | E-1 | E-a | CB Dispersion A | 1 | — | 0.8 | — | — | 200 | A | A |
| Example 4-2 | E-2 | E-a | CB Dispersion A | 2 | — | 0.8 | — | — | 100 | A | A |
| Example 4-3 | E-3 | E-a | CB Dispersion A | 3 | — | 0.8 | — | — | 100 | A | A |
| Example 4-4 | E-4 | E-a | CB Dispersion A | 4 | — | 0.8 | — | — | 100 | A | A |
| Example 4-5 | E-5 | E-a | CB Dispersion A | 5 | — | 0.8 | — | — | 100 | A | A |
| Example 4-6 | E-6 | E-a | CB Dispersion A | 6 | — | 0.8 | — | — | 100 | A | A |
| Example 4-7 | E-7 | E-a | CB Dispersion A | 7 | — | 0.8 | — | — | 100 | A | A |
| Example 4-8 | E-8 | E-a | CB Dispersion A | 8 | — | 0.7 | — | — | 300 | A | A |
| Example 4-9 | E-9 | E-a | CB Dispersion A | 9 | — | 0.7 | — | — | 200 | A | A |
| Example 4-10 | E-10 | E-a | CB Dispersion A | 1 | — | 0.1 | F3 | 0.1 | 80 | A | A |
| Example 4-11 | E-11 | E-a | TB Dispersion A | 1 | — | 0.8 | — | — | 200 | A | A |
| Example 4-12 | E-22 | E-a | TB Dispersion A | 2 | — | 0.8 | — | — | 100 | A | A |
| Example 4-13 | E-13 | E-a | TB Dispersion A | 3 | — | 0.8 | — | — | 200 | A | A |
| Example 4-14 | E-14 | E-a | TB Dispersion A | 4 | — | 0.8 | — | — | 200 | A | A |
| Example 4-15 | E-15 | E-a | TB Dispersion A | 7 | — | 0.8 | — | — | 400 | A | A |
| Example 4-16 | E-16 | E-a | TB Dispersion A | 8 | — | 0.8 | — | — | 200 | A | A |
| Example 4-17 | E-17 | E-a | TB Dispersion A | 9 | — | 0.8 | — | — | 200 | A | A |
| Example 4-18 | E-18 | E-a | TB Dispersion A | 1 | — | 0.7 | F3 | 0.1 | 150 | A | A |

TABLE 6B

| Black photo-polymerizable composition | Com-position | Dispersion | Polymerization initiator Specific compound | Polymerization initiator Comparative compound | Polymerization initiator Content (parts by mass) | Co-sensitizer Kind | Co-sensitizer Content (mass by parts) | Exposure sensitivity (mJ/cm$^2$) | Storage storability | Develop-ability |
|---|---|---|---|---|---|---|---|---|---|---|
| Comparative Example 4-1 | E'-1 | E-a | CB Dispersion A | — | 1 | 0.8 | — | — | 600 | A | A |
| Comparative Example 4-2 | E'-2 | E-a | CB Dispersion A | — | 2 | 0.8 | — | — | 500 | A | A |
| Comparative Example 4-3 | E'-3 | E-a | CB Dispersion A | — | 3 | 0.8 | — | — | 500 | A | A |
| Comparative Example 4-4 | E'-4 | E-a | TB Dispersion A | — | 1 | 0.8 | — | — | 800 | A | A |
| Comparative Example 4-5 | E'-5 | E-a | TB Dispersion A | — | 2 | 0.8 | — | — | 700 | A | A |
| Comparative Example 4-6 | E'-6 | E-a | TB Dispersion A | — | 3 | 0.8 | — | — | 700 | A | A |

TABLE 7A

| Black photo-polymerizable composition | Com-posi-tion | Dispersion | Polymerization initiator Specific com-pound | Polymerization initiator Comparative compound | Polymerization initiator Content (parts by mass) | Co-sensitizer Kind | Co-sensitizer Content (mass by parts) | Exposure sensitivity (mJ/cm$^2$) | Storage storability | Develop-ability |
|---|---|---|---|---|---|---|---|---|---|---|
| Example 4-19 | E-19 | E-b | CB Dispersion A | 1 | — | 0.8 | — | — | 500 | A | A |
| Example 4-20 | E-20 | E-b | CB Dispersion A | 2 | — | 0.8 | — | — | 400 | A | A |
| Example 4-21 | E-21 | E-b | CB Dispersion A | 3 | — | 0.8 | — | — | 400 | A | A |
| Example 4-22 | E-22 | E-b | CB Dispersion A | 4 | — | 0.8 | — | — | 400 | A | A |
| Example 4-23 | E-23 | E-b | CB Dispersion A | 5 | — | 0.8 | — | — | 400 | A | A |
| Example 4-24 | E-24 | E-b | CB Dispersion A | 6 | — | 0.8 | — | — | 400 | A | A |
| Example 4-25 | E-25 | E-b | CB Dispersion A | 7 | — | 0.8 | — | — | 700 | A | A |
| Example 4-26 | E-26 | E-b | CB Dispersion A | 8 | — | 0.8 | — | — | 400 | A | A |
| Example 4-27 | E-27 | E-b | CB Dispersion A | 9 | — | 0.8 | — | — | 400 | A | A |
| Example 4-28 | E-28 | E-b | CB Dispersion A | 2 | — | 0.7 | F3 | 0.1 | 300 | A | A |
| Example 4-29 | E-29 | E-b | TB Dispersion A | 1 | — | 0.8 | — | — | 300 | A | A |
| Example 4-30 | E-30 | E-b | TB Dispersion A | 2 | — | 0.8 | — | — | 200 | A | A |
| Example 4-31 | E-31 | E-b | TB Dispersion A | 3 | — | 0.8 | — | — | 200 | A | A |
| Example 4-32 | E-32 | E-b | TB Dispersion A | 4 | — | 0.8 | — | — | 200 | A | A |
| Example 4-33 | E-33 | E-b | TB Dispersion A | 5 | — | 0.8 | — | — | 200 | A | A |
| Example 4-34 | E-34 | E-b | TB Dispersion A | 6 | — | 0.8 | — | — | 200 | A | A |
| Example 4-35 | E-35 | E-b | TB Dispersion A | 7 | — | 0.8 | — | — | 400 | A | A |

TABLE 7B

| | Black photo-polymerizable composition | Composition | Dispersion | Polymerization initiator Specific compound | Comparative compound | Content (parts by mass) | Co-sensitizer Kind | Content (mass by parts) | Exposure sensitivity (mJ/cm$^2$) | Storage storability | Developability |
|---|---|---|---|---|---|---|---|---|---|---|---|
| Example 4-36 | E-36 | E-b | TB Dispersion A | 8 | — | 0.8 | — | — | 200 | A | A |
| Example 4-37 | E-37 | E-b | TB Dispersion A | 9 | — | 0.8 | — | — | 200 | A | A |
| Example 4-38 | E-38 | E-b | TB Dispersion A | 2 | — | 0.7 | F3 | 0.1 | 150 | A | A |
| Comparative Example 4-7 | E'-7 | E-b | CB Dispersion A | — | 1 | 0.8 | — | — | 900 | A | B |
| Comparative Example 4-8 | E'-8 | E-b | CB Dispersion A | — | 2 | 0.8 | — | — | 800 | A | B |
| Comparative Example 4-9 | E'-9 | E-b | CB Dispersion A | — | 3 | 0.8 | — | — | 800 | A | A |
| Comparative Example 4-10 | E'-10 | E-b | TB Dispersion A | — | 1 | 0.8 | — | — | 600 | A | B |
| Comparative Example 4-11 | E'-11 | E-b | TB Dispersion A | — | 2 | 0.8 | — | — | 600 | A | B |
| Comparative Example 4-12 | E'-12 | E-b | TB Dispersion A | — | 3 | 0.8 | — | — | 600 | A | A |

As is clear from the results shown in Tables 6A to 7B, the black photopolymerizable composition in each Example containing the specific oxime compound is excellent in the storage stability (stability with the passage of time). Further, it can be seen that these black photopolymerizable compositions have high exposure sensitivity as compared with Comparative Examples, and are excellent in the developability of unexposed areas, so that a good black pattern (colored pattern) can be formed even if exposure amount is small.

Example 5

Manufacture of Full-Color Color Filter

The black image pattern produced in Example 4-1 was used as a black matrix, and a green (G) colored pattern of 1.6×1.6 μm was formed, by using the colored photopolymerizable composition A-1, on the black matrix in the same manner as the method recited in Example 3-1.

Further, only the pigment (30/70 (mass ratio) mixture of C. I. Pigment Green 36 and C. I. Pigment Yellow 219) in the colored photopolymerizable composition A-1 was changed to a blue pigment (30/70 (mass ratio) mixture of C.I. Pigment Blue 15:6 and C.I. Pigment Violet 23), and a red pigment (C.I. Pigment Red 254), respectively, and others were unchanged, so that colored photopolymerizable compositions of blue (B) and red (R) were prepared, respectively.

A blue color (B) pattern and a red color (R) pattern each having a 1.6×1.6 μm size were sequentially formed on the substrate, thereby manufacturing a color filter for a solid-state imaging device.

Regarding the obtained color filter, the cross-sectional profiles and the adhesion to substrate of the black image pattern and the R, G and B colored patterns were each evaluated in the same manner as that in Example 2-1. As a result, it turned out that the patterns each had a rectangular profile, no pattern defects, and excellent adhesion to substrate.

Example 6

Manufacture of Solid-State Imaging Device

When the full-color color filter obtained in Example 5 was mounted to a solid-state imaging device, it turned out that the solid-state imaging device with the color filter exerts high resolution and excellent color separation property.

Examples 7-1 to 7-15, and Comparative Examples 7-1 to 7-4

Manufacture of Support

After the surface of an aluminum plate with 1S material grade having a thickness of 0.30 mm was subjected to graining with an 800-mesh pumice stone aqueous suspension by using a nylon brush (No. 8), the surface was sufficiently washed with water. After the plate was immersed and etched in a 10% aqueous sodium hydroxide solution at 70° C. for 60 seconds, the plate was washed with running water, followed by neutralization with 20% HNO$_3$ and washing with water. The aluminum plate was subjected to an electrolytic graining in a 1% aqueous nitric acid solution by using sine wave alternate waveform current under the condition of VA=12.7 V with the quantity of electricity of 300 coulomb/dm$^2$ at an anode. The surface roughness measured was 0 to 45 μm (Ra expression). Subsequently, after the aluminum plate was immersed in a 30% H$_2$SO$_4$ aqueous solution, and was desumutted at 55° C. for 2 minutes, a cathode was arranged at the grained surface and the plate was subjected to anodic oxidation at a current density of 5 A/dm$^2$ for 50 seconds, in a 20% H$_2$SO$_4$ aqueous solution at 33° C., whereby a thickness of 2.7 g/m$^2$ was obtained.

In this way, Support A-1 for planographic printing plate precursor was obtained.

Formation of Photosensitive Layer

On the obtained support, a photosensitive layer was formed by applying a coating liquid for a photosensitive layer, which has the following composition, and drying the coated layer at 95° C. so as to attain a dry coating amount of 1.4 g/m$^2$.

| Composition of coating liquid for photosensitive layer | |
|---|---|
| Addition-polymerizable compound (M, N or O recited in Table 8) | 0.80 part by mass |
| Binder polymer (B1, B2, or B3 recited in Table 8) | 0.90 part by mass |
| Sensitizer (A1, A2, or A3 recited in Table 8) | not added, or 0.10 part by mass |
| Compound recited in the following Table 8: specific oxime compound, comparative compound, or LD-5 | 0.05 part by mass |
| Co-sensitizer (the above F2 or F3 recited in Table 8) | not added, or 0.25 part by mass |

-continued

| Composition of coating liquid for photosensitive layer | |
|---|---|
| Fluorine-containing surfactant (MEGAFAC F-177; manufactured by DIC Corporation) | 0.02 part by mass |
| Thermal-polymerization inhibitor (N-nitrosohydroxylamine aluminum salt) | 0.03 part by mass |
| ε-type copper phthalocyanine dispersion | 0.2 part by mass |
| Methyl ethyl ketone | 16.0 parts by mass |
| Propylene glycol monomethylether | 16.0 parts by mass |

Formation of Protective Layer

On the obtained photosensitive layer, a 3% by mass aqueous solution of a polyvinyl alcohol (saponification degree of 98% by mol and polymerization degree of 550) was applied, and was dried at 100° C. for 2 minutes so as to attain a dry coating amount of 2 g/m², thereby forming a protective layer.

In this way, planographic printing plate precursors of Examples and planographic printing plate precursors of Comparative Examples were obtained.

Plate-Making

The planographic printing plate precursors were subjected to the following exposure and development processing.

Exposure

Solid images and 1- to 99-% dot images (in increments of 1%) were formed by scan-exposing the planographic printing plate precursor with an exposure amount of 50 μJ/cm² using a violet LD (VIOLET BOXER manufactured by FFEI Ltd.) at a wavelength of 405 nm, under the conditions of 4,000 dpi and 175 lines/inch.

Development

The planographic printing plate precursor was subjected to a standard processing by using an automatic developing machine (LP-850P2; manufactured by FujiFilm Corporation), in which the following developer 1 and a finishing gum liquid "PF-2W" (manufactured by FujiFilm Corporation) were placed. The condition of preheating was the achieving temperature to the plate surface of 100° C., the temperature of developer was 30° C., and the immersion time in the developer was about 15 seconds.

The developer 1 has the following composition, pH was 11.5 at 25° C., and the electroconductivity was 5 mS/cm.

| Composition of developer 1 | |
|---|---|
| Potassium hydroxide | 0.15 g |
| Polyoxyethylene phenyl ether (n = 13) | 5.0 g |
| CHELEST 400 (chelating agent) | 0.1 g |
| Water | 94.75 g |

Evaluation

The sensitivity, the storage stability, and the printing durability of the formed image areas of Examples and Comparative Examples were evaluated in the following methods. The results are collectively shown in Table 8.

1. Evaluation of Sensitivity

The planographic printing plate precursor was exposed to light under the above conditions, and was developed under the above conditions immediately after the light exposure, thereby forming an image. The percentage of area of 50% halftone dots of the formed image was measured using a dot meter (manufactured by Gretag/Macbeth). This shows that the sensitivity is higher as the numeral value increases.

2. Test for Printing Durability of Image Area

Printing with the use of the planographic printing plate precursor was performed using "R201" manufactured by Roland as a printing machine, and "GEOS-G(N)" manufactured by DIC Corporation, as an ink. By observing the printed product on which a solid image area was printed, the printing durability was estimated based on the number of printed sheets when faint printing of images begins to take place. This shows that the printing durability is higher as the numeral value becomes larger.

3. Evaluation of the Amount of Change in Forced Aging (Storage Stability)

The measurement of the halftone dot area was carried out in a manner similar to the evaluation of the sensitivity, except that the planographic printing plate precursors, which were sealed together with interleaf paper in aluminum kraft paper and allowed to stand at 60° C. for 4 days, were used. Next, the difference in halftone dot area between the printing plate, which was allowed to stand at 60° C. for 4 days and the printing plate which was not allowed to stand at 60° C. for 4 days, was obtained, and the variation in the dot percentage (Δ %) due to the forced aging was measured. This shows that the influence exerted by the forced aging is small with a decrease in the absolute numeral value, namely, the storage stability is high.

TABLE 8

| | | Photosensitive layer | | | | | | Sensitivity | | Image |
|---|---|---|---|---|---|---|---|---|---|---|
| | Support | Specific compound or comparative compound | Addition polymerizable compound | Binder polymer | Sensitizer | Co-sensitizer | Coating amount (g/m²) | (%) (50% dot percentage) | Variation in forced aging | area print durability test |
| Example 7-1 | A-1 | Specific Compound 1 | M | B1 | — | — | 1.4 | 56 | 2.0 | 70000 |
| Example 7-2 | A-1 | Specific Compound 2 | M | B1 | — | — | 1.4 | 56 | 2.0 | 70000 |
| Example 7-3 | A-1 | Specific Compound 3 | M | B1 | — | — | 1.4 | 56 | 2.0 | 60000 |
| Example 7-4 | A-1 | Specific Compound 4 | M | B1 | — | — | 1.4 | 55 | 2.0 | 60000 |
| Example 7-5 | A-1 | Specific Compound 5 | M | B1 | — | — | 1.4 | 56 | 2.0 | 70000 |
| Example 7-6 | A-1 | Specific Compound 6 | M | B1 | — | — | 1.4 | 56 | 2.0 | 70000 |
| Example 7-7 | A-1 | Specific Compound 7 | M | B1 | — | — | 1.4 | 56 | 2.0 | 70000 |
| Example 7-8 | A-1 | Specific Compound 8 | M | B1 | — | — | 1.4 | 54 | 2.0 | 55000 |
| Example 7-9 | A-1 | Specific Compound 9 | M | B1 | — | — | 1.4 | 55 | 2.0 | 60000 |
| Example 7-10 | A-1 | Specific Compound 2 | M | B1 | A1 | F2 | 1.4 | 55 | 2.0 | 70000 |
| Example 7-11 | A-1 | Specific Compound 2 | N | B2 | A1 | F2 | 1.4 | 55 | 2.0 | 70000 |
| Example 7-12 | A-1 | Specific Compound 2 | O | B3 | A1 | F2 | 1.4 | 55 | 2.0 | 100000 |
| Example 7-13 | A-1 | Specific Compound 2 | O | B3 | A2 | F2 | 1.4 | 57 | 2.0 | 100000 |
| Example 7-14 | A-1 | Specific Compound 2 | O | B3 | A3 | F3 | 1.4 | 58 | 2.0 | 100000 |
| Example 7-15 | A-1 | Specific Compound 2 | O | B3 | A3 | F3 | 1.4 | 60 | 2.0 | 100000 |
| Comparative Example 7-1 | A-1 | Comparative Compound 1 | M | B1 | — | — | 1.4 | 50 | 2.0 | 40000 |

TABLE 8-continued

| | Support | Specific compound or comparative compound | Photosensitive layer | | | | | Sensitivity | | Image |
| | | | Addition polymerizable compound | Binder polymer | Sensitizer | Co-sensitizer | Coating amount (g/m$^2$) | (%) (50% dot percentage) | Variation in forced aging | area print durability test |
|---|---|---|---|---|---|---|---|---|---|---|
| Comparative Example 7-2 | A-1 | Comparative Compound 2 | M | B1 | — | — | 1.4 | 51 | 2.0 | 40000 |
| Comparative Example 7-3 | A-1 | Comparative Compound 3 | M | B1 | — | — | 1.4 | 51 | 2.0 | 40000 |
| Comparative Example 7-4 | A-1 | LD-5 | M | B1 | A1 | F2 | 1.4 | 53 | 2.0 | 50000 |

In Table 8, the details of M, N, and O shown in the column of "addition polymerizable compound", and B1, B2, and B3 shown in the column of "binder polymer" are described below. In addition, the following B3 is a mixture (mixing ratio: 50/50 (molar ratio)) of a copolymer of MDI/HMDI (molar ratio: 80/20) and a copolymer (molar ratio: 52/22/26) of the following structures of DMPA, PPG (m=3), and TEG.

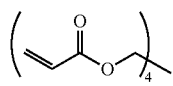
M

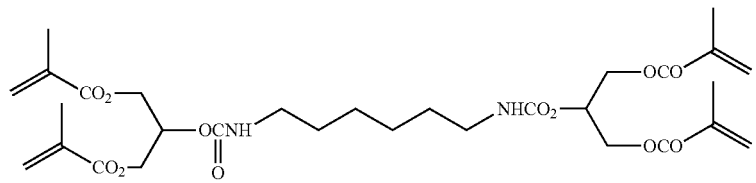
N

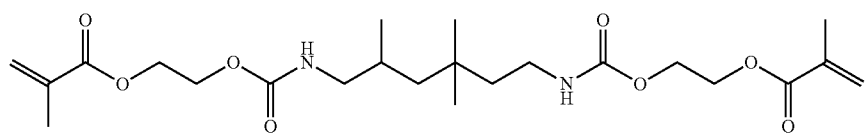

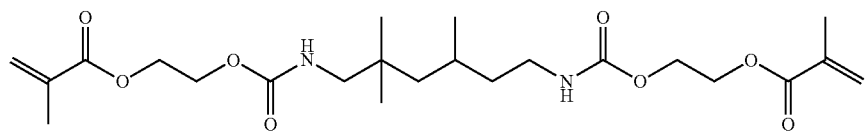
O (Isomeric mixture of these)

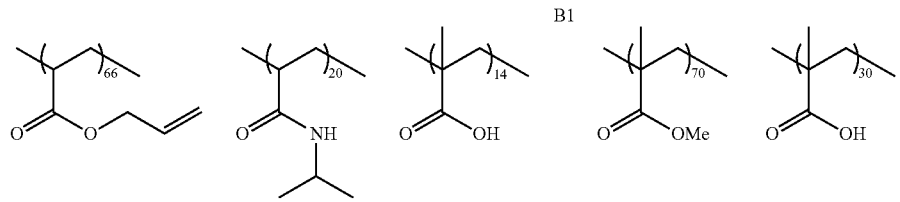
B1 B2

-continued

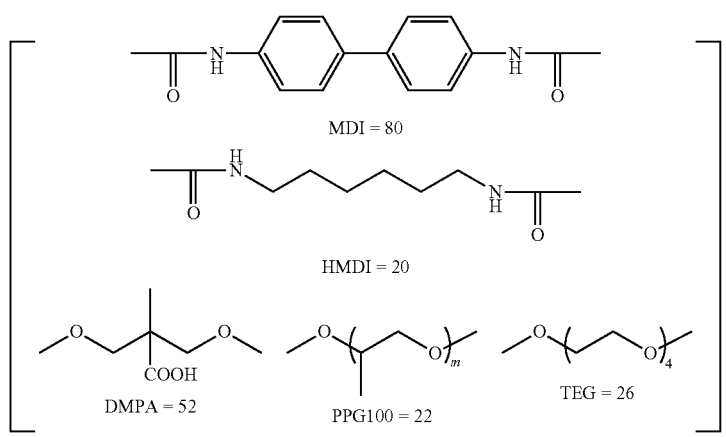

It can be seen from FIG. 8 that the planographic printing plate precursors of Examples 7-1 to 7-15, whose photosensitive layers each contain the specific oxime compound of the invention, are highly sensitive, and exert excellent storage stability and excellent printing durability.

On the other hand, the planographic printing plate precursors of Comparative Examples 7-1 to 7-4 are inferior to the planographic printing plate precursors in Examples in both the sensitivity and the printing durability.

The invention claimed is:

1. A polymerizable composition comprising:
(A) an oxime polymerization initiator comprising: a condensed ring formed by including two or more rings selected from an aromatic ring and a heterocyclic ring; and a cyclic structure which is connected to the condensed ring, the cyclic structure comprising a carbonyl group and having an oxime group directly connected to the carbonyl group; and
(B) a polymerizable compound, wherein (A) the oxime polymerization initiator comprises a compound represented by the following Formula (1):

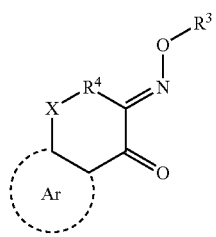

wherein, in Formula (1), Ar represents a condensed ring formed by including two or more rings selected from an aromatic ring and a heterocyclic ring; X represents a carbon atom, an oxygen atom, a sulfur atom or a nitrogen atom; $R^3$ represents an acyl group or a sulfonyl group; and $R^4$ represents —(CHR)n-, wherein R represents a hydrogen atom, an alkyl group, or an aromatic ring group, and n represents an integer of from 0 to 2.

2. The polymerizable composition according to claim 1, further comprising (C) a colorant.

3. The polymerizable composition according to claim 1, wherein the polymerizable composition is used for forming a colored area in a color filter.

4. A color filter comprising:
a support; and
a colored area formed by using the polymerizable composition according to claim 1, on the support.

5. A solid-state imaging device, comprising the color filter according to claim 4.

6. A method of producing a color filter, comprising:
applying the polymerizable composition according to claim 1 to a support to form a polymerizable composition layer;
subjecting the polymerizable composition layer to pattern exposure; and
developing the polymerizable composition layer after the exposure to form a colored pattern.

7. A planographic printing plate precursor, comprising:
a support; and
a photosensitive layer comprising the polymerizable composition according to claim 1, on the support.

8. A polymerizable composition comprising:
(A) an oxime polymerization initiator comprising: a condensed ring formed by including two or more rings selected from an aromatic ring and a heterocyclic ring; and a cyclic structure which is connected to the condensed ring, the cyclic structure comprising a carbonyl group and having an oxime group directly connected to the carbonyl group; and
(B) a polymerizable compound, wherein (A) the oxime polymerization initiator comprises a compound represented by the following Formula (1A) or the following Formula (1B):

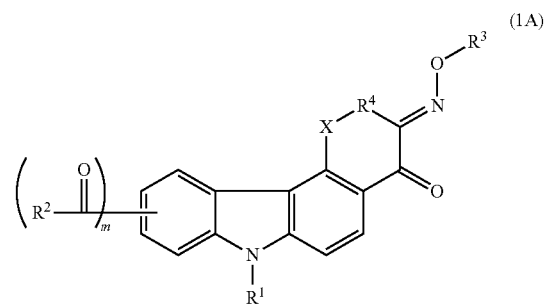

-continued (1B)

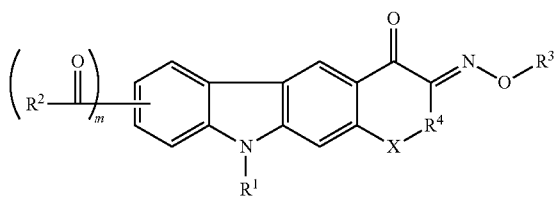

wherein, in Formulae (1A) and (1B), $R^1$ and $R^2$ each independently represents an alkyl group, an aryl group or a heterocyclic group; $R^3$ represents an acyl group or a sulfonyl group; $R^4$ represents —(CHR)n-, wherein R represents a hydrogen atom, an alkyl group or an aromatic ring group, and n represents an integer of from 0 to 2; m represents 0 or 1; and X represents a carbon atom, an oxygen atom, a sulfur atom or a nitrogen atom.

9. The polymerizable composition according to claim 8, wherein $R^2$ in Formula (1A) and Formula (1B) is a substituent represented by the following Formula (2):

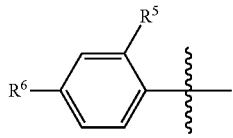

(2)

wherein, in Formula (2), $R^5$ and $R^6$ each independently represents a hydrogen atom, a halogen atom, an alkyl group, an aryl group, a hydroxyl group, a thiol group, an amino group, a morpholino group, an alkyloxycarbonyl group, an acyloxy group, an alkoxy group, an alkylthio group, or an alkylseleno group.

10. The polymerizable composition according to claim 8, further comprising (C) a colorant and (D) a pigment dispersant, wherein (C) the colorant is a pigment.

11. The polymerizable composition according to claim 8, further comprising (C) a colorant, wherein (C) the colorant is a black colorant.

12. The polymerizable composition according to claim 8, further comprising (C) a colorant.

13. The polymerizable composition according to claim 8, wherein the polymerizable composition is used for forming a colored area in a color filter.

14. A color filter comprising:
a support; and
a colored area formed by using the polymerizable composition according to claim 8, on the support.

15. A solid-state imaging device, comprising the color filter according to claim 14.

16. A method of producing a color filter, comprising:
applying the polymerizable composition according to claim 8 to a support to form a polymerizable composition layer;
subjecting the polymerizable composition layer to pattern exposure; and
developing the polymerizable composition layer after the exposure to form a colored pattern.

17. A planographic printing plate precursor, comprising:
a support; and
a photosensitive layer comprising the polymerizable composition according to claim 8, on the support.

\* \* \* \* \*